United States Patent
Laskin et al.

(10) Patent No.: US 10,752,582 B2
(45) Date of Patent: Aug. 25, 2020

(54) AUGMENTING MOIETIES FOR ANTI-INFLAMMATORY COMPOUNDS

(71) Applicants: Rutgers, The State University of New Jersey, New Brunswick, NJ (US); Lehigh University, Bethlehem, PA (US)

(72) Inventors: Jeffrey D. Laskin, Piscataway, NJ (US); Diane E. Heck, Rumson, NJ (US); Carl J. Lacey, Schnecksville, PA (US); Ned D. Heindel, Easton, PA (US); Sherri C. Young, Bloomsbury, NJ (US)

(73) Assignees: LEHIGH UNIVERSITY, Bethlehem, PA (US); RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 16/022,019

(22) Filed: Jun. 28, 2018

(65) Prior Publication Data
US 2018/0305310 A1   Oct. 25, 2018

Related U.S. Application Data

(60) Continuation-in-part of application No. 15/365,088, filed on Nov. 30, 2016, and a continuation of application No. 15/334,882, filed on Oct. 26, 2016, now abandoned, which is a continuation-in-part of application No. 14/776,857, filed as application No. PCT/US2014/028329 on Mar. 14, 2014, now Pat. No. 9,512,068, said application No. 15/365,088 is a division of application No. 13/127,284, filed as application No. PCT/US2009/005971 on Nov. 3, 2009, now abandoned.

(60) Provisional application No. 61/790,870, filed on Mar. 15, 2013, provisional application No. 61/793,842, filed on Mar. 15, 2013, provisional application No. 61/198,147, filed on Nov. 3, 2008.

(51) Int. Cl.
| | | |
|---|---|---|
| *C07D 207/16* | (2006.01) | |
| *C07D 209/18* | (2006.01) | |
| *A61K 47/54* | (2017.01) | |
| *A61K 47/55* | (2017.01) | |

(52) U.S. Cl.
CPC .......... *C07D 207/16* (2013.01); *A61K 47/542* (2017.08); *A61K 47/543* (2017.08); *A61K 47/55* (2017.08); *C07D 209/18* (2013.01)

(58) Field of Classification Search
CPC .. C07D 207/16; C07D 209/18; C07D 209/26; A61K 47/542; A61K 47/543; A61K 47/55; A61K 31/132; A61K 31/198; A61K 31/27; A61K 31/4015; A61K 31/405; C07C 2601/16; C07C 2602/42; C07C 271/12; C07C 271/16; C07C 271/22; C07C 271/34; C07C 271/48; C07C 271/50; C07C 271/52

See application file for complete search history.

(56) References Cited

U.S. PATENT DOCUMENTS

| | | |
|---|---|---|
| 3,983,178 A | 9/1976 | Pattison et al. |
| 4,206,310 A | 6/1980 | Mukaiyama et al. |
| 4,420,490 A * | 12/1983 | Sallmann ............. C07K 5/0202 514/539 |
| 4,639,438 A | 1/1987 | Sehring et al. |
| 5,082,964 A | 1/1992 | Heindel et al. |
| 5,434,170 A | 7/1995 | Andrulis, Jr. |
| 2005/0234244 A1 | 10/2005 | Bartolini et al. |

FOREIGN PATENT DOCUMENTS

| | | |
|---|---|---|
| DE | 3223949 A1 | 12/1983 |
| EP | 0289262 A2 | 11/1988 |
| WO | 2004017967 A1 | 3/2004 |
| WO | 2006036994 A2 | 4/2006 |
| WO | 2006/054832 A1 | 5/2006 |

OTHER PUBLICATIONS

Pardutz ( NSAIDs in the Acute Treatment of Migraine: A Review of Clinical and Experimental Data, Pharmaceuticals 2010, 3, 1966-1987) (Year: 2010).*
Young et al. (Bioorg. Med. Chem. Lett. 20, pp. 2987-2990, 2010) (Year: 2010).*
Search Report dated Mar. 16, 2010 in International Application No. PCT/US2009/005971.
International Preliminary Report on Patentability dated May 3, 2011 in International Patent Application No. PCT/US2009/005971.
Amitai et al. "Bifunctional Compounds Eliciting Anti-inflammatory and Anti-cholinesterase Activity as Potential Treatment of Nerve and Blister Chemical Agents Poisoning" Journal of Applied Toxicology 2006 26:81-87.

(Continued)

*Primary Examiner* — Yevgeny Valenrod
*Assistant Examiner* — Blaine G Doletski
(74) *Attorney, Agent, or Firm* — Fox Rothschild LLP

(57) ABSTRACT

Augmented or synergized anti-inflammatory constructs are disclosed including anti-inflammatory amino acids covalently conjugated with other anti-inflammatory molecules such as nonsteroidal anti-inflammatory drugs, vanilloids and ketone bodies. Further conjugation with a choline bioisostere or an additional anti-inflammatory moiety further augments the anti-inflammatory activity.

15 Claims, No Drawings

(56) References Cited

OTHER PUBLICATIONS

Appendino et al. "Chemoselective Esterification of Phenolic Acids and Alcohols" Organic Letters 2002 4(22):3839-3841.
Boyle et al. "Synthesis and Study of Thiocarbonate Derivatives of Choline as Potential Inhibitors of Acetylcholinesterase" Journal of Medicinal Chemistry 1997 40:3009-3013.
Brenner et al. "Arylcholine Carbonates and Aryl-3,3-dimethly-I-butyl Carbonates as Inhibitors and Inactivators of Acetylcholinesterase" Inhibitors and Inactivators of Acetylcholinesterase. Synthesis and Chemistry of Agrochemicals II. Washington, D.C.: ACS Publishers, 1991. 469-477.
Buck et al. "Chlorthiophos(S 2957)and Its Related Compounds; Chemistry and Biological Activity" VIII International Congress of Plant Protection, Papers at Sessions 1975 3(1):119-127.
But, T. Y. S. and Toy, P. H. "The Mitsunobu Reaction: Origin, Mechanism, Improvements, and Applications" Chemistry—An Asian Journal 2007 2:1340-1355.
Cohen et al. "Effects of Charge, Volume, and Surface on Binding of Inhibitor and Substrate Moieties to Acetylcholinesterase" Journal of Medicinal Chemistry 1985 28(9):1309-1313.
Dahan et al. "A Novel Mechanism for Oral Controlled Release of Drugs by Continuous Degradation of a Phospholipid Prodrug Along the Intestine: In-vivo and In-vitro Evaluation of an Indomethacin-Lecithin Conjugate" Journal of Controlled Release 2007 119:86-93.
Dvir et al. "DP-155, a Lecithin Derivative of Indomethacin, is a Novel Nonsteroidal Antiinflammatory Drug for Analgesia and Alzheimer's Disease Therapy" CNS Drug Reviews 2007 13(2):260-277.
Fontana et al. "Cytochrome P450 Enzymes Mechanism Based Inhibitors: Common Sub-structures and Reactivity" Current Drug Metabolism 2005 6:413-454.
Halen et al. "Combining Anticholinergic and Anti-Inflammatory Activities into a Single Moiety: A Novel Approach to Reduce Gastrointestinal Toxicity of Ibuprofen and Ketoprofen" Chemical Biology and Drug Design 2007 70:450-455.
Halen et al. "Substituted Aminoalcohol Ester Analogs of Indomethacin With Reduced Toxic Effects" Medicinal Chemistry Research 2007 16:101-111.
Inestrosa, N.C. and Toledo, E.M. "The Role of Wnt Signaling in Neuronal Dysfunction in Alzheimer's Disease" Molecular Neurodegeneration 2008 3(9):1-13.
Kalgutkar et al. "Ester and Amide Derivatives of the Nonsteroidal Antiinflammatory Drug, Indomethacin, as Selective Cyclooxygenase-2 Inhibitors" Journal of Medicinal Chemistry 2000 43:2860-2870.
Kwiecien et al. "Nitric Oxide (NO)-Releasing Aspirin and (NO) Donors in Protection of Gastric Mucosa Against Stress" Journal of Physiology and Pharmacology 2008 59(Suppl 2):103-115.
Ono et al. "A Convenient Procedure for Esterification of Carboxylic Acids" Bulletin of the Chemical Society of Japan 1978 51(8):2401-2404.
Østergaard, J. and Larsen, C. "Bioreversible Derivatives of Phenol. 2. Reactivity of Carbonate Esters with Fatty Acid-like Structures Towards Hydrolysis in Aqueous Solutions" Molecules 2007 12:2396-2412.
Prusakiewicz et al. "Comparison of Skin Esterase Activities from Different Species" Pharmaceutical Research 2006 vol. 23(7):1517-1524.
Rautio et al. "Prodrugs: Design and Clinical Applications" Nature Reviews Drug Discovery 2008 7:255-270.
Schumann et al. "Diallylaluminium-N,N-Dimethylaminoethanolate, the First Stable Allyl-Alane Suitable for Additions to Aldehydes, Ketones and Imines" Tetrahedron Letters 2002 43:3507-3511.
Sylvain et al. "An Efficient Procedure for the Esterification of Nitroacetic Acid: Application to the Preparation of Merrifield Resin-Bound Nitroacetate" Tetrahedron Letters 1999 40:875-878.
Tamaddon et al. "A Green Protocol for Chemoselective 0-Acylation in the Presence of Zinc Oxide as a Heterogeneous, Reusable and Eco-friendly Catalyst" Tetrahedron Letters 2005 46:7841-7844.
Vaddi et al. "Human Skin Permeation of Branched-Chain 3-0-Alkyl Ester and Carbonate Prodrugs of Naltrexone" Pharmaceutical Research 2005 22(5):758-765.
Venuti et al. "Synthesis and Biological Evaluation of Q-(N,N,N-Trialkylammonium)alkyl Esters and Thioesters of Carboxylic Acid Nonsteroidal Antiinflammatory Agents" Pharmaceutical Research 1989 6(10):867-873.
Wang et al. "Nicotinic Acetylcholine Receptor alpha-7 Subunit is an Essential Regulator of Inflammation" Nature 2003 421:384-388.
Wang et al. "Synthesis and Bioactivity of Novel Phthalimide Derivatives" Chinese Chemical Letters 2008 19:26-28.
Williams et al. "NO-Donating Aspirin Inhibits the Activation of NF-KB in Human Cancer Cell Lines and Min Mice" Carcinogenesis 2008 29(2):390-397.
Farias et al. 2005, Neurobiology of disease, vol. 18, pp. 176-183.
Jain, et al: "QSAR Analysis of Indomethacin Derivatives as Selective COX-2 Inhibitors", Internet Electronic Journal of Molecular Design, Apr. 2006, vol. 5, No. 4, pp. 224-236.
Chang et al., "Therapeutic Potential of a non-steroidal bifunctional anti-inflammatory and anti-cholinergic agent against skin injury induced by sulfur mustard," Toxicoloy and Appliced Pharmacology (2014); 280:236-244.
Young et al., "Peripheral site acetylcholinesterase inhibitors targeting both inflammation and cholinergic dysfunction," Bioorganic & MEdicinal Chemistry Letters (2010); 20:2987-2990.
Gacem et al., "Esterification of sterically hindered acids and alcohols in fluorous media," Tetrahedron Letters (2003); 44:1391-1393.
Bosse et al., "Synthesis and SAR of novel 1,1-dialkyl-2(1H)-naphthalenones as potent HCV polymerase inhibitors," Bioorganic & Medicinal Chemistry Letters (2008); 18:568-570.
Carey et al., "Part A: Structure and Mechanisms," Advanced Organic Chemistry, Fifth Edition (2007); p. 299.
Streitwieser Jr., Andrew, "Solvolytic Displacement Reactions at Saturated Carbon Atoms," Chem. Rev. (1956); 56(4):585.
Zimmer et al., Sterically Hindered Group IVA Organometallics VIII*. Preparation and Some Properties of Neohexyltin Compounds, J. Organometal, Chem. (1968); 14:222-224.
Zimmer et al., "Sterically Hindered Group IVA Organometallics. Preparation and Properties of Certain neopentyltins," J. Org. Chem (1964); 29(9):2632-2636.

* cited by examiner

AUGMENTING MOIETIES FOR ANTI-INFLAMMATORY COMPOUNDS

CROSS-REFERENCE TO RELATED APPLICATIONS

This application is a Continuation of U.S. patent application Ser. No. 15/334,882, filed on Oct. 26, 2016, which is a Continuation-In-Part of U.S. patent application Ser. No. 14/776,857, filed on Sep. 15, 2015, which is the U.S. National Phase of International Patent Application Serial No. PCT/US14/28329, filed on Mar. 14, 2014, which claims the benefit of priority under 35 U.S.C. 119(e) of U.S. Provisional Application No. 61/790,870, filed on Mar. 15, 2013, and of U.S. Provisional Application No. 61/793,842, filed on Mar. 15, 2013. This application is also a Continuation-In-Part of U.S. patent application Ser. No. 15/365,088, filed on Nov. 30, 2016, which is a Division of U.S. patent application Ser. No. 13/127,284, filed on Sep. 23, 2011, which is the U.S. National Phase of International Patent Application Serial No. PCT/US09/05971, filed on Nov. 3, 2009, which claims the benefit of priority under 35 U.S.C. 119(e) of U.S. Provisional Application No. 61/198,147, filed on Nov. 3, 2008. The disclosures of all of the above are incorporated herein by reference in their entireties.

STATEMENT REGARDING FEDERALLY SPONSORED RESEARCH OR DEVELOPMENT

This invention was made with government support under Grant No. U54AR055073 awarded by the National Institutes of Health. The government has certain rights in the invention.

FIELD OF THE INVENTION

The invention is directed to anti-inflammatory compounds which are synergistically enhanced in their anti-inflammatory activity through conjugation with specific amino acids and/or with specific other anti-inflammatory components. Also disclosed are methods of increasing the activity of an anti-inflammatory compound, which involve conjugating the anti-inflammatory compound with an amino acid and optionally further conjugating with a choline bioisostere, or conjugating one, two or more anti-inflammatory compounds with each other, for example, terpene, amino acid, vanilloid, or polyamine.

BACKGROUND OF THE INVENTION

The term "anti-inflammatory" refers to the property of a compound that reduces inflammation. Anti-inflammatory drugs make up about half of analgesics, remedying pain by reducing inflammation.

Nonsteroidal anti-inflammatory drugs (NSAIDs) are a class of drugs that provide analgesic and antipyretic (fever-reducing) effects, and, in higher doses, anti-inflammatory effects. The term "nonsteroidal" distinguishes these drugs from steroids, which, among a broad range of other effects, have a similar eicosanoid-depressing, anti-inflammatory action. As analgesics, NSAIDs are unusual in that they are non-narcotic. The most prominent members of the NSAID group of drugs are aspirin, ibuprofen and naproxen.

The widespread use of NSAIDs has meant that the adverse effects of these drugs are well known and have become increasingly prevalent as the population ages. The two main adverse drug reactions (ADRs) associated with NSAID use are gastrointestinal (GI) and renal effects. These effects are dose-dependent and, in many cases, severe enough to pose the risk of ulcer perforation, upper gastrointestinal bleeding, and death, thereby limiting the use of NSAID therapy. An estimated 10-20% of NSAID patients experience dyspepsia, and NSAID-associated upper GI adverse events are estimated to result in 103,000 hospitalizations and 16,500 deaths per year in the United States and represent 43% of drug-related emergency visits. Thus, the clinical problems with NSAIDs and the need for replacement anti-inflammatories are well recognized.

For at least these reasons, it would be desirable to find substitutes for the current NSAIDs having increased anti-inflammatory potency and a higher safety margin.

BRIEF SUMMARY OF THE INVENTION

It has now been discovered that one solution to this problem is to improve the potency and safety of anti-inflammatory compounds through the covalent combination of component anti-inflammatory moieties and/or conjugation with a specific amino acid, optionally with further conjugation with a choline bioisostere.

Aspect I

Terpenes, amino acids, aliphatic polyamines such as spermine and spermidine, and vanilloid platforms (e.g., 4-hydroxy-3-methoxybenzyl amine, commonly called vanillylamine; 4-hydroxy-3-methoxybenzyl alcohol, commonly called vanillyl alcohol; zingerone; [6]-paradol; and eugenol), are known to display modest anti-inflammatory and antinociceptive activity in animal and cellular models. In addition, aliphatic and alicyclic carbamates are known to be inhibitors of fatty acid amide hydrolase (FAAH), an enzyme whose inhibition is linked to anti-inflammatory effects. Thus, the individual components of the anti-inflammatory constructs of a first aspect of the invention, and the bonds that link them all together, provide a therapeutic benefit that can be greater than the sum of the parts.

It has now been discovered that the double and triple combinations of these anti-inflammatory components covalently linked together with at least one carbamate bond yields an augmented anti-inflammatory molecule whose net activity exceeds that of its individual building blocks. Some of these assemblies exceed the anti-inflammatory effects of the traditional NSAIDs.

The specific structural assemblies claimed herein include:
Formula 1 terpene—vanilloid
Formula 2 vanilloid—polyamine—vanilloid
Formula 3 vanilloid—amino acid—terpene
Formula 4 terpene—polyamine—terpene
Formula 5 vanilloid—amino acid—vanilloid
Formula 6 terpene—amino acid—terpene
Formula 7 terpene—amino acid—vanilloid In one embodiment, the carbamate-linked structures have the following general structures:
Formula 1A terpene—(carbamate)—vanilloid
Formula 2A vanilloid—(carbamate)—polyamine—(carbamate)—vanilloid
Formula 3A vanilloid—(carbamate)—amino acid—(ester)—terpene
Formula 4A terpene—(carbamate)—polyamine—(carbamate)—terpene
Formula 5A vanilloid—(carbamate)—amino acid—(amide)—vanilloid Formula 6A terpene—(carbamate)—amino acid—(ester)—terpene Formula 7A terpene—(carbamate)—amino acid—(amide)—vanilloid Specific examples of the components usable in construction of Formulae 1 to 7 and 1A to 7A anti-inflammatory conjugates include the following.

For terpenes: The terpene of the synergistic anti-inflammatory drug conjugate is selected from the group consisting of thymol, carvacrol, menthol, geraniol, nerol, farnesol, myrtenol, cumyl alcohol, citronellol, borneol, linalool, alpha-terpineol, and perillyl alcohol. If the drug construct contains more than one terpene molecule, they may be different or the same.

For vanilloids: The vanilloid moiety of the synergistic anti-inflammatory drug conjugate is selected from the group consisting of 4-hydroxy-3-methoxybenzyl amine commonly called vanillylamine, 4-hydroxy-3-methoxybenzyl alcohol commonly called vanillyl alcohol, zingerone, [6]-paradol, and eugenol. If the drug construct contains more than one vanilloid molecule, they may be different or the same.

For polyamines: The polyamine anti-inflammatory component is selected from the group consisting of spermidine, spermine and putrescine.

For amino acids: The amino acid anti-inflammatory moiety is selected from valine, leucine, isoleucine, glycine, cysteine, phenylalanine, norvaline, and other suitable amino acids known to possess anti-inflammatory activity. The amino acids can be chiral or racemic. The chirality of the chiral amino acids can be L- or R- depending on the desired activity and release profile.

Aspect II

A second aspect of the present invention is directed to the surprising discovery that conjugation of certain anti-inflammatory moieties, especially NSAIDs, vanilloids, and ketone bodies, with selected amino acids, and optionally further conjugated with a choline bioisostere, synergistically increases the anti-inflammatory activity of the conjugate, when compared to the anti-inflammatory drug itself.

Thus, one embodiment of the present invention is directed to a synergistic anti-inflammatory drug—amino acid conjugate, comprising (a) at least one anti-inflammatory compound, and (b) at least one amino acid covalently linked to the anti-inflammatory compound, where the anti-inflammatory activity of the conjugate is greater than the activity of the anti-inflammatory compound alone. The synergistic anti-inflammatory drug—amino acid conjugate can further incorporate a choline bioisostere (e.g., the 3,3-dimethylbutyl moiety, —OCH$_2$CH$_2$C(CH$_3$)$_3$, or it's silicon analog, —OCH$_2$CH$_2$Si(CH$_3$)$_3$), preferably as the ester, so that another embodiment of the present invention is directed to a synergistic anti-inflammatory drug—amino acid—choline bioisostere conjugate, comprising (a) the anti-inflammatory drug—amino acid conjugate above, and (b) a choline bioisosteric ester, covalently linked to the amino acid carboxyl of said anti-inflammatory drug—amino acid conjugate.

In one embodiment the amino acid is covalently linked to the platform therapeutic agent through an amino or carboxyl group as either an amide or an ester moiety.

In one embodiment the amino acid of the synergistic anti-inflammatory drug—amino acid conjugate is selected from the group consisting of valine, nor-valine, leucine, iso-leucine, glycine, cysteine, proline and phenylalanine.

In one embodiment the anti-inflammatory compound is selected from the group consisting of non-steroidal anti-inflammatory drugs (NSAIDs), vanilloids, and ketone bodies. In a particular embodiment, the NSAID is selected from the group consisting of diclofenac, ibuprofen, naproxen, and indomethacin. The vanilloid is selected from vanillyl alcohol, phenolic hydroxyl-protected vanillyl alcohol (3-methoxy-4-acetyloxybenzyl alcohol), and vanillylamine. The ketone body is selected from 3-hydroxybutyrate or a homologue thereof. Vanillyl alcohol and vanillylamine are both known to possess anti-inflammatory properties. So-called "ketone bodies" of which 3-hydroxybutyric acid is a prime example, have been increasingly recognized as possessing anti-inflammatory properties.

In one embodiment, the synergistic anti-inflammatory drug—amino acid conjugate has the structure of Formula (I):

AI-NH—CHR—C(=O)O-Q$^1$    Formula (I)

where AI represents an anti-inflammatory drug moiety such as an NSAID-CO—, a vanillyl moiety, or 3-hydroxybutyryl, where R is selected from the group consisting of hydrogen, optionally substituted alkyl, optionally substituted cycloalkyl, optionally substituted aryl, and optionally substituted heteroaryl, and where Q$^1$ can be selected from hydrogen, alkyl or heteroalkyl. In one specific embodiment, Q$^1$=—CH$_2$CH$_2$C(CH$_3$)$_3$. Examples of this embodiment include NDH 4476, 4535, 4537, 4572, 4576, 4577, 4578, 4591, 4595, 4596, 4613, 4614, 4615, 4617, 4618, 4619, 4627, 4628, 4651, 4652, 4653, and 4654 as referenced herein.

In another embodiment, the synergistic anti-inflammatory drug—amino acid conjugate has the structure of Formula (II):

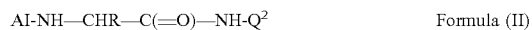

AI-NH—CHR—C(=O)—NH-Q$^2$    Formula (II)

where AI represents an anti-inflammatory moiety (viz, NSAID-CO—, vanillyl alcohol-CO—, and such ketone bodies as 3-hydroxybutyryl); R is selected from the group consisting of hydrogen, optionally substituted alkyl, optionally substituted cycloalkyl, optionally substituted aryl, and optionally substituted heteroaryl; Q$^2$ is selected from hydrogen or the vanillyl moiety (i.e., 3-methoxy-4-hydroxybenzyl), —CH$_2$CH$_2$C(CH$_3$)$_3$ or —CH$_2$CH$_2$Si(CH$_3$)$_3$. If vanillylamine (i.e., 3-methoxy-4-hydroxybenzyl-NH—) is attached to any of these anti-inflammatory amino acid platforms it constitutes a shelf-stable, slowly metabolized moiety. However, if vanillyl alcohol (i.e., 3-methoxy-4-hydroxybenzyl-O—) is attached, the resulting candidate pharmaceuticals are unstable unless the free-phenolic hydroxyl is protected by acylation. Acetate is a preferred protecting group and the derived products are suitable therapeutic candidates. Examples of this embodiment include NDH 4479, 4483, and 4571 as referenced herein.

DETAILED DESCRIPTION OF THE INVENTION

Aspect I

Surprisingly, it has now been discovered that weak anti-inflammatory moieties can be covalently linked by carbamate bonds to yield conjugate constructs of enhanced potency for suppression of inflammation.

One aspect of the present invention is directed to an anti-inflammatory conjugate where the anti-inflammatory component comprises at least one compound selected from the group consisting of anti-inflammatory terpenes, antiinflammatory vanilloids, anti-inflammatory polyamines and anti-inflammatory amino acids.

A related aspect of the invention is directed to a method of improving the potency of an anti-inflammatory compound by linking it to another anti-inflammatory compound via a carbamate linkage, where the potency of the conjugate is greater than the sum of its parts.

In one embodiment of the present invention the terpene, amino acid, vanilloid, or polyamine is not employed as a single component but as an augmenting component, covalently linked by a carbamate moiety to another anti-inflammatory moiety or to two other anti-inflammatory moieties, wherein they together serve to enhance or synergize performance. The conjugates may be bifunctional (meaning just two moieties) or tri-functional (meaning three components), or higher. In addition the carbamate linking bond itself can also convey anti-inflammatory activity to the conjugate.

Carbamate compounds are known to achieve anti-inflammation effect in vivo by inhibition of fatty acid amide hydrolase. In an inhibitory screen against fatty acid amide hydrolase (FAAH), the inventive carbamates were found to possess $IC_{50}$ values which ranged from 9 µM to 1 mM for inhibition of FAAH. Some molecules were too lipophilic to dissolve in the enzyme assay medium and hence could not be tested. While there was no direct linear correlation between the compound's efficacy as an FAAH inhibitor and its potency in suppressing inflammation, many of the best inflammation suppressants were also FAAH inhibitors. The FAAH $IC_{50}$ values are noted with the compound examples.

Hydrolysis of the conjugates can release the terpene and any other co-anti-inflammatories to affect the therapeutic benefit in vivo. Unfortunately, in several cases hydrolysis was too fast (of the order of minutes) to make the compounds practical as pharmaceuticals and stabilization of the conjugate had to be addressed.

For example, as exemplified by the structures NDH4481, 4483, and 4485, if one attempts the incorporation into a conjugate of the vanilloid vanillyl alcohol (also known as 4-hydroxy-3-methoxybenzyl alcohol) through its benzyl alcohol component (the —CH$_2$OH), a conjugate is produced that is rapidly hydrolyzed. It is known that 4-hydroxy benzyl-X systems [e.g., p-HO—Ar—CH$_2$—X], wherein X is a good leaving group, can rapidly decompose via a quinone methide intermediate. Capping the phenolic hydroxyl with an acetate group solves the problem, and hydrolysis lifetimes of >2 hours are then observed. This problem is not observed with the vanillylamines when linked through their amino nitrogens; these are stable materials.

A second case of decomposition that is too rapid can be seen in NDH4590 and 4593. Even though these compounds have impressive anti-inflammatory effects in the Mouse Ear Vesicant Model (MEVM) assay, their half-lives in sera or in any polar aqueous medium are comparatively short (hours). We have discovered that this is because the nucleophilic internal secondary amine NH executes an intramolecular nucleophilic attack on the carbonyl of the carbamate thereby freeing the terpene or the vanilloid component. This is a controllable, or tunable, chemically-induced hydrolysis that does not require an enzyme.

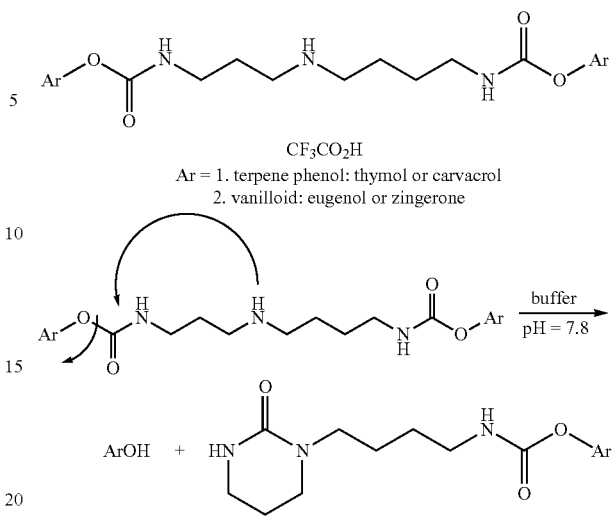

CF$_3$CO$_2$H
Ar = 1. terpene phenol: thymol or carvacrol
2. vanilloid: eugenol or zingerone These compounds possess a terpene or vanilloid carbamate at both ends of the molecule in each case. With the unsymmetrical polyamine we have found that the cyclization occurs to form the six-membered ring only (versus a seven-membered ring).

Either making a salt (such as the trifluoroacetate, hydrochloride, mesylate, or other pharmaceutically acceptable salt) or a labile amide (for example, the trifluoroacetamide, trinitrobenzamide, or tris-trifluorobenzamide) on the internal NH solves the problem, and sufficiently long hydrolysis half-lives are then observed (days). The anti-inflammatory activity was unaffected by these stabilizing modifications, only the time of on-set of the effect was varied (cf. NDH4616, 4622, 4630, 4631, 4635, 4637 and 4649). Half-life for release can be controlled or tuned as noted above, by protonation or amide formation, but it can also be controlled by varying the nature of the anti-inflammatory leaving group. For example, zingerone is released much faster (half-life about 2 hours) than are carvacrol or thymol (half-lives about 2 days), which in turn are released much faster than an aliphatic terpene such as geraniol or borneol (marginal release after several days). The kinetics of release follow the typical organic moiety "leaving group" abilities.

Aspect II

Surprisingly, it has now been discovered that selected amino acids (for example valine, leucine, isoleucine, glycine, cysteine, phenylalanine, proline and norvaline) potentiate or synergize the activity of anti-inflammatory drugs when covalently attached to the parent drug molecules. When attached to known anti-inflammatory moieties, these amino acids augment, or synergize, the anti-inflammatory potency, provide a bio-compatible controlled-release, and permit adjustment of the pharmacologic properties of the parent anti-inflammatory drug.

Thus, in a second aspect of the invention, the amino acid can be used as a "capping" group on an anti-inflammatory such as a NSAID, a vanillyl alcohol or a vanillylamine. In one embodiment, the amino acid can be attached through its amino group to a carboxyl group in the platform anti-inflammatory molecule leaving a pendant carboxyl from the amino acid which can be free ($Q^1$=H) or can be esterified ($Q^1$=alkyl) for enhancement of properties or for ease of handling. A preferred alkyl group is a choline mimic, such as —CH$_2$CH$_2$C(CH$_3$)$_3$ or its silicon bioisostere, —CH$_2$CH$_2$Si(CH$_3$)$_3$. In one specific embodiment, constructs or scaffolds of this type can be characterized as shown in Formula (I):

AI—NH—CHR—C(=O)O-Q$^1$    Formula (I)

In a second embodiment, herein called Formula (II), when one anti-inflammatory compound contains an amino group, such as in the transient receptor potential cation channel subfamily V member 1 (TRPV1) inhibitor vanillylamine, the amino acid augmentation moiety can be linked via its carboxyl resulting in a pendant amino to which can be attached a second anti-inflammatory component such as an NSAID-CO—, a vanillyl alcohol-CO—, or a 3-hydroxybutyryl (3-HB) unit (as representative of a ketone body).

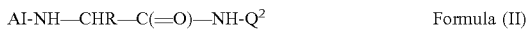
AI—NH—CHR—C(=O)—NH-Q$^2$    Formula (II)

NDH 4571 in which 3-BB is mounted on a valine platform linked to a vanilloid, diplayed a 69% suppression of chloroethyl ethyl sulfide (CEES)-induced inflammation at the standard test dosage in the MEVM, considerably higher than any of the fragment pieces of that conjugate.

Present Embodiments

One aspect of the invention is directed to an anti-inflammatory drug—amino acid conjugate, comprising: (a) at least one anti-inflammatory compound conjugated with (b) an augmenting moiety comprising an anti-inflammatory amino acid selected from the group consisting of valine, nor-valine, leucine, iso-leucine, glycine, cysteine, proline and phenylalanine; wherein conjugation is via the nitrogen atom of the amino acid of the augmenting moiety; and wherein the anti-inflammatory activity of the conjugate is greater than the sum of its parts. Preferably the anti-inflammatory drug—amino acid conjugate contains a core anti-inflammatory amino acid, with supplemental anti-inflammatory agents or moieties covalently attached to both the carboxylic acid group and the amino group, where these supplemental anti-inflammatory morieties or agents are not amino acids. The inventive conjugate can also have a dipeptide core rather than a monomeric amino acid, but the core is not a higher oligopeptide or a protein. Thus, not only the anti-inflammatory monomeric amino acids but also di-peptides containing at least one of the anti-inflammatory amino acids constitute useful bi-functional platforms to carry the supplemental anti-inflammatory moieties. Such dipeptides include, for example, valyl valine, valyl glycine, valyl alanine, valyl proline, valyl phenylalanine, glycyl valine, prolyl valine, phenylalanyl valine, isoleucyl valine, alanyl valine, glycyl proline, prolyl glycine, glycyl phenylalanine, phenylalanyl glycine, prolyl phenylalanine, phenylalanyl proline and related bis-amino acid units.

With regard to amino acid chemistry it is commonly understood that the verb "to conjugate" refers to reacting an amino substituent in one conjugation partner with a carboxylic acid substituent (or suitably activated carboxylate group) on a second conjugation partner, with elimination of a small molecule (typically water), thereby joining the two partners via an amide bond. Similarly, the verb "to conjugate" also signifies "to join together" in grammar, as in "to conjugate a verb". Thus in chemistry, a conjugate is a chemical compound that has been formed by the joining of two or more compounds.

In one embodiment the amino acid of the anti-inflammatory drug—amino acid conjugate is selected from the group consisting of valine, glycine, proline and phenylalanine. Preferably the amino acid is valine or proline or phenylalanine. More preferably the amino acid is valine or phenylalanine. In one embodiment the amino acid is valine. In another embodiment the amino acid is phenylalanine.

In one embodiment the augmenting moiety is an amino acid ester of the choline bioisosteres HOCH$_2$CH$_2$C(CH$_3$)$_3$ or HOCH$_2$CH$_2$Si(CH$_3$)$_3$, or an amino acid amide of the choline bioisosteres H$_2$NCH$_2$CH$_2$C(CH$_3$)$_3$ or H$_2$NCH$_2$CH$_2$Si(CH$_3$)$_3$. In another embodiment the augmenting moiety is a valine ester or amide. In another embodiment the augmenting moiety is a phenylalanine ester or amide. In another embodiment the augmenting moiety is a proline ester or amide. In one embodiment the augmenting moiety is an amino acid ester or amide of a vanilloid. Preferably the vanilloid is selected from the group consisting of vanillyl alcohol, vanillyl amine and phenol-protected derivatives thereof. Phenol-protected derivatives include O-acylated analogs, such as acetyloxy (also known as "acetoxy") and benzoyloxy compounds.

In one embodiment the anti-inflammatory compound is selected from the group consisting of non-steroidal anti-inflammatory drugs (NSAIDs), anti-inflammatory vanilloids and ketone bodies. In one embodiment the NSAID is selected from the group consisting of diclofenac, ibuprofen, naproxen, and indomethacin. In another embodiment the vanilloid is selected from the group consisting of vanillyl alcohol, 3-methoxy-4-acetyloxybenzyl alcohol, and vanillylamine. In yet another embodiment the ketone body is selected from the group consisting of 3-hydroxybutyrate and homologues thereof. "Ketone bodies" such as 3-hydroxybutyrate and acetoacetate are produced as metabolites of fatty acids in the liver. 3-Hydroxybutyrate has inherent anti-inflammatory activity. For purposes of the present disclosure, a "homologue" is defined as a compound belonging to a series of compounds differing from each other by one or more methylene (—CH$_2$—) groups, for example by a single methylene group. Thus 4-hydroxypentanoate and 3-hydroxypentanoate are both higher homologues of 3-hydroxybutyrate, depending on where in the carbon chain the methylene group has been inserted with respect to the hydroxy-bearing carbon of 3-hydroxybutyrate.

In addition to NSAIDs, vanilloids and ketone bodies, other useful anti-inflammatory compounds include anti-inflammatory terpenes (e.g., geraniol, thymol, carvacrol, etc), anti-inflammatory hydroxy-cinnamic acids (e.g., ferulic acid, caffeic acid, and p-coumaric acid), anti-oxidants (e.g., cathecins/catechins and flavanols), indole-3-carbinol, pentoxifylline, and anti-inflammatory fatty acids (e.g., ricinoleic, palmitoleic, and docosahexaenoic).

A related aspect of the invention is directed to an anti-inflammatory drug—amino acid conjugate comprising: (a) an anti-inflammatory compound conjugated with (b) an augmenting moiety comprising an amino acid ester or amide, wherein conjugation is via the nitrogen atom of the amino acid of the augmenting moiety; wherein the amino acid ester or amide is selected from the group consisting of esters and amides of valine, glycine, proline and phenylalanine, wherein the anti-inflammatory compound is selected from the group consisting of (1) the non-steroidal anti-inflammatory drugs diclofenac, ibuprofen, naproxen, and indomethacin; (2) the vanilliods vanillyl alcohol, 3-methoxy-4-acetyloxybenzyl alcohol, and vanillylamine; and (3) the ketone bodies 3-hydroxybutyrate and homologues thereof; andwherein the anti-inflammatory activity of the conjugate is greater than the sum of its parts.

One aspect of the invention is directed to an anti-inflammatory drug—amino acid conjugate having the structure of Formula (I), AI-NH—CHR—C(=O)—O-Q¹, wherein AI represents an anti-inflammatory drug moiety selected from the group consisting of an NSAID-CO— moiety, a vanillyl-CO— moiety and a 3-hydroxybutyroyl moiety; wherein R is selected from the group consisting of hydrogen, isopropyl and benzyl; and wherein Q¹ is selected from the group consisting of alkyl and heteroalkyl. In this aspect the augmenting moiety is an anti-inflammatory amino acid ester. In one embodiment Q¹ is —CH$_2$CH$_2$C(CH$_3$)$_3$ or —CH$_2$CH$_2$Si(CH$_3$)$_3$. In one embodiment, for the NSAID-CO— moiety, the NSAID is selected from the group consisting of diclofenac, naproxen and indomethacin.

A related aspect of the invention is direct to an anti-inflammatory drug—amino acid conjugate having the structure of Formula (II), AI-NH—CHR—C(=O)—NH-Q², wherein AI represents an anti-inflammatory drug moiety selected from the group consisting of an NSAID-CO— moiety, a vanillyl-CO— moiety and a 3-hydroxybutyroyl moiety; wherein R is selected from the group consisting of hydrogen, isopropyl and benzyl; and Q² is 3-methoxy-4-hydroxybenzyl, —CH$_2$CH$_2$C(CH$_3$)$_3$, or —CH$_2$CH$_2$Si(CH$_3$)$_3$. In this aspect the augmenting moiety is an anti-inflammatory amino acid amide. Preferably the anti-inflammatory amino acid amide is not an oligopeptide or a protein, but is a single anti-inflammatory amino acid, or at most a dipeptide containing at least one anti-inflammatory amino acid, reacted with an organic amine with the elimination of water to form an amide bond. The organic amine is preferably a primary or secondary amine. In one embodiment, for the NSAID-CO— moiety, the NSAID is selected from the group consisting of diclofenac, ibuprofen, naproxen and indomethacin.

Another aspect of the invention is directed to a method of increasing the activity of an anti-inflammatory drug, comprising conjugating the anti-inflammatory drug with an amino acid augmenting moiety to provide an amino acid conjugate of Formula (I) or Formula (II). In one embodiment Q¹ of Formula (I) is selected from the group consisting of —CH$_2$CH$_2$C(CH$_3$)$_3$ and —CH$_2$CH$_2$Si(CH$_3$)$_3$. In one embodiment Q² of Formula (II) is —CH$_2$CH$_2$C(CH$_3$)$_3$ or —CH$_2$CH$_2$Si(CH$_3$)$_3$.

Another aspect of the invention is directed to an anti-inflammatory drug—amino acid conjugate selected from the group consisting of:

NDH4479

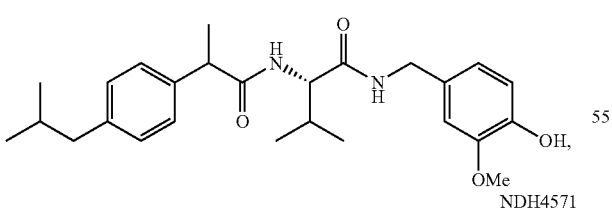

NDH4571

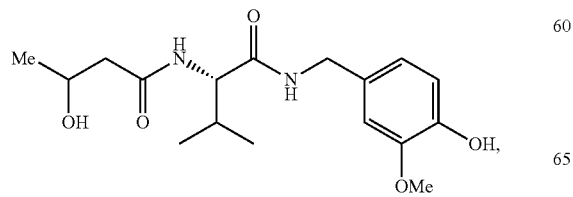

NDH4481

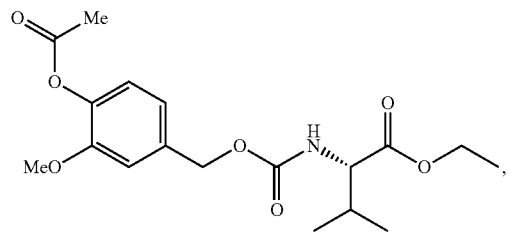

NDH4572

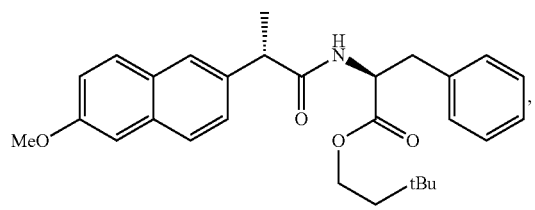

NDH4483

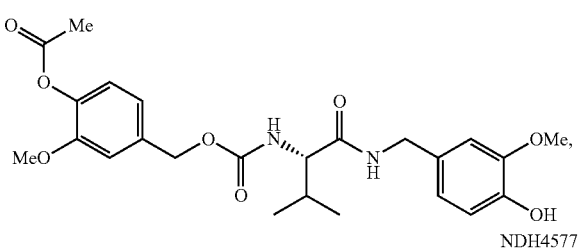

NDH4577

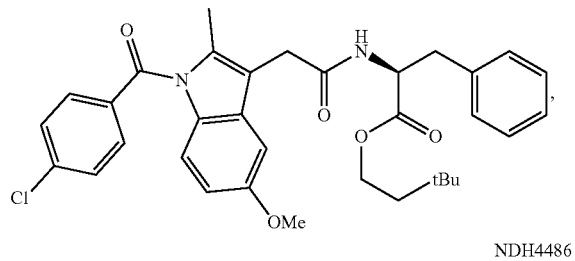

NDH4486

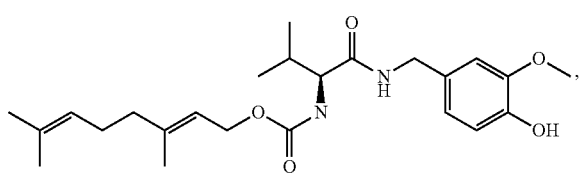

NDH4578

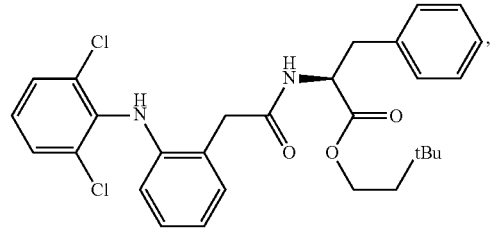

NDH4535

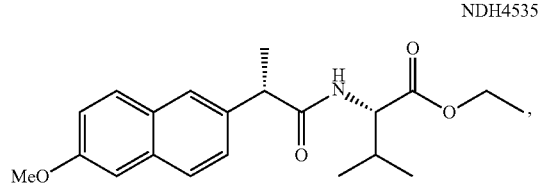

-continued

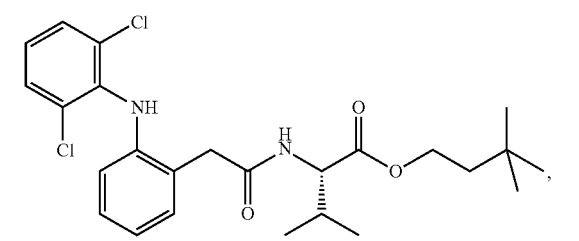
NDH4591

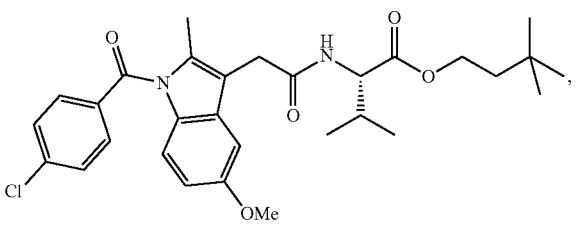
NDH4537

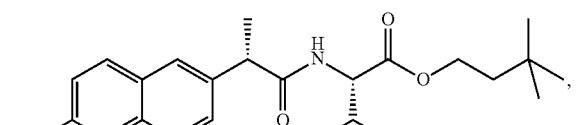
NDH4596

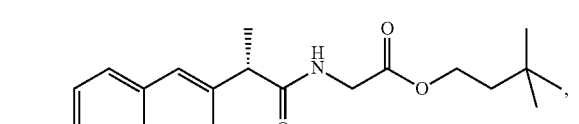
NDH4613

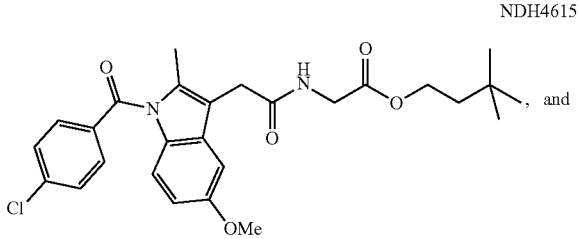
NDH4615

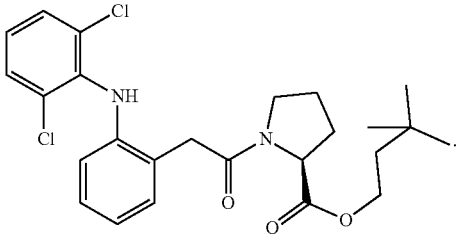
NDH4628

Compounds such as NDH4481 and NDH4535 are simple ethyl esters rather than the more complex 3,3-dimethylbutyl or vanillyl alcohol esters. It is now recognized that ethanol itself possesses anti-inflammatory activity in humans, and therefore serves as an anti-inflammatory augmenting moiety in the anti-inflammatory drug—amino acid conjugate.

Preferably the anti-inflammatory drug—amino acid conjugate is selected from the group consisting of:

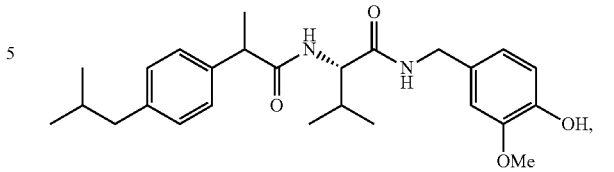
NDH4479

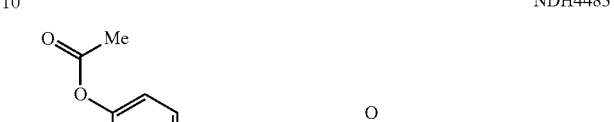
NDH4483

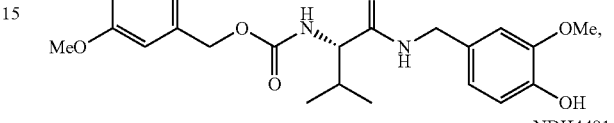
NDH4481

and
NDH4486

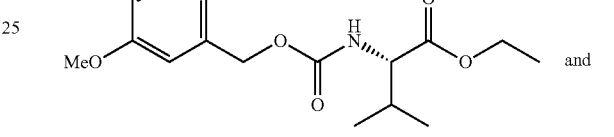

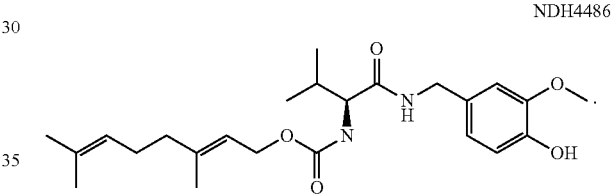

In one embodiment the anti-inflammatory drug—amino acid conjugate is NDH4479. In another embodiment the anti-inflammatory drug—amino acid conjugate is NDH4481. In yet another embodiment the anti-inflammatory drug—amino acid conjugate is NDH4483. In a further embodiment the anti-inflammatory drug—amino acid conjugate is NDH4486.

EXAMPLES

Materials and Methods

All reactants and solvents used were of the highest purity commercial grade and were employed without further purification. All amino acids used herein were the L-amino acids and were purchased from Sigma-Aldrich (Saint Louis, Mo.). The 2-(2-methoxynaphthalene-6-yl) propanoic acid (naproxen) used was the (S)-enantiomer. All other reagents were used as racemates, unless otherwise noted. All reactions were performed in oven-dried apparatus under a nitrogen atmosphere, unless otherwise noted. All solvents used were anhydrous, unless otherwise noted. NMR spectra were recorded on a Bruker multinuclear spectrometer and chemical shifts are reported as ppm using tetramethylsilane (TMS) as an internal standard. $^1$H NMR spectra were recorded at 500 MHz, while $^{13}$C NMR spectra were recorded at 125 MHz. Elemental analyses were performed at Intertek (Whitehouse, N.J.). All thin layer chromatography (TLC) was performed on Analtech silica gel plates (250 microns).

Biological Evaluations

Ellman Assay

The modified Ellman assay for inhibition of acetylcholinesterase (AChE) and the mouse ear vesication assay (MEVA) have been described in detail by us (see S. C. Young et al, *J Appl Tox,* 2012, 32: 135-141). AChE (Type V-S from *electrophorus electricus*), acetylthiocholine iodide (ATChI), 5,5'-dithiobis(2-nitrobenzoic acid) (DTNB) and tacrine from EMD Chemicals (Gibbstown, N.J.). Cholinesterase inhibition was assayed spectrophotometrically at 412 nm according to Ellman's method. Assays were performed in polystyrene 96-well plates (Corning 96-well flat transparent) and a conventional micro-plate reader was employed for kinetic readings (Tecan Infinite 200 multimode). The following reagents were added to the wells: 200 μL of 0.5 mM DTNB in sodium phosphate buffer (100 mM, pH 8), 30 μL of inhibitor stock solution in methanol, 20 μL of 1.25 units/mL of AChE in sodium phosphate buffer (20 mM, pH 7), and 50 μL of 3 mM ATCh in buffer (100 mM, pH 8). Immediately after the substrate was added, the absorption signal was measured at 30 s intervals over 5 min at 25° C. Percentage inhibition was calculated relative to a negative control (methanol). The background signal was measured in control wells containing every reagent except for the substrate. $IC_{50}$ values were obtained from a minimum of eight concentrations in duplicate and by fitting the experimental data with a dose-response curve using Prism software (Version 5.00, GraphPad Software, San Diego, Calif.).

Mouse Ear Vesicant Model (MEVM)

Animal studies were approved by the Rutgers University Institutional Animal Care and Use Committee and received human care in compliance with the institution's guidelines, as outlined in the Guide for the Care and Use of Laboratory Animals of the National Academy of Sciences. Compounds were assessed as inhibitors of inflammation using the MEVM as previously described (Casillas, R P., et al., Therapeutic approaches to dermatotoxicity by sulfur mustard. 1. Modulaton of sulfur mustard-induced cutaneous injury in the mouse ear vesicant model, *J. Appl. Toxicol.,* 2000, 20, Suppl 1, S145-51), except that female CD-1 mice (4-6 weeks old) were used. Either CEES, chloroethyl ethyl sulfide (65 μmoles) or TPA, 12-O-tetradecanoylphorbol-13-acetate, (1.5 nmol) was used to induce inflammation. To evaluate each compound, ears (3-4 mice per group) were treated with 20 μL, of vehicle control (methylene chloride or acetone) or the test compound (1.5 μmol) in 20 μL, of the appropriate vehicle. After 5 h, mice were euthanized and ear punches (6 mm in diameter) were taken and weighed. Once the raw data were obtained, masses of ear punches were averaged and the percent reduction of vesicant-induced edema and inflammation was calculated using the method of Casillas et al. Raw data were analyzed using a one-way ANOVA to evaluate statistical significance ($P<0.05$).

Inflammation suppression, if observed, is of course dose related but is reported herein only at the standard dose mentioned above. On occasion, mostly with ibuprofen analogs, the vesicant-induced damage is augmented by the candidate anti-inflammatory and these substances are designated as irritants. Also, in some cases the anti-inflammatory candidate suppresses the mean weight of the ear punches from the test ears below that observed with the untreated control and these results are stated as >100% suppression.

Examples of Aspect I

The bifunctional and tri-functional conjugates of Aspect I of the invention were prepared and tested in a standard in vivo MEVM assay for their efficacy compared to that of the parent terpene, amino acid, polyamine, or vanilloid from which each was assembled. Terpene inflammation suppression scores (average of TPA-induced and CEES-induced injuries) ranged from myrtenol (6%), thymol (14%), carvacrol (15%), cumyl alcohol (16%), geraniol (35%), menthol (38%), perillyl alcohol (43%), and farnesol (69%). All terpenes, except farnesol, had inflammation suppression scores less than 45%. The inflammation scores of typical vanilloids were similarly low and none exceeded 40%, e.g., vanillin (11%), vanillyl alcohol (31%), and vanillylamine (35%). In this assay inflammation suppression scores for the amino acids and the polyamines were under 30%. The traditional NSAIDs were under 40% in inflammation suppression scores, e.g., ibuprofen (−23%, an irritant/inflammation inducer), S-naproxen (31%), piroxicam (32%), diclofenac (37%), and indomethacin (39%).

The synergistic effects of combination of weakly potent anti-inflammatory components into conjugates are readily evident in the compounds of the invention. As an example of the Formula 1 class recited earlier herein, the terpene carvacrol by itself displayed inflammation suppression of 19% and 10% for CEES and TPA-induced inflammation respectively while its carbamate conjugate with vanillylamine (NDH4574) showed a significantly improved suppression of 89% and 88% (CEES and TPA).

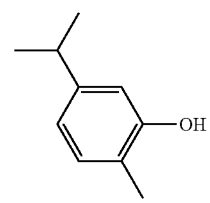

Carvacrol

NDH4576

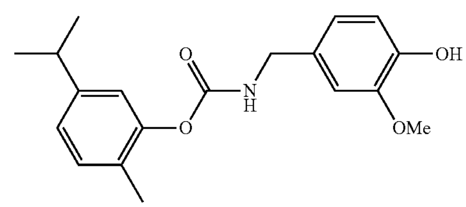

Another Formula 1 conjugate combines the terpene linalool to the vanilloid, vanillylamine, to yield the construct (NDH4624) which displayed a 92% suppression of CEES-induced inflammation.

NDH4624

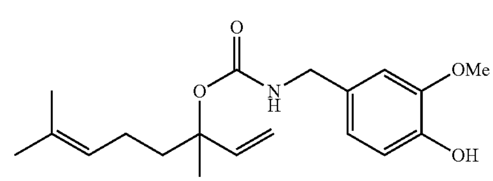

As another example of the Formula 1 conjugate, the terpene (geraniol) coupled to the vanilloid (vanillylamine) by a carbamate linkage and designated as NDH4484 had a 64% suppression (CEES-induced injury) and a 71 μM inhibition of fatty acid amide hydrolase (FAAH).

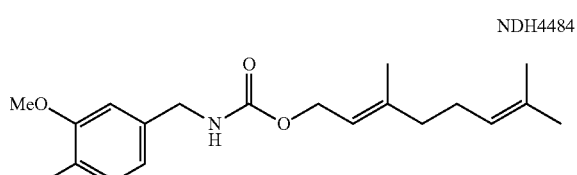
NDH4484

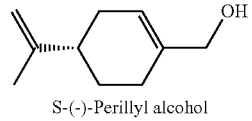
S-(-)-Perillyl alcohol

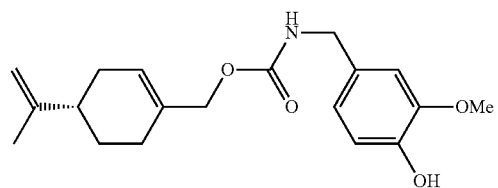
NDH4498

Similarly, a Formula 1 example involving perillyl alcohol showed the same trend with an inflammation suppression score of 43% (for the parent "free" terpene) while its carbamate conjugate with vanillylamine (NDH4498) showed an enhanced suppression of 53% (CEES) and 76% (TPA). This carbamate showed an $IC_{50}$ for inhibition of fatty acid amide hydrolase (FAAH) of 14 µM.

The Formula 2 conjugates (vanilloid-polyamine-vanilloid) can be illustrated by the construct of eugenol-spermidine-eugenol (NDH4635) which displays an inflammation suppression of 73% (CEES-induced inflammation) and zingerone-spermidine-zingerone

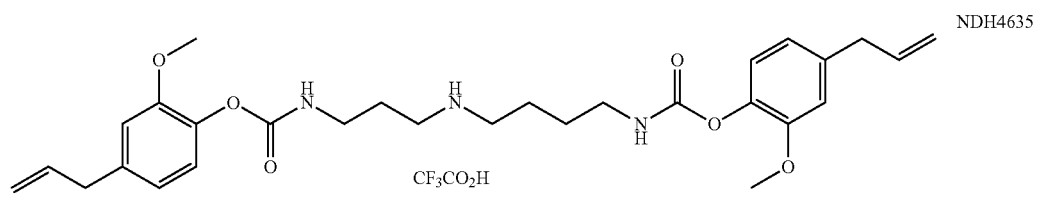 [SMILES: C=CCc1ccc(OC(=O)NCCCCNCCCNC(=O)Oc2ccc(CC=C)cc2OC)c(OC)c1 ; "CF3CO2H"]
NDH4635

(NDH4637) which displays an 89% suppression against CEES-induced and 93% suppression against TPA-induced inflammation. The salt is needed to slow hydrolytic release of the zingerone.

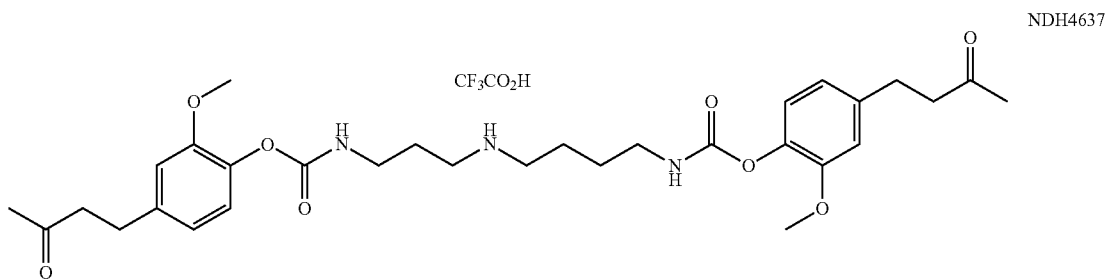 [SMILES: COc1cc(CCC(C)=O)ccc1OC(=O)NCCCCNCCCNC(=O)Oc1ccc(CCC(C)=O)cc1OC ; "CF3CO2H"]
NDH4637

A tri-functional conjugate, NDH4486, (a Formula 3 example), in which the terpene geraniol (35% inflammation suppression score as unconjugated terpene molecule) was linked to the amino acid valine by a carbamate linkage and thence to the vanilloid vanillylamine, proved especially potent (91%) in suppression of TPA-induced inflammation in the mouse ear.

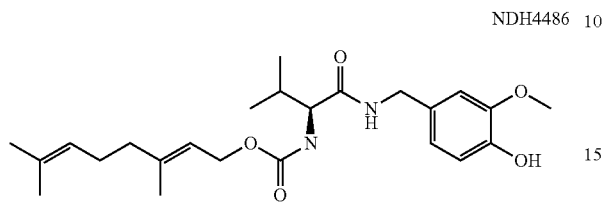

NDH4486

As an example of the Formula 4 conjugates, when carvacrol was linked as a bis-derivative to the well-known polyamine, spermidine, the inflammation suppression of the combined moiety increased to 71% against CEES-induced and 110% against TPA induced inflammatory injury (see NDH4593 shown below). The naturally occurring polyamines such as putrescine, spermidine, and spermine can display anti-inflammatory effects either as free molecular entities or as conjugates with all trans-retinoic acid. These effects are clearly augmented by attachment to terpenes through carbamate linkages.

NDH4593

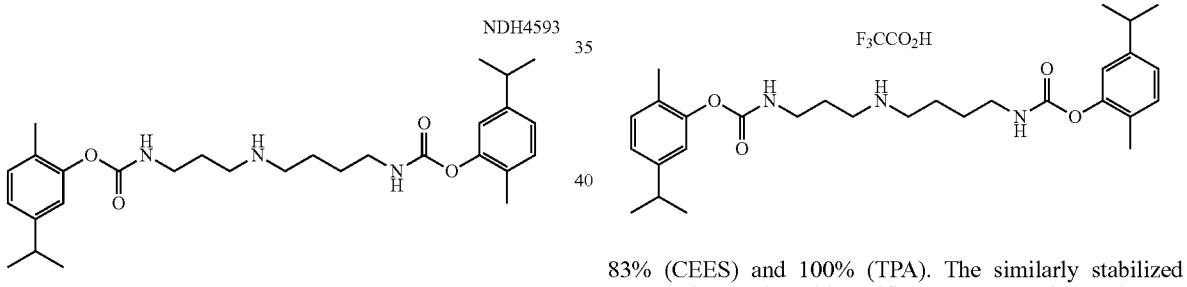

In addition, in a Formula 4 example, thymol displayed an inflammation suppression score of 14% while its carbamate conjugate with spermidine (NDH4590) showed an impressive and complete inflammation suppression of 100% against either CEES or TPA-induced injury.

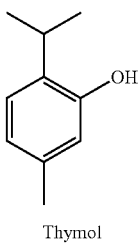

Thymol

NDH4590

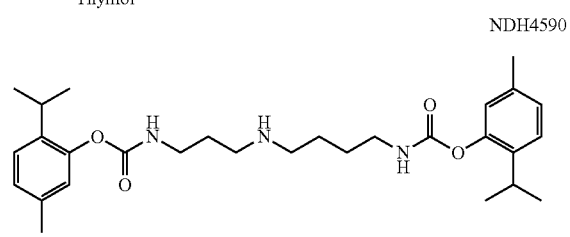

Slower to hydrolyze and to liberate the terpene moiety are the trifluoroacetate salts or amides as exemplified by the carvacrol-spermidine conjugate, NDH4622, with

NDH4622

$F_3CCO_2H$

83% (CEES) and 100% (TPA). The similarly stabilized carvacrol-spermine bis trifluoroacetate salt conjugate, NDH4631, was assayed with 84% (CEES) and 89% (TPA) values.

NDH4631

2 $F_3CCO_2H$

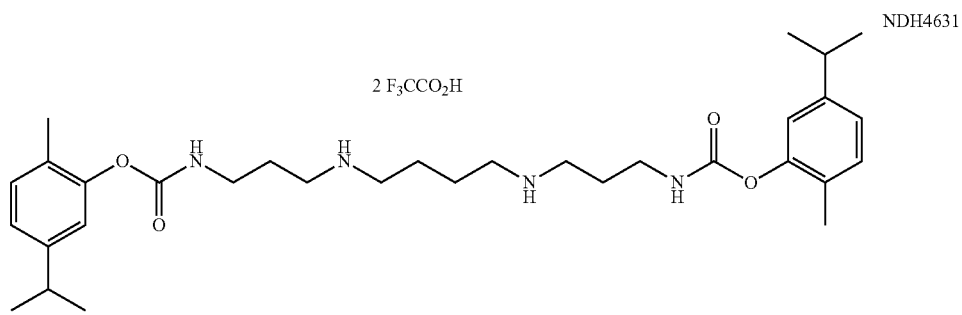 [SMILES: Cc1ccc(C(C)C)cc1OC(=O)NCCCNCCCCNCCCNC(=O)Oc1cc(C(C)C)ccc1C]

The covalently-attached trifluoroacetyl (as an amide) yields a very stable thymol-spermidine conjugate, NDH4616, which retained considerable anti-inflammatory activity, 76% (TPA).

NDH4616

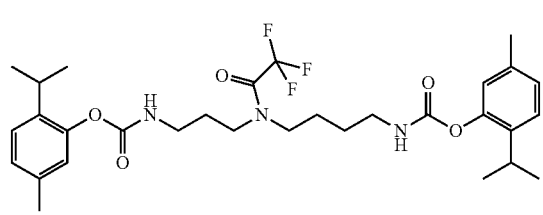

As an example of a Formula 5 compound, NDH4483 links two vanilloid units (vanillyl alcohol and vanillylamine) to a core valine unit. The inflammation suppression was 67% (TPA) and the FAAH $IC_{50}$ was 1.0 mM. The hydrolysis half-life without the acetyl group attached to the para-hydroxyl of the vanillyl alcohol moiety was under 5 minutes in physiological saline.

NDH4483

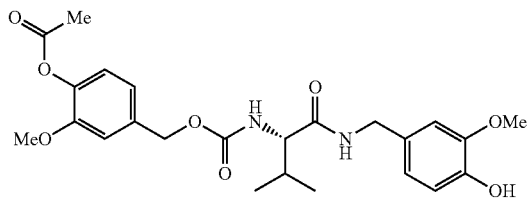

A modification of this Formula 5 compound in which the vanillylamine portion has been deleted (NDH4481) had the same hydrolytic instability—unless the p-hydroxyl group was acetylated—

NDH4481

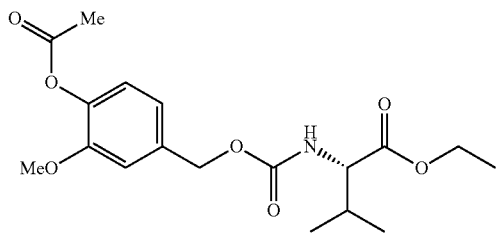

and possessed the same FAAH $IC_{50}$ of 1.0 mM but with a slightly improved inflammation suppression of 72% (CEES-induced) and 93% (TPA-induced).

As an example of a Formula 6 compound, NDH 4648 joins the terpene carvacrol to the amino acid valine by a carbamate bond and thence joins the terpene farnesol to that same amino acid by an ester bond.

NDH4648

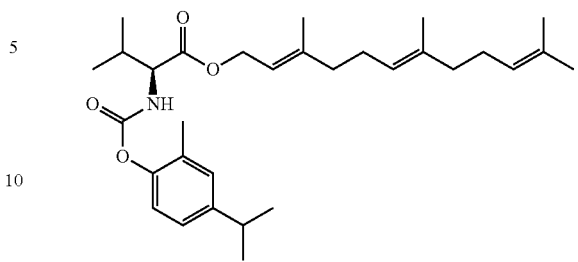

As an example of a Formula 7 compound, NDH 4486 links the terpene geraniol to the amino acid valine by a carbamate bond and thence joins the vanilloid vanillylamine to that same amino acid by an amide bond. The resulting conjugate showed an inflammation suppression of 91% (TPA-induced).

NDH4486

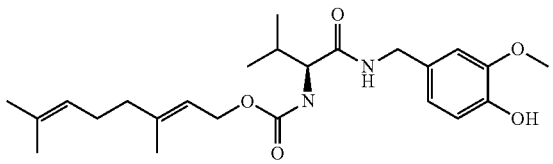

Aspect I Synthesis

The compounds of the invention were synthesized by the pathways outlined in Schemes 1, 2, 3, 4, and 5, using the application of a thiazolide to transfer the —COOR unit to the polyamine, amine, or amino acid unit. The activated thiazoline is synthesized as shown in Scheme 2 if the terpene being transferred has a secondary hydroxyl group, otherwise the pathway as shown in Scheme 1 is suitable. Scheme 3 shows the transfer pathway for —COOR moiety to the polyamines; similar chemistry applies for transfer to amino acids. Scheme 3 shows how the internal secondary NH in the polyamine can have its nucleophilicity suppressed by salt formation or acetamide formation in order to prevent auto-decomposition. Scheme 4 shows how terpene and/or vanilloid moieties are transferred to an amino acid platform compound. Scheme 5 shows how terpene moieties are directly linked to vanilloid moieties (vanillylamine as example) to generate conjugates of Formula 1.

Specific examples selected from the seven Formulae of conjugates have been presented herein but these do not represent the limits of the structural possibilities. Table 1 provides examples of a wider range of synthetic targets obtainable by the experimental methods described herein and consistent with the seven Formulae of conjugates disclosed herein. Systematic names are provided for these anti-inflammatories. Table 1 includes the compounds discussed herein.

Scheme 1. Synthesis of N-alkyloxycarbonyl thiazolidine-2-thiones from 1° alcohols and N-aryloxycarbonyl thiazolidine-2 thiones from phenols: (R = terpene and/or vanilloid moiety). Suitable for alcohol moiety such as geraniol; suitable for phenol moieties such as carvacrol, thymol, eugenol, zingerone and paradol.

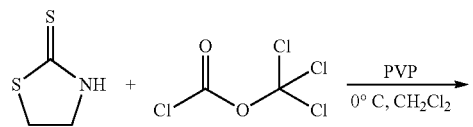

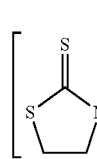

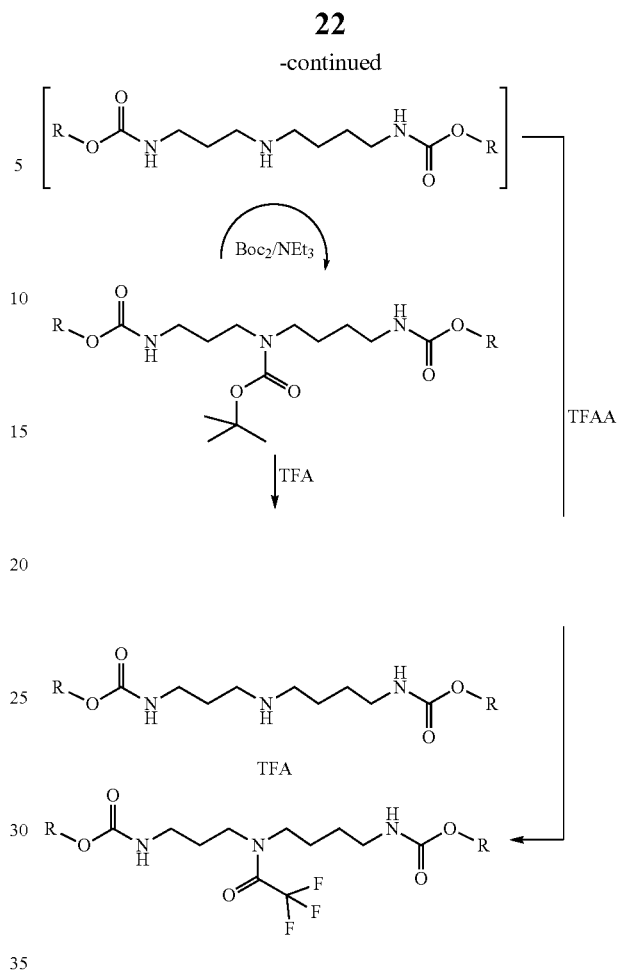

Scheme 2. Synthesis of N-alkyloxycarbonyl thiazolidine-2 thiones from 2° alcohols: (R = terpene and/or vanilloid moiety). Suitable for alcohol moiety such as barneol.

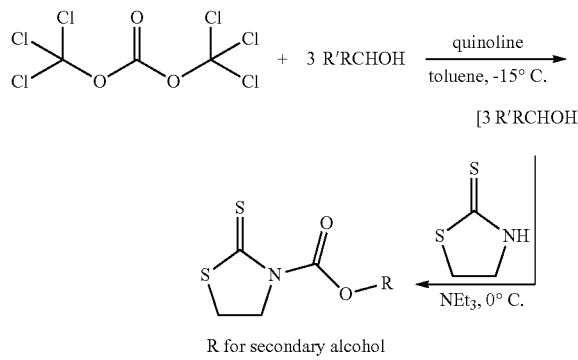

R for secondary alcohol

Scheme 4. Synthesis of amino acid conjugates: (R = terpene and/or vanilloid moiety)

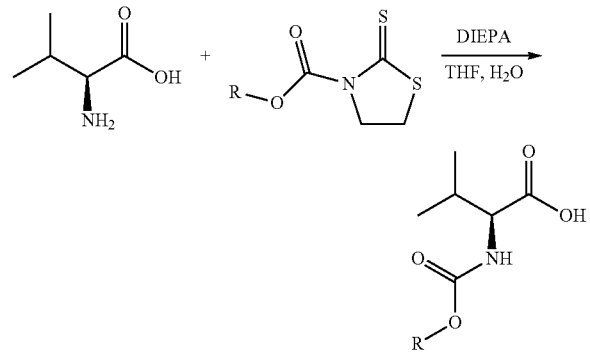

Scheme 3. Synthesis of salts and acetamides of polyamine conjugates: (R = terpene and/or vanilloid moiety)

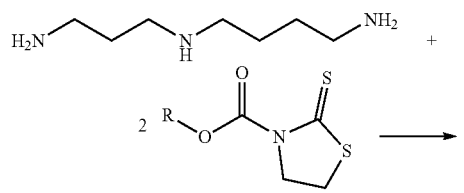

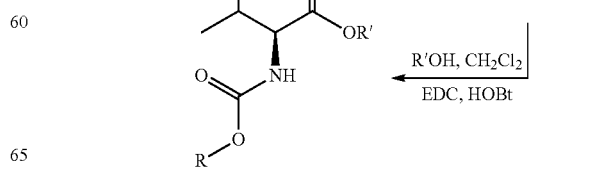

Scheme 5. Synthesis of direct vanilloid-to-terpene conjugates of Formula 1 employing vanillylamine as the model vanilloid

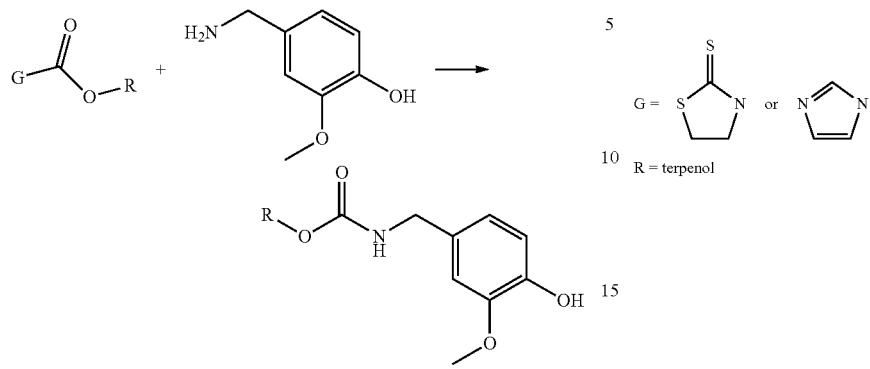

R = terpenol

TABLE 1

Structural diversity consistent with the formulae of Aspect I conjugates of the invention

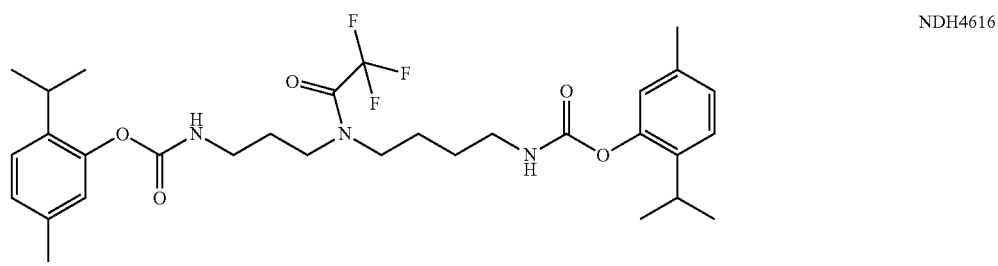

NDH4616

5-methyl-2-(propan-2-yl)phenyl [3-(trifluoroacetyl{4-[(5-methyl-2-(propan-2-yl)phenoxycarbonyl)amino]butyl}amino)propyl]carbamate

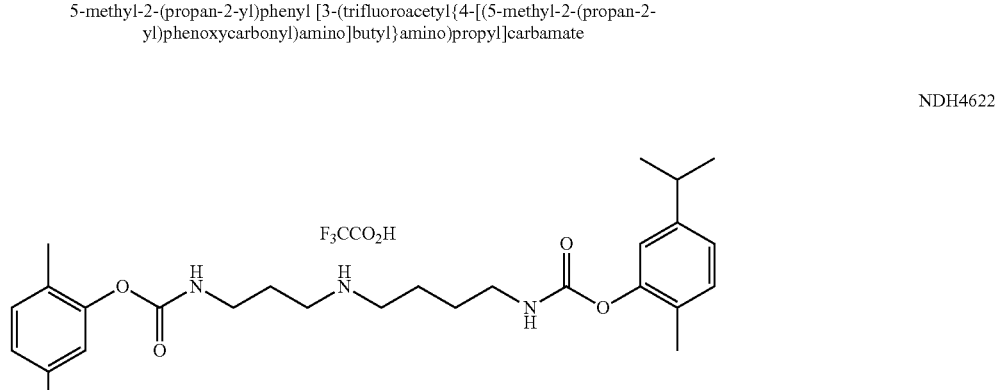

NDH4622

2-methyl-5-(propan-2-yl)phenyl [3-({4-[(2-methyl-5-(propan-2-yl)phenoxycarbonyl)amino]butyl}amino)propyl]carbamate trifluoroacetic acid salt

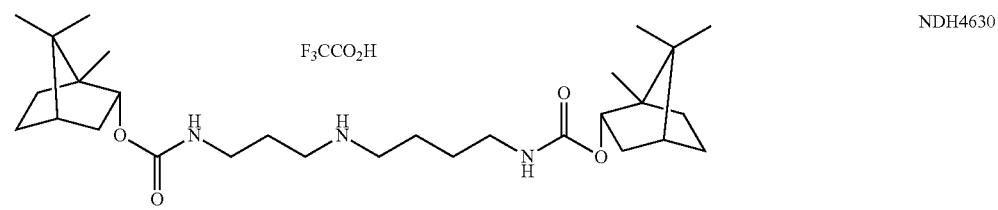

NDH4630

1,7,7-trimethylbicyclo[2.2.1]hept-2-yl [3-({4-[(1,7,7-trimethylbicyclo[2.2.1]hept-2-yl oxycarbonyl)amino]butyl}amino)propyl]carbamate trifluoroacetic acid salt TABLE 1-continued Structural diversity consistent with the formulae of Aspect I conjugates of the invention

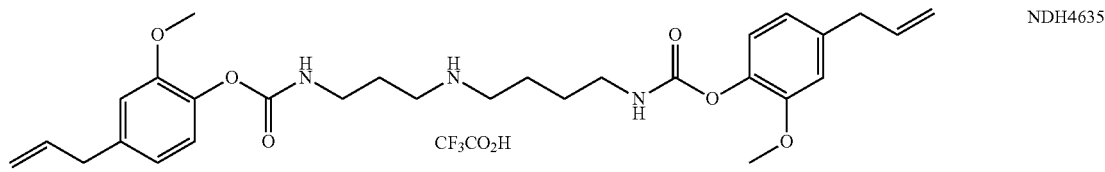

NDH4635

2-methoxy-4-(prop-2-en-1-yl)phenyl [3-({4-[(2-methoxy-4-(prop-2-en-1-yl)phenoxycarbonyl)amino]butyl}amino)propyl]carbamate trifluoroacetic acid salt

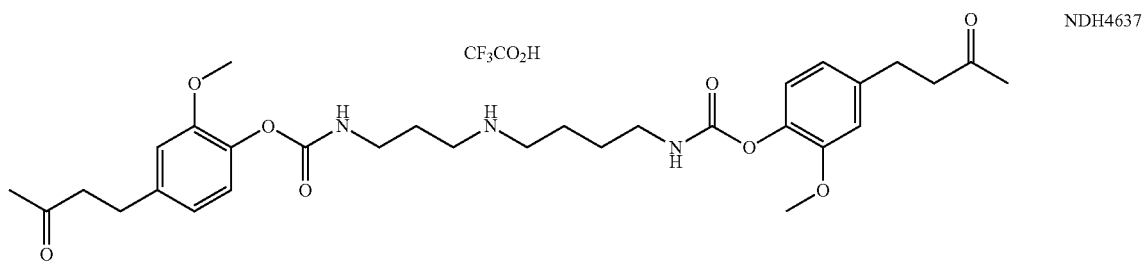

NDH4637

2-methoxy-4-(3-oxobutyl)phenyl [3-({4-[(2-methoxy-4-(3-oxobutyl)phenoxycarbonyl)amino]butyl}amino)propyl]carbamate trifluoroacetic acid salt

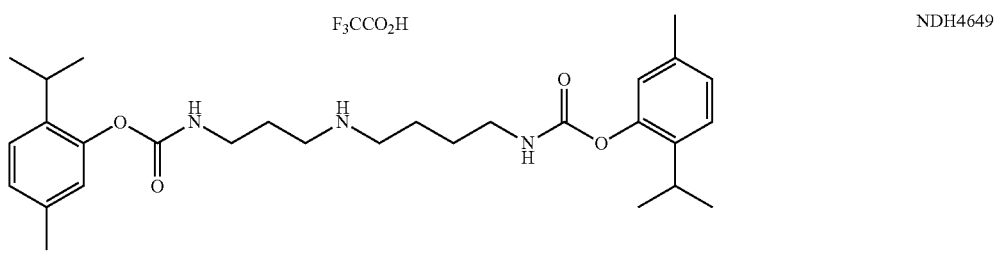

NDH4649

5-methyl-2-(propan-2-yl)phenyl [3-({4-[(5-methyl-2-(propan-2-yl)phenoxycarbonyl)amino]butyl}amino)propyl]carbamate trifluoroacetic acid salt

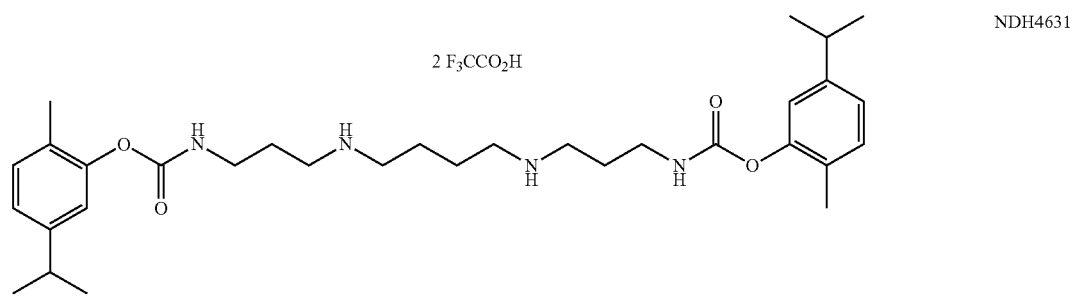

NDH4631 bis(5-isopropyl-2-methylphenyl) ((butane-1,4-diylbis(azanediyl))bis(propane-3,1-diyl))dicarbamate

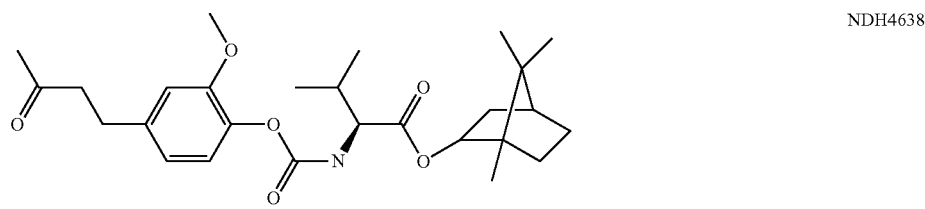

NDH4638

(S)-(1R,2R,4S)-1,7,7-trimethylbicyclo[2.2.1]heptan-2-yl 2-(((2-methoxy-4-(3-oxobutyl)phenoxy)carbonyl)amino)-3-methylbutanoate TABLE 1-continued Structural diversity consistent with the formulae of Aspect I conjugates of the invention

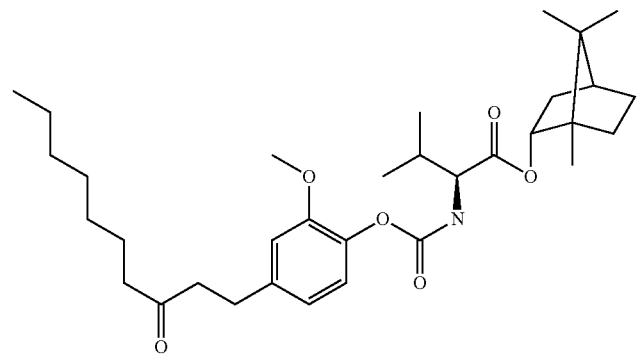

NDH4639

(S)-(1R,2R,4S)-1,7,7-trimethylbicyclo[2.2.1]heptan-2-yl 2-(((2-methoxy-4-(3-oxodecyl)phenoxy)carbonyl)amino)-3-methylbutanoate

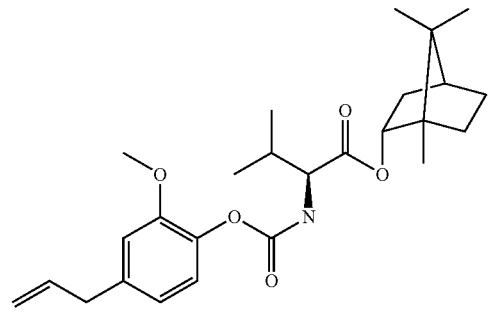

NDH4640

(S)-(1R,2R,4S)-1,7,7-trimethylbicyclo[2.2.1]heptan-2-yl 2-(((4-allyl-2-methoxyphenoxy)carbonyl)amino)-3-methylbutanoate

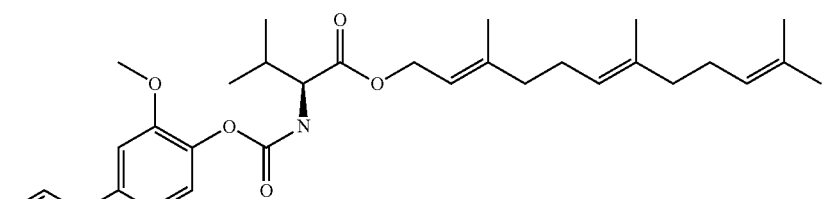

NDH4641

(S)-(2E,6E)-3,7,11-trimethyldodeca-2,6-10-trien-1-yl 2-(((4-allyl-2-methoxyphenoxy)carbonyl)amino)-3-methylbutanoate

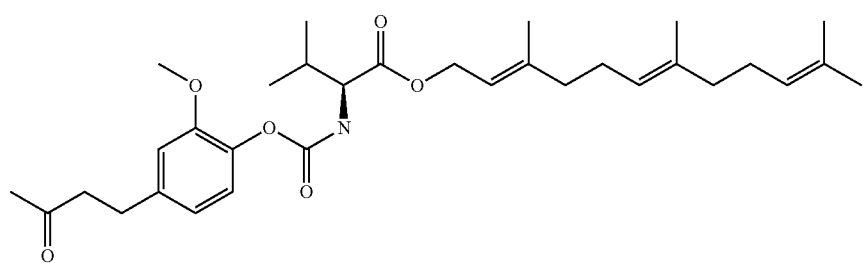

NDH4642

(S)-(2E,6E)-3,7,11-trimethyldodeca-2,6-10-trien-1-yl 2-(((2-methoxy-4-(3-oxobutyl)phenoxy)carbonyl)amino)-3-methylbutanoate TABLE 1-continued Structural diversity consistent with the formulae of Aspect I conjugates of the invention

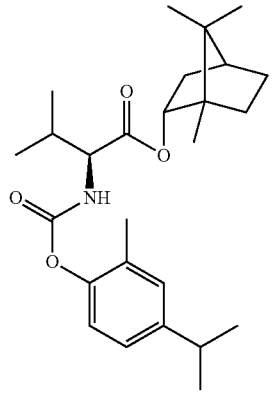

NDH4647

(S)-(1R,2R,4S)-1,7,7-trimethylbicyclo[2.2.1]heptan-2-yl 2-(((4-isopropyl-2-methylphenoxy)carbonyl)amino)-3-methylbutanoate

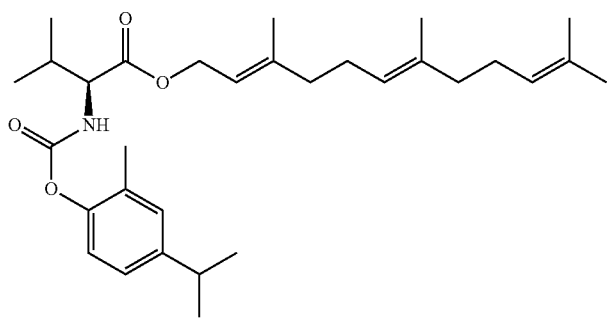

NDH4648

(S)-(2E,6E)-3,7,11-trimethyldodeca-2,6,10-trien-1-yl 2-(((4-isopropyl-2-methylphenoxy)carbonyl)amino)-3-methylbutanoate

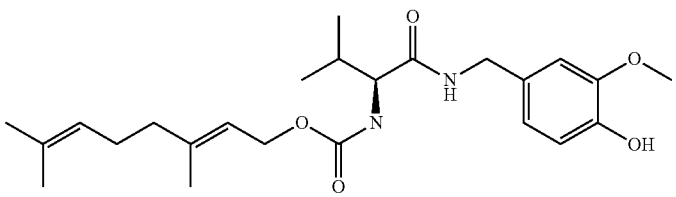

NDH4486

(S,E)-3,7-dimethylocta-2,6-dien-1-yl (1-((4-hydroxy-3-methoxybenzyl) amino)-3-methyl-1-oxobutan-2-yl)carbamate Preparation of Trifluoroacetic Acid Salts of Polyamines A) Formation of Protected Carbamates

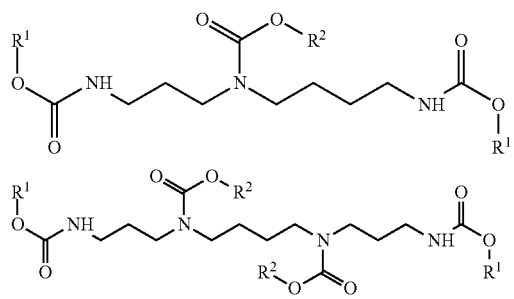

General Procedure
(NDH4616, 4622, 4630, 4631, 4635, 4637 and 4649)

The polyamine (spermidine or spermine) was weighed into a round bottom flask containing a stirring bar. The amine was dissolved in dry dichloromethane (CH$_2$Cl$_2$) (10 mL/mmol). To the stirred solution at room temperature were added two equivalents of an alkyl or aryl 2-thioxo-1,3-thiazolidine-3-carboxylate (hereafter referred to as a thiazolidine carbamate) which rendered a yellow solution. The progress of the reaction was monitored by the loss of the yellow color as well as by TLC which revealed the release of 2-mercaptothiazoline (MTA) and the disappearance of the thiazolidine carbamate. After the first step was complete triethylamine (1 equivalent) was added to the reaction flask followed by the addition of Boc anhydride (Boc$_2$) (1 equivalent). Once the second step was complete, as noted by TLC, the reaction solution was diluted with CH$_2$Cl$_2$, and the resulting solution was extracted with 1N HCl and then saturated NaCl. The organic layer was dried over MgSO$_4$ (anhydrous), filtered, concentrated on the rotary evaporator and dried under vacuum. The crude material was covered with a solution of 7:3, hexanes/ethyl acetate (EtOAc) in order to crystallize out the released MTA. The supernatant was drawn off and concentrated. The product was purified by column chromatography on silica gel eluting with 7:3, hexanes/EtOAc.

1. NDH 4622: $R_f$=0.32 (7:3, hexanes/EtOAc); Yield=76%.
2. NDH 4630: $R_f$=0.39 (7:3, hexanes/EtOAc); Yield=57%.
3. NDH 4649: $R_f$=0.27 (7:3, hexanes/EtOAc); Yield=63%.
4. NDH 4631: Removal of MTA from the crude material was accomplished using 3:2, hexanes/EtOAc. Column purification was carried out using 96:4, $CH_2Cl_2$/acetone as eluant. $R_f$=0.25 (96:4, $CH_2Cl_2$/acetone); Yield=83%.
5. NDH 4635: The crude material was purified by column chromatography, without removing MTA, first using 98:2, $CH_2Cl_2$/MeOH and for the second column 96:4, $CH_2Cl_2$/acetone. $R_f$=0.21 (96:4, $CH_2Cl_2$/acetone): Yield=77%.
6. NDH 4637: The crude material was purified by column chromatography, without removing MTA, using a gradient of 94:6, $CH_2Cl_2$/acetone to 9:1, $CH_2Cl_2$/acetone and then 97:3, $CH_2Cl_2$/MeOH. $R_f$=0.06 (95:5, $CH_2Cl_2$/acetone); Yield=100%.
7. NDH 4616: Upon completion of the first step, 1.5 equivalents of ethyl trifluoroacetate were added in place of the $Boc_2$ and triethylamine, and the reaction mixture was stirred overnight. The product crystallized out of the reaction, and was collected by suction filtration and rinsed with $CH_2Cl_2$. Exact mass (ESI) calculated for $C_{29}H_{44}N_3O_4$ [M+H] 498.3326 found 498.3334. The exact mass represents the compound resulting from loss of the trifluoroacetyl group. $R_f$=0.70 (9:1, $CH_2Cl_2$/MeOH): mp=190-191° C.; Yield=51%.

B) Formation of Trifluoroacetic Acid (TFA) Salts

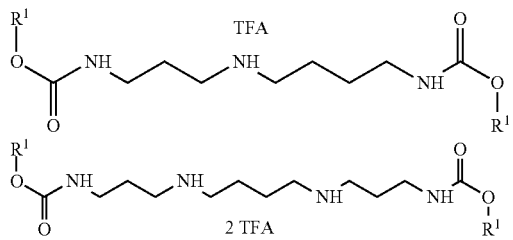

General Procedure
(NDH4616, 4622, 4630, 4631, 4635, 4637 and 4649)

The Boc-containing protected carbamate was dissolved in anhydrous $CH_2Cl_2$ (20 mL/mmol). Trifluoroacetic acid (4 mL/mmol) was added at room temperature. The reaction solution was stirred, and the progress of the reaction was monitored by TLC (7:3, hexanes/EtOAc). The deprotection was complete in 1-2 h. The volatiles were removed by distillation employing an aspirator vacuum. The residue was frozen on liquid $N_2$ and dried under high vacuum. The dry product was covered with diisopropyl ether and the solid that separated was triturated and collected by suction filtration.

1. NDH 4622: Exact mass (ESI) calculated for $C_{29}H_{44}N_3O_4$ [M+H] 498.3326, found 498.3334. White powder; Yield=68%.
2. NDH 4631: Exact mass (ESI) calculated for $C_{32}H_{51}N_4O_4$ [M+H] 555.3905, found 555.3896. White solid; Yield=72%.
3. NDH 4649: Exact mass (ESI) calculated for $C_{29}H_{44}N_3O_4$ [M+H] 498.3326, found 498.3324. White solid; Yield=95%.
4. NDH 4630: Exact mass (ESI) calculated for $C_{29}H_{52}N_3O_4$ [M+H] 506.3952, found 506.3973. Viscous oil; Yield=100%.
5. NDH 4635: The reaction was monitored by using 98:2, $CH_2Cl_2$/MeOH as the TLC solvent. The crude residue was covered with diethyl ether and triturated in order to isolate the pure product. Exact mass (ESI) calculated for $C_{29}H_{40}N_3O_6$ [M+H] 526.2912, found 526.2944. White powder; Yield=88%.
6. NDH 4637: The reaction was monitored using 96:4, $CH_2Cl_2$/acetone as the TLC solvent. The crude residue was covered with diethyl ether and triturated in order to isolate the pure product. Exact mass (ESI) calculated for $C_{31}H_{44}N_3O_8$ [M+H] 586.3123, found 586.3141. White solid; Yield=85%.

NMR Data

1) NDH 4622

$^1$HNMR (methanol-$d_4$) δ: 7.14-7.10 (m, 2H, 2xArH-3), 7.02-6.98 (m, 2H, 2xArH-4), 6.88-6.83 (m, 2H, 2xArH-6), 3.22 (bt, 2H, $HNCH_2CH_2CH_2N$), 3.11-3.02 (m, 4H, $CH_2NHCH_2$), 2.89-2.81 (m, 2H, $2xHC(CH_3)_2$), 2.15-2.11 (overlapping singlets, 6H, 2xAr-$CH_3$), 1.97-1.89 (m, 2H, $NHCH_2CH_2CH_2NH$), 1.79-1.69 (m, 2H, $NHCH_2CH_2CH_2$—$CH_2NHCO$), 1.69-1.60 (m, 2H, $NHCH_2CH_2CH_2CH_2NHCO$), and 1.22-1.18 (overlapping doublets, 12H, $^3J$=6.9 Hz, $2xArCH(CH_3)_2$). Note: The protons $OCHNCH_2CH_2CH_2NH$ are masked beneath the methanol-$d_4$ $CH_3$ peak centered at δ3.30.

2) NDH 4630

$^1$HNMR (CDCl$_3$+D$_2$O) δ: 3.31 (bt, 2H, $OCHNCH_2CH_2CH_2NH$), 3.17 (t, 2H, $^3J$=6.70 Hz, $NHCH_2CH_2CH_2CH_2NHCO$), 3.05-2.92 (m, 4H, $CH_2NHCH_2$), 2.36-2.24 (m, 2x1H, 3-H exo), 1.98-1.90 (m, 2H, $NHCH_2CH_2CH_2NH$), 1.90-1.55 (m, 10H, $NHCH_2CH_2CH_2CH_2NHCO$, 2xbornyl H-4, 2xbornyl H-5 exo and 2xbornyl H-6 endo), 1.30-1.16 (m, 4H, 2xbornyl H-5 endo and 2xbornyl H-6 exo), 1.00-0.94 (m, 2H, 2xbornyl H-3 endo), 0.88-0.86 (bd, 6H, 2xbornyl C-7 $CH_3$), 0.85-0.83 (bd, 6H, 2xbornyl C-7 $CH_3$) and 0.81 (bs, 6H, 2xbornyl C-1 $CH_3$). Note: The bornyl C-2 protons are masked beneath the D$_2$O peak.

3) NDH 4631

$^1$HNMR (methanol-$d_4$) δ: 7.16-7.10 (bd, 2H, 2xArH-3), 7.04-6.98 (m, 2H, 2xArH-4), 6.89-6.84 (bd, 2H, 2xAr-6), 3.11-2.99, (m, 8H, $CH_2NCH_2CH_2CH_2CH_2NCH_2$), 2.90-2.81 (m, 2H, $2xCH(CH_3)_2$), 2.14 (bs, 6H, 2xArCH$_3$), 1.97-1.89 (m, 4H, $2xNCH_2CH_2CH_2N$), 1.80-1.72 (m, 4H, $NCH_2CH_2CH_2CH_2N$), and 1.21 (bd, 12H, $^3J$=6.95 Hz, $2xHC(CH_3)_2$). Note: The protons $2xOCNHCH_2$ are masked beneath the methanol-$d_4$ $CH_3$ peak centered at δ3.30.

4) NDH 4635

$^1$HNMR (methanol-$d_4$) δ: 6.98-6.90 (2 sets of doublets, 2H, $^3J$=8.0 and 8.05 Hz, 2xArH-6), 6.90-6.84 (2 sets of doublets, 2H, $^4J$=1.65 Hz, 2xArH-3), 6.79-6.71 (m, 2H, 2xArH-5), 60.1-5.90 (m, 2H, $2xCH_2$=CH), 5.12-5.01 (m, 4H, $2xCH_2$=CH), 3.80 (s, 3H, Ar-OCH$_3$), 3.78 (s, 3H, Ar-OCH$_3$), 3.36 (overlapping doublets, 4H, $^3J$=6.65 Hz, $2xArCH_2$—CH=$CH_2$), 3.22-3.16 (m, 2H, $NHCH_2CH_2CH_2CH_2NHCO$), 3.12-3.00 (m, 4H, $CH_2NHCH_2$), 1.97-1.87 (m, 2H, $NCH_2CH_2CH_2N$), 1.80-1.68 (m, 2H, $NHCH_2CH_2CH_2CH_2NHCO$), and 1.67-1.57 (m, 2H, $NHCH_2CH_2CH_2CH_2NHCO$). Note: The protons $OCHNCH_2CH_2CH_2NH$ are masked beneath the methanol-$d_4$ $CH_3$ peak centered at δ3.30.

5) NDH 4637

¹HNMR (methanol-d₄) δ: 6.96-6.87 (m, 4H, 2xArH-3 and 2xArH-6), 6.80-6.73 (m, 2H, 2xArH-5), 3.84-3.74 (m, 6H, 2xAr—OCH₃), 3.21-3.14 (m, 2H, OCHNCH₂CH₂CH₂NH), 3.12-3.00 (m, 4H, CH₂NHCH₂), 2.88-2.76 (m, 8H, 2xArCH₂CH₂CO), 2.12-2.11 (overlapping singlets, 6H, 2xCOCH₃), 1.96-1.85 (m, 2H, NCH₂CH₂CH₂N), 1.79-1.68 (m, 2H, NHCH₂CH₂CH₂CH₂NHCO) and 1.67-1.58 (m, 2H, NHCH₂CH₂CH₂CH₂NHCO). Note: The protons OCHNCH₂CH₂CH₂NH are masked beneath the methanol-d₄ CH₃ peak centered at δ3.30.

6) NDH 4649

¹HNMR (methanol-d₄) δ: 7.24-7.13 (m, 2H, ArH-3), 7.06-6.95 (m, 2H, ArH-4), 6.86-6.75 (m, 2H, ArH-6), 3.25-3.21 (m, 2H, NHCH₂CH₂CH₂CH₂NHCO), 3.13-2.98 (m, 6H, 2xCH(CH₃)₂ and CH₂NHCH₂), 2.30 (bs, 6H, 2xArCH₃), 1.99-1.88 (m, 2H, NCH₂CH₂CH₂N), 1.82-1.70 (m, 2H, NHCH₂CH₂CH₂CH₂NCO) and 1.70-1.60 (m, 2H, NHCH₂CH₂CH₂CH₂NCO). Note: The protons OCNCH₂CH₂CH₂NH are masked beneath the methanol-d₄ CH₃ peak centered at δ3.30.

7) NDH 4616

¹HNMR (acetone-d₆) δ: 7.22 (bs, 2H (partially exchanged), 2xNH), 7.17 (apparent triplet, 2H, ³J=7.4 Hz, 2xArH-3), 6.98 (apparent triplet, 2H, ³J=7.8 Hz, 2xArH-4), 6.87 (s, 1H, ArH-6), 6.84 (s, 1H, ArH-6), 3.41-3.35 (m, 2H, HNCH₂CH₂CH₂N), 3.28-3.16 (m, 6H, NHCH₂CH₂CH₂NCH₂CH₂CH₂NH), 3.10-3.04 (m, 2H, Ar—CH(CH₃)₂), 2.08 (m, 2H, HNCH₂CH₂CH₂N), 1.93-1.84 (m, 2H, —NCH₂CH₂CH₂CH₂NH—), 1.72-1.65 (m, 2H, —NCH₂CH₂CH₂CH₂NH—) and 1.20-1.12 (overlapping doublets, 12H, ³J=6.85 Hz, 2xArCH(CH₃)₂).

Preparation of Valine-Based Compounds

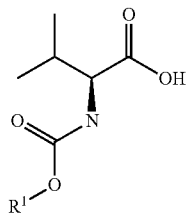

Carbamate formation

A flask containing a stirring bar was charged with the N-acyl thiazolidine-2-thione (1 eq) and L-valine (1.05 eq). To the flask was added THF (5 mL/mmol of the N-acyl thiazolidine-2-thione), and the mixture was stirred until all the N-acyl thiazolidine-2-thione dissolved. Water (5 mL/mmol) was then added followed by N,N-diisopropylethylamine (2 eq), and the resulting two-phase system was stirred vigorously at room temperature. The progress of the reaction was monitored by TLC (9:1, CH₂Cl₂/MeOH, v/v) and by the disappearance of the yellow color originating from the N-acyl thiazolidine-2-thione. When the reaction was complete, the solution was diluted with CH₂Cl₂ and extracted with 1N HCl. The organic layer was concentrated on the rotary evaporator, the residue taken up in Et₂O, and the resulting ether layer was extracted with saturated NaHCO₃. The aqueous layer was then washed with Et₂O. The aqueous phase was acidified to pH=2-3 with 4N HCl. The resulting mixture was extracted with CH₂Cl₂. The organic layer was dried over MgSO₄ (anhydrous), filtered, concentrated on the rotary evaporator and dried under high vacuum. The product was used in the next step without further purification.

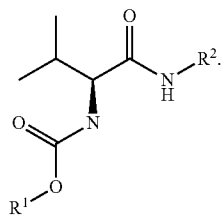

Amide formation

The N-acylated amino acid (1 eq), 1-Hydroxybenzotriazole (HOBt) (1.05 eq) and HMBA hydrochloride (1.05 eq) were placed in a round bottom flask equipped with a stirring bar and fitted with a rubber septum. Dry CH₂Cl₂ (4 mL/mmol) and NEt₃ (1.05 eq) were added under positive N₂ pressure via a syringe through the rubber septum. The flask was immersed in an ice bath, and the reaction mixture was stirred. After sufficient chilling, 1-Ethyl-3-(3-dimethylaminopropyl)carbodiimide (EDC) (1.05 eq) was added in one portion, and the reaction mixture was allowed to stir to room temperature overnight. TLC (96:4, CH₂Cl₂/MeOH, v/v) revealed completion of reaction. The reaction mixture was diluted with CH₂Cl₂ and washed with 1N HCl, H₂O and saturated NaCl. The organic phase was dried over MgSO₄ (anhydrous), filtered and concentrated on the rotary evaporator. The residue was dried under high vacuum, and the crude product was purified by column chromatography on silica gel eluting with 9:1, CH₂Cl₂/acetone, v/v.

NDH 4486: Mp=135-136° C.; R$_f$=0.54 (9:1, CH₂Cl₂/acetone); Yield=68%. Exact mass (ESI) calculated for C₂₄H₃₇N₂O₅ [M+H] 433.2697, found 433.2676.

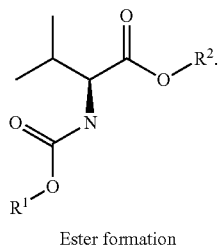

Ester formation

The preparation of esters was carried out as described for amides with the exception of replacing HOBt with 0.2 eq of DMAP. TLC analysis was performed using 7:3, hexanes/EtOAC, v/v while chromatographic purification was carried out using 8:2, hexanes/EtOAC, v/v.

1. NDH 4638: The crude material was purified by column chromatography eluting with 7:3, hexanes/EtOAc. R$_f$=0.27 (7:3, hexanes/EtOAc); Yield=47%. Exact mass (ESI) calculated for C₂₇H₄₀NO₆ [M+H] 474.2850, found 474.2878.

2. NDH 4642: The crude material was purified by column chromatography eluting with 7:3, hexanes/EtOAc. R$_f$=0.32 (7:3, hexanes/EtOAc); Yield=61%. Exact mass (ESI) calculated for C₃₂H₄₈NO₆ [M+H] 542.3476, found 542.3494.

3. NDH 4639: The reaction solution was concentrated, and the residue taken up in EtOAc. The organic layer was extracted with a small amount of water, saturated NaHCO$_3$, water, and finally saturated NaCl. The crude product was purified twice by column chromatography-first eluting with 8:2, hexanes/EtOAc and then 94:6, CH$_2$Cl$_2$/Et$_2$O. R$_f$=0.36 (8:2, hexanes/EtOAc); Yield=24%. Exact mass (ESI) calculated for C$_{33}$H$_{52}$NO$_6$ [M+H] 558.3789, found 558.3809.

4. NDH 4647: The reaction solution was concentrated, and the residue taken up in EtOAc. The organic layer was extracted with a small amount of water, saturated NaHCO$_3$, water, and finally saturated NaCl. The crude material was purified by column chromatography eluting with 8:2, hexanes/EtOAc. R$_f$=0.70 (8:2, hexanes/EtOAc); Yield=43%. Exact mass (ESI) calculated for C$_{26}$H$_{40}$NO$_4$ [M+H] 430.2952, found 430.2968.

5. NDH 4648: The reaction solution was concentrated, and the residue taken up in EtOAc. The organic layer was extracted with a small amount of water, saturated NaHCO$_3$, water, and finally saturated NaCl. The crude material was purified by column chromatography eluting with 8:2, hexanes/EtOAc. R$_f$=0.69 (8:2, hexanes/EtOAc); Yield=62%. Exact mass (ESI) calculated for C$_{31}$H$_{47}$NO$_4$Na [M+Na] 520.3397, found 520.3429.

6. NDH 4640: The reaction solution was concentrated, and the residue taken up in EtOAc. The organic layer was extracted with a small amount of water, saturated NaHCO$_3$, water, and finally saturated NaCl. The crude material was purified by column chromatography eluting with 8:1:1 (CH$_2$Cl$_2$/DIPE/hexanes). R$_f$=0.89 (8:1:1, CH$_2$Cl$_2$/DIPE/hexanes); Yield=57%. Exact mass (ESI) calculated for C$_{26}$H$_{38}$NO$_5$ [M+H] 444.2744, found 444.2750.

7. NDH 4641: The reaction solution was concentrated, and the residue taken up in EtOAc. The organic layer was extracted with a small amount of water, saturated NaHCO$_3$, water, and finally saturated NaCl. The crude material was purified by column chromatography eluting with 8:1:1 (CH$_2$Cl$_2$/DIPE/hexanes). R$_f$=0.92 (8:1:1, CH$_2$Cl$_2$/DIPE/hexanes); Yield=64%. Exact mass (ESI) calculated for C$_{31}$H$_{46}$NO$_5$ [M+H] 512.3370, found 512.3391.

NMR Data

1) NDH 4486

$^1$HNMR (CDCl$_3$) δ6.83 (d, 1H, $^3$J=8.0 Hz, ArH), 6.76 (d, 1H, $^4$J=1.85 Hz, ArH), 6.72 (dd, 1H, $^3$J=8.1 Hz, $^4$J=1.85 Hz, ArH), 6.12 (bs, 1H, amide NH), 5.57 (s, 1H, ArOH), 5.30 (bs, 1H, O—CH$_2$CH=), 5.16 (d, 1H, $^3$J=7.4 Hz, carbamate NH), 5.06 (m, 1H, (CH$_3$)$_2$—C=CH—), 4.60-4.50 (m, 2H, C(O)O—CH$_2$—), 4.41-4.29 (2xdd, 2H, $^2$J=14.5 Hz, $^3$J=5.5 Hz, Ar—CH$_2$—N), 3.93 (dd, 1H, $^3$J$_{NH}$=8.7 Hz, $^3$J$_{CH}$=6.1 Hz, CO—CH), 3.85 (s, 3H, Ar—O—CH$_3$), 2.22-2.10 (m, 1H, CH—(CH$_3$)$_2$), 2.10-2.08 (m, 4H, =C—CH$_2$—CH$_2$—C=), 1.69-1.63 (m, 6H, =(CH$_3$)$_2$), 1.58 (s, 3H, CH$_3$—C=), 0.95 (d, 3H, $^3$J=6.8 Hz, CH(CH$_3$)—CH$_3$) and 0.90 (d, 3H, $^3$J=6.8 Hz, CH(CH$_3$)—CH$_3$). Exact mass (ESI) Calculated for C$_{24}$H$_{37}$N$_2$O$_5$ [M+1] 433.2697, found 433.2676.

2) NDH 4631

$^1$HNMR (methanol-d$_4$) δ7.16-7.10 (bd, 2H, 2xArH-3), 7.04-6.98 (m, 2H, 2xArH-4), 6.89-6.84 (bd, 2H, 2xAr-6), 3.11-2.99, (m, 8H, CH$_2$NCH$_2$CH$_2$CH$_2$CH$_2$NCH$_2$), 2.90-2.81 (m, 2H, 2xCH(CH$_3$)$_2$), 2.14 (bs, 6H, 2xArCH$_3$), 1.97-1.89 (m, 4H, 2xNCH$_2$CH$_2$CH$_2$N), 1.80-1.72 (m, 4H, NCH$_2$CH$_2$CH$_2$CH$_2$N), and 1.21 (bd, 12H, $^3$J=6.95 Hz, 2xHC(CH$_3$)$_2$). Note: The protons 2xOCNHCH$_2$ are masked beneath the methanol-d$_4$ CH$_3$ peak centered at δ3.30.

3) NDH 4638

$^1$HNMR (CDCl$_3$) δ6.97 (d, 1H, $^3$J=8.05 Hz, ArH-6), 6.75 (d, 1H, $^4$J=1.8 Hz, ArH-3), 6.71 (dd, 1H, $^3$J=8.05 Hz, $^4$J=1.8 Hz, ArH-5), 5.60 (d1H, $^3$J=9.05 Hz, NH), 4.90 (bd, 1H, $^3$J=9.55 Hz, bornyl H-2), 4.34 (dd, 1H, $^3$J=8.9 Hz, $^4$J=4.5 Hz, CO—CH), 3.77 (s, 3H, ArOCH$_3$), 2.85 (t, 2H, $^3$J=7.5 Hz, ArCH$_2$CH$_2$CO), 2.73 (t, 2H, $^3$J=7.45 Hz, ArCH$_2$CH$_2$CO), 2.41-2.36 (m, 1H, bornyl H-3exo), 2.27-2.20 (m, 1H, (CH$_3$)$_2$CH), 2.13 (s, 3H, COCH$_3$), 1.94-1.89 (m, 1H, bornyl H-6 endo), 1.78-1.72 (m, 1H, bornyl H-5 exo), 1.68 (t, 1H, J=4.40 Hz, bornyl H-4), 1.37-1.28 (m, 1H, bornyl H-6 exo), 1.25-1.16 (m, 1H, bornyl H-5 endo), 1.02 (d, 3H, $^3$J=6.85 Hz, CH$_3$(CH$_3$)CH—), 0.99-0.94 (m, 4H, bornyl H-3 endo and CH$_3$(CH$_3$)CH—), 0.89 (s, 3H, one bornyl C-7 CH$_3$), 0.87 (s, 3H, one bornyl C-7 CH$_3$) and 0.84 (s, 3H, bornyl C-1 CH$_3$).

4) NDH 4639

$^1$HNMR (CDCl$_3$) δ6.97 (d, 1H, $^3$J=8.05 Hz, ArH-6), 6.75 (d, 1H, $^4$J=1.8 Hz, ArH-3), 6.71 (dd, 1H, $^3$J=8.10 Hz, $^4$J=1.8 Hz, ArH-5), 5.60 (d, 1H, $^3$J=8.95 Hz, NH), 4.91 (bd, 1H, $^3$J=9.60 Hz, bornyl H-2), 4.34 (dd, 1H, $^3$J=8.95 Hz, $^4$J=4.55 Hz, CHCO), 2.84 (t, 2H, $^3$J=7.58 Hz, ArCH$_2$—), 2.69 (t, 2H, $^3$J=7.58 Hz, ArCH$_2$CH$_2$CO—), 2.41-2.34 (m, 3H, bornyl H-3 exo and ArCH$_2$CH$_2$COCH$_2$—), 2.27-2.20 (m, 1H, (CH$_3$)$_2$CH—), 1.94-1.89 (m, 1H, bornyl H-6 endo), 1.78-1.72 (m, 1H, bornyl H-5 exo), 1.68 (t, 1H, $^3$J=4.42 Hz, bornyl H-4), 1.58-1.50 (m, —COCH$_2$CH$_2$(CH$_2$)$_4$CH$_3$ masked beneath D$_2$O peak), 1.36-1.17 (m, 10H, —COCH$_2$CH$_2$(CH$_2$)$_4$CH$_3$, bornyl H-5 endo and bornyl H-6 exo), 1.02 (d, 3H, $^3$J=6.85 Hz, CH$_3$(CH$_3$)CH—), 1.00-0.93 (m, 4H, CH$_3$(CH$_3$)CH— and bornyl H-3 endo) 0.89 (s, 3H, one bornyl C-7 CH$_3$) and 0.86-0.83 (m, 9H, one bornyl C-7 CH$_3$, bornyl C-1 CH$_3$ and —CO(CH$_2$)$_6$CH$_3$).

5) NDH 4640

$^1$HNMR (CDCl$_3$) δ7.01 (d, 1H, $^3$J=7.75 Hz, ArH-6), 6.75 (d, 1H, $^4$J=1.6 Hz, ArH-3), 6.73 (d, 1H, $^3$J=8.05 Hz, ArH-5), 5.97-5.89 (m, 1H, ArCH$_2$CH=CH$_2$), 5.61 (d, 1H, $^3$J=8.95 Hz, NH), 5.10-5.04 (m, 2H, ArCH$_2$CH=CH$_2$), 4.92-4.89 (m, 1H, bornyl H-2), 4.35 (dd, 1H, J$_{NH}$=8.95 Hz, J$_{CH}$=4.55 Hz, —CH(NH)CO—), 3.80 (s, 3H, ArOCH$_3$), 3.34 (d, 2H, J=6.70 Hz, ArCH$_2$CH=CH$_2$), 2.42-2.34 (m, 1H, bornyl H-3 exo), 1.95-1.89 (m, 1H, bornyl H-6 endo), 1.78-1.71 (m, 1H, bornyl H-5 exo), 1.68 (t, 1H, J=4.45 Hz, bornyl H-4), 1.37-1.28 (m, 1H, bornyl H-6 exo), 1.25-1.16 (m, 1H, bornyl H-5 endo), 1.03 (d, 3H, $^3$J=6.90 Hz, CH$_3$(CH$_3$)CH—), 0.99-0.94 (m, 4H, bornyl H-3 endo and CH$_3$(CH$_3$)CH—), 0.89 (s 3H, one bornyl C-7 CH$_3$), 0.86 (s, 3H, one bornyl C-7 CH$_3$) and 0.84 (s, 3H, bornyl C-1 CH$_3$).

6) NDH 4641

$^1$HNMR (CDCl$_3$) δ7.01 (d, 1H, $^3$J=8.0 Hz, ArH-6), 6.74 (d, 1H, $^4$J=1.65 Hz, ArH-3), 6.72 (dd, 1H, $^3$J=8.0 Hz, $^4$J=1.8 Hz, ArH-5), 5.96-5.88 (m, 1H, ArCH$_2$CH=CH$_2$), 5.60 (d, 1H, $^3$J=9.1 Hz, NH), 5.35 (bt, 1H, J=7.15 Hz, —OCH$_2$CH=C—), 5.13-5.03 (m, 4H, ArCH$_2$CH=CH$_2$ and 2 vinyl H of farnesyl chain), 4.72-4.61 (m, 2H, —OCH$_2$CH=C—), 4.33 (dd, 1H, J$_{NH}$=9.15 Hz, J$_{CH}$=4.6 Hz, (CH$_3$)$_2$CHCHCO), 2.25-2.17 (m, 1H, (CH$_3$)$_2$CH—), 2.13-1.93 (m, 8H, 4 allylic —CH$_2$— of farnesyl chain), 1.70 (s, 3H, —OCH$_2$C=C(CH$_3$)—), 1.66 (s, 3H, center CH$_3$ of farnesyl chain), 1.58 (s, 6H, —C=C(CH$_3$)$_2$), 0.996 (d, 3H, $^3$J=6.85 Hz, CH$_3$(CH$_3$) CH—) and 0.917 (d, 3H, $^3$J=6.90 Hz, CH$_3$(CH$_3$)CH—).

7) NDH 4642

$^1$HNMR (CDCl$_3$) δ6.97 (d, 1H, $^3$J=8.0 Hz, ArH-6), 6.75 (d, 1H, $^4$J=1.85 Hz, ArH-3), 6.70 (dd, 1H, $^3$J=8.05 Hz, $^4$J=1.85 Hz, ArH-5), 5.60 (d, 1H, $^3$J=9.1 Hz, NH), 5.34 (m, 1H, —OCH$_2$CH=C—), 5.12-5.04 (m, 2H, 2 vinyl H of farnesyl chain), 4.72-4.60 (m, 2H, —OCH$_2$CH=C—), 4.33 (dd, 1H, J$_{NH}$=9.15 Hz, J$_{CH}$=4.6 Hz, (CH$_3$)$_2$CHCHCO), 3.79 (s, 3H, ArOCH$_3$), 2.84 (t, 2H, $^3$J=7.5 Hz, ArCH$_2$—), 2.73 (t, 2H, $^3$J=7.5 Hz, ArCH$_2$CH$_2$CO—), 2.26-2.17 (m, 1H, (CH$_3$)$_2$CH—), 2.12 (s, 3H, —COCH$_3$), 2.11-1.93 (m, 8H, 4 allylic —CH$_2$— of farnesyl chain), 1.70 (2, 3H, —OCH$_2$CH═C(CH$_3$)—), 1.66 (s, 3H, center CH$_3$ of farnesyl chain), 1.58 (s, 6H, —C═C(CH$_3$)$_2$), 0.99 (d, 3H, $^3$J=6.8 Hz, CH$_3$(CH$_3$)CH—) and 0.91 (d, 3H, $^3$J=6.90 Hz, CH$_3$(CH$_3$)CH—).

8) NDH 4647

$^1$HNMR (CDCl$_3$) δ7.10 (d, 1H, $^3$J=7.75 Hz, ArH-6), 6.97 (dd, 1H, $^3$J=7.70 Hz, $^4$J=1.55 Hz, ArH-5), 6.91 (s, 1H, ArH-3), 5.54 (d, 1H, $^3$J=8.95 Hz, NH), 4.97-4.87 (m, 1H, bornyl H-2), 4.37 (dd, 1H, $^3$J=9.05 Hz and 4.45 Hz, COCH), 2.84 (septet, 1H, $^3$J=6.96 Hz, CH(CH$_3$)$_2$), 2.44-2.35 (m, 1H, bornyl H-3 exo), 2.30-2.21 (m, 1H, (CH$_3$)$_2$CHCH(NH)CO), 2.16 (s, 3H, ArCH$_3$), 1.96-1.88 (m, 1H, bornyl H-6 endo), 1.80-1.72 (m, 1H, bornyl H-5 exo), 1.71-1.67 ((bt, 1H, $^3$J=4.40 Hz, bornyl H-4), 1.37-1.29 (m, 1H, bornyl H-6 exo), 1.22-1.18 (m, 7H, bornyl H-5endo and ArCH(CH$_3$)$_2$), 1.03 (d, 3H, $^3$J=6.85 Hz, CH$_3$(CH$_3$)CHCH(NH)CO), 1.01-0.93 (m, 1H, bornyl H-3 endo), 0.95 (d, 3H, $^3$J=6.95 Hz, CH$_3$(CH$_3$)CHCH(NH)CO), 0.89 (s, 3H, bornyl C-7 CH$_3$), 0.87 (s, 3H, bornyl C-7 CH$_3$) and 0.84 (s, 3H, bornyl C-1 CH$_3$).

9) NDH 4648

$^1$HNMR (CDCl$_3$) δ7.09 (d, 1H, $^3$J=7.75 Hz, ArH-2), 6.97 (dd, 1H, $^3$J=7.75 Hz, $^4$J=1.45 Hz, ArH-3), 6.90 (s, 1H, ArH-5), 5.54 (d, 1H, $^3$J=9.15 Hz, NH), 5.35 (bt, 1H, OCH$_2$—CH═), 5.12-5.04 (m, 2H, 2 vinyl protons), 4.75-4.61 (m, 2H, OCH$_2$—CH═), 4.38-4.32 (dd, 1H, $^3$J=9.18 Hz and $^3$J=4.58 Hz, CH—CO), 2.89-2.86 (septet, 1H, $^3$J=6.86 Hz, ArCH(CH$_3$)$_2$), 2.28-2.18 (m, 1H, (CH$_3$)$_2$CHCH(NH)CO), 2.15 (s, 3H, ArCH$_3$), 2.14-1.93 (m, 8H, 4 CH$_2$ units of fornesyl moiety), 1.71 (s, 3H, O—CH$_2$CH═C(CH$_3$)—), 1.66 (s, 3H, CH$_2$CH$_2$C═C(CH$_3$)CH$_2$—), 1.58 (s, 6H, C═C(CH$_3$)$_2$), 1.20 (d, 6H, $^3$J=6.95 Hz, ArCH(CH$_3$)$_2$), 1.00 (d, 3H, $^3$J=6.85 Hz, CH$_3$(CH$_3$)CHCH(NH)CO) and 0.92 (d, 3H, $^3$J=6.9 Hz, CH$_3$(CH$_3$)CHCH(NH)CO).

Examples of Aspect II

Synergism of anti-inflammatory responses by anti-inflammatory agents covalently coupled to amino acids (Aspect II) was demonstrated by preparation of the S-naproxen—valine conjugate, and screening it in the MEVM against CEES challenge. MEVM is a standard in vivo assay for assessment of anti-inflammatory potential in addressing chemically-induced injury to rodent skin. CEES is one of the inflammation inducers employed in the MEVM assay. A compound of the invention, Formula (IV-acid) (NDH 4476) provided four times better inflammation suppression (44%) than naproxen itself under the same conditions. The corresponding ethyl ester analog (IV-ethyl ester) (NDH 4535) was equipotent but the 3,3-dimethylbutyl ester (IV-3,3-dimethylbutyl-) (NDH 4596) was superior at 52% inflammation suppression. The latter molecule also was an inhibitor of AChE displaying anti-cholinergic activity with an IC$_{50}$ of 18.6 μM.

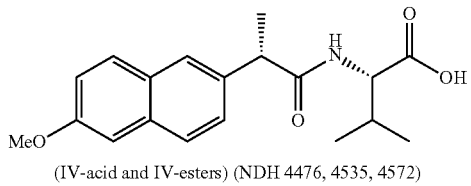 [SMILES: COc1ccc2cc([C@H](C)C(=O)N[C@H](C(=O)O)C(C)C)ccc2c1]

(IV-acid and IV-esters) (NDH 4476, 4535, 4572)

The phenylalanine conjugate of S-naproxen (esterified as the 3,3-dimethylbutyl ester) shown in Formula (V) (NDH 4572) displayed an impressive 83% suppression of CEES-induced inflammation while S-naproxen itself yielded a mere 11% suppression of CEES inflammation. The six-carbon ester not only adds lipophilicity and promotes solubility of the NSAID-amino acid pharmaceutical in ointment excipients, but through its action as a bioisostere of choline it provides anticholinergic activity. For a discussion of how anticholinergic activity can facilitate anti-inflammatory responses see S. C. Young et al, Investigation of anticholinergic and non-steroidal anti-inflammatory prodrugs which reduce chemically-induced skin inflammation, *J. Appl. Tox.*, 2012, 32: 135-141. The choline bioisostere 3,3-dimethylbutyl alcohol provides cholinesterase inhibition in the final anti-inflammatory drug-amino acid-choline bioisostere construct. For the naproxen-phenylalanine platform, Formula (V), (also known as NDH 4572) this choline mimic generates an IC$_{50}$ value of 4.7 μM against AChE.

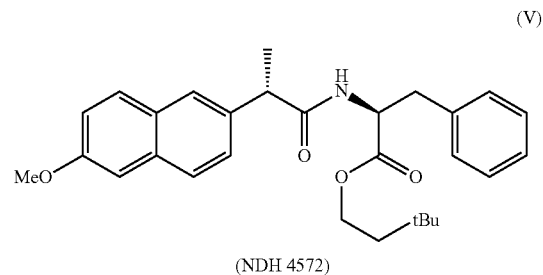 [SMILES: COc1ccc2cc([C@H](C)C(=O)N[C@@H](Cc3ccccc3)C(=O)OCCC(C)(C)C)ccc2c1]

(NDH 4572)

The phenylalanine conjugate of the NSAID diclofenac (esterified as the 3,3-dimethyl-butyl ester; Formula (VI)) (NDH 4578) displayed a complete (100%) suppression of induced inflammation in the mouse. In the same assay diclofenac itself displayed a mere 17% suppression of inflammation.

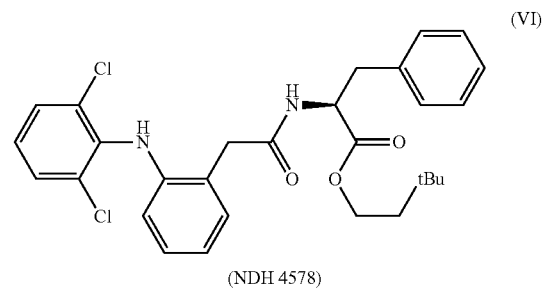 [SMILES: CC(C)(C)CCOC(=O)[C@H](Cc1ccccc1)NC(=O)Cc1ccccc1Nc1c(Cl)cccc1Cl]

(NDH 4578)

Despite the fact that it is an NSAID, topical ibuprofen by itself was found to be a dermal irritant, adding 11% additional inflammation to CEES-induced injury. Furthermore, vanillylamine is only a weak anti-inflammatory; however, the triple conjugate of ibuprofen, vanillylamine, and valine, Formula (VII) (NDH 4479), provided a 94% suppression of CEES-induced inflammation.

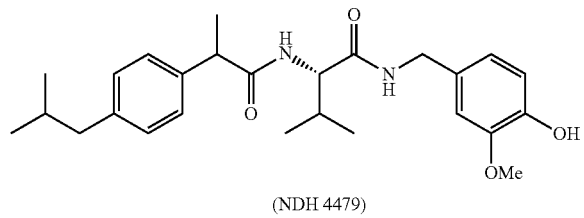

(NDH 4479)

Aspect II: Design and Synthesis of the NSAID-Amino Acid Conjugates and NSAID-Amino Acid—Anticholinergic Conjugates The NSAID-amino acid conjugates (as esters or as free carboxylic acids) were synthesized by the following general method. All NSAIDs employed herein bear a pendant carboxylic acid group. To illustrate how such molecules are linked to the amino acid carrier the designation NSAID-CO— is used to convey that the fundamental ring system of the NSAID is attached through its carboxyl moiety. The required amino acids (0.60 mmol) were first esterified with ethyl alcohol, n-butyl alcohol, or 3,3-dimethylbutyl alcohol in toluene with p-toluenesulfonic acid as a catalyst. The amino acid esters could be isolated, crystallized, and purified in 55-85% yields if so desired. Then the requisite NSAID (0.60 mmol), and HOBt (0.66 mmol) were added in $CH_2Cl_2$ (5 mL) under a nitrogen atmosphere. The reaction contents were stirred at room temperature for 15 min, until the solution became clear. EDC·HCl (1.1 equiv., 126 mg, 0.66 mmol) was then added and the reaction contents were stirred at room temperature overnight (16 hr). Distilled water was added and the organic layer was separated. The aqueous phase was then extracted with methylene chloride (25 mL) and the two organic layers were combined and washed with 1 M HCl (2×50 mL), saturated $NaHCO_3$ (50 mL), and brine. The organic layer was then dried over anhydrous $MgSO_4$, filtered, and concentrated to yield the final product, which was purified via column chromatography using a gradient separation with hexanes (100 to 50%) and ethyl acetate (0 to 50%) as the eluting solvent mixture.

Yields on the amide-forming step were 89-99% and after column chromatography were homogeneous by TLC. These NSAID-amino acid—ester conjugates were sufficiently pure for in vitro (AChE) screening or in vivo (MEVIVI) testing. Hydrolysis of these esters in 1:1 water:THF with 1 mmol of $Na_2CO_3$ could free the carboxylic acids (giving the simple NSAID-amino acid conjugate if so desired) in 40% yield. Products were identified by exact mass spectrometry with experimental values within +/− 0.02 amu of the theoretical mass. In this fashion, on the valine platform, (IV-ethyl ester, NDH 4535) (white solid, mp 135-139° C.) and (IV-3,3-dimethylbutyl ester, NDH 4596) (clear oil Rf=0.30 with 4:1 hexane:ethyl acetate) and (IV-free acid, NDH 4476) (white solid, 164-166° C.) were prepared. While this method is suitable for any NSAID-amino acid or NSAID-amino acid ester, the specific products prepared by this route were NDH 4651, NDH 4652, NDH 4653, and NDH 4654. Scheme I illustrates this pathway with any alcohol (R'—OH) and any carboxyl-bearing NSAID but the method has been specifically applied to these alcohols: ethanol, n-butanol, 3,3-dimethylbutyl alcohol, 2-(trimethylsilyl)ethyl alcohol, and to these NSAIDs: ibuprofen, naproxen, indomethacin, and diclofenac.

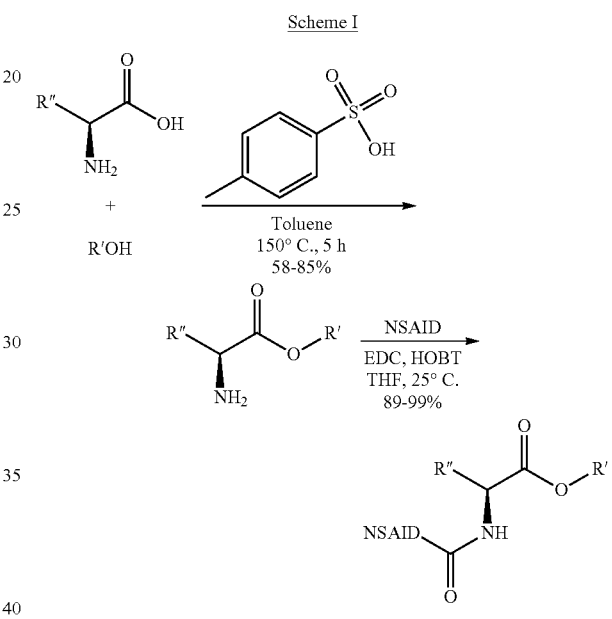

Scheme I

For the proline conjugates, two structurally-related products were observed via nuclear magnetic resonance (NMR) spectroscopy, even following extensive chromatographic purification. In all cases, the percentage of the second product ranged from 13 to 19%, depending on the NSAID. The final products were homogeneous by TLC. It was determined that the sterically hindered proline amide bond undergoes cis-trans isomerization (Scheme II) which can be detected via NMR (vide infra). Cis-trans isomerization of the proline peptide bond is well documented and plays an important role in protein folding.

Scheme II

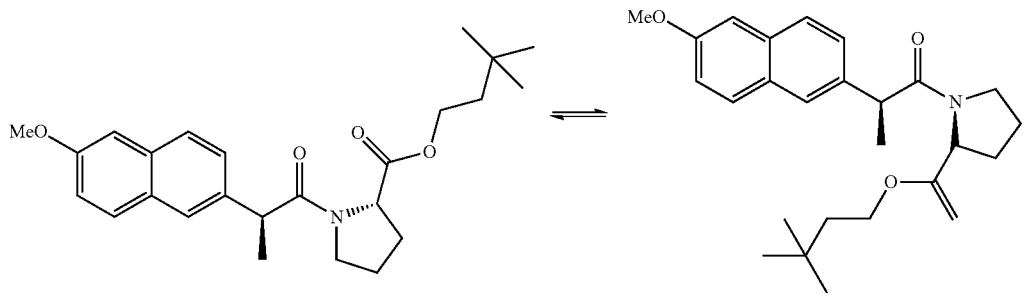

Aspect II: Design and Syntheses of Amino Acid Conjugates Requiring Specialized Transformations A. Preparation of Amino Acid Conjugates which Include a Ketone Body (3-hydroxybutyrate) Illustrated with NDH 4571 as an Example The labile 3-hydroxy group requires protection before it can be linked to an amino acid platform. For this the TBDMS-protected 3-hydroxybutyric acid ((R)-3-[(tert-butyl)dimethylsilyloxy] butanoic acid) was first prepared according to the procedure of D. Seebach, et. al. (Helvetica Chimica Acta, 79(3), 670 (1996)) and used as the starting material. Seebach's protected acid compound was subsequently converted to the thiazolide of the silyl-protected butanoic acid, first structure shown in Scheme III. The protected acid (1.776 g, 8.133 mmol), mercaptothiazoline (970 mg 8.133 mmol), and N,N'-dicyclohexylcarbodiimide (DCC) (1.762 g, 1.05×8.133 mmol) were dissolved in 40 mL of $CH_2Cl_2$. The flask was immersed in an ice bath, and after sufficient chilling, a catalytic amount of 4-dimethylaminopyridine (DMAP) was added. The ice bath was removed stirring for 2 h, and the mixture was stirred at room temperature for an additional 2 h. The urea was filtered off, and the filtrate extracted with saturated $NaHCO_3$, 1N HCl and saturated NaCl. The organic layer was dried over $MgSO_4$, filtered and concentrated. A portion of the crude (850 mg) was purified by column chromatography on silica gel (70 g) eluting with hexanes/ethyl acetate. 8:2 to give a 78% yield of a bright yellow oil, $R_f$=0.49.

vanillylamine hydrochloride, (144 mg, 1.05×0.723 mmol) and $NEt_3$ (77 mg, 106 μL, 1.05×0.723 mmol) were dissolved in $CH_2Cl_2$ (7 mL). The solution was stirred and chilled in an ice bath. To the cold mixture was added EDC (153 mg, 1.1×0.723 mmol). The mixture was allowed to stir to room temperature overnight. The mixture was diluted with $CH_2Cl_2$ and extracted with water, 1N HCl, saturated $NaHCO_3$, and saturated NaCl. The organic layer was dried over Mg $SO_4$, filtered and concentrated. The crude product was purified by column chromatography on silica gel (50 g) eluting with $CH_2Cl_2$/MeOH, 94:6 (v/v), $R_f$=0.40, to give a 70% yield. Although Scheme III, Step 2 shows the incorporation of vanillylamine, any nucleophilic anti-inflammatory could be used (e.g., a phenolic-protected vanillyl alcohol).

In Step 3, the silyl-protected conjugate (229 mg, 0.506 mmol) was desilylated by dissolving in 5 mL of MeOH, adding $NH_4F$ (94 mg, 5×0.506 mmol) and heating at 60° C. for 7 days. The solution was cooled to room temperature and concentrated under reduced pressure. The crude product was purified by column Chromatography on silica gel (40 g) eluting with $CH_2Cl_2$/MeOH, 98:2 (v/v) and increasing to 92:8 to give a yield of 84%, ($R_f$=0.23 ($CH_2Cl_2$/MeOH, 94:6 (v/v), mp=164-174° C. with rapid heating). Spectral evidence confirmed the structure of NDH 4571. $^1$H NMR (acetone $d_6$) δ: 7.70-7.64 (m, 1H, —NH— of valine), 7.44 (d, 1H, $^3$J=4.5 Hz, $CH_3CH(OH)$—), 6.90 (m, 1H, Ar), 6.74-6.69 (m, 2H, Ar), 4.31-4.25 (m, 3H, —$NCH(CH_3)_2$— and Ar—$CH_2$—), 4.09-4.03 (m, 1H, $CH_3CH(OH)$—), 3.80

Scheme III

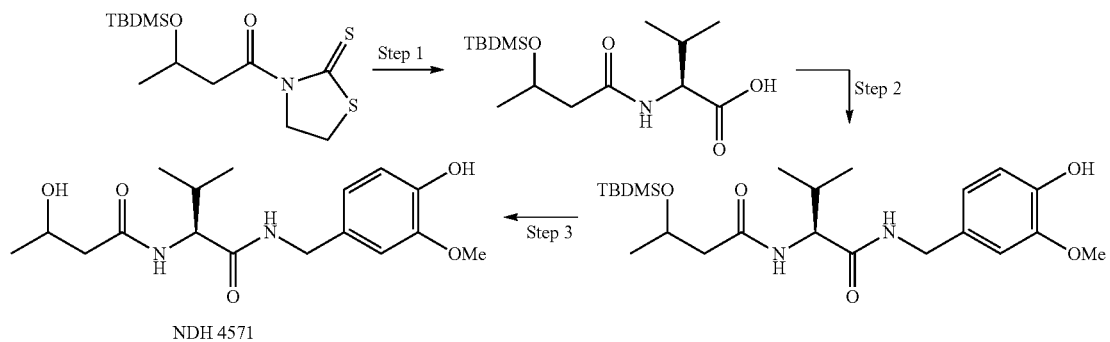

NDH 4571

While Step 1 can employ any of the anti-inflammatory amino acids, the pathway is illustrated with L-valine. The thiazolide (331.9 mg, 1.038 mmol), L-valine (128 mg, 1.05×1.038 mmol) and diisopropylethylamine (268 mg, 362 μL, 2×1.038 mmol) were dissolved in a mixture of 5.2 mL each of water and THF. The reaction mixture was stirred vigorously overnight. The colorless mixture was diluted with $CH_2Cl_2$ and extracted with 1 N HCl. The organic layer was concentrated, and the residue was dissolved in ether. The ether solution was extracted with saturated $NaHCO_3$. The bicarbonate layer was extracted twice with ether and then carefully acidified to pH=1 using 4N HCl. The resulting aqueous mixture was extracted with $CH_2Cl_2$. The organic layer was dried over $MgSO_4$, filtered, and concentrated. This product of Step 1 was used in Step 2 without further purification.

In Step 2, the N-substituted valine derivative (229.6 mg, 0.723 mmol), HOBt (103 mg, 1.05×0.723 mmol), 4-hydroxy-3-methoxybenzylamine hydrochloride, also known as (s, 3H, Ar—$OCH_3$), 2.42-2.27 (m, 2H, —$C(H(OH)CH_2CO$—), 2.20-2.07 (m, 1H, —$CH(CH_3)_2$), 1.14-1.11 (m, 3H, —$CH(CH_3)_2$), 0.93 (t, 3H, $^3$J=6.80 Hz, $CH(CH_3)_2$) and 0.91-0.88 (2 sets of doublets, 3H, $^3$J=6.85 Hz each, $CH_3CH(OH)$—).

B. Preparation of NSAID-Amino Acid Conjugates with Free Amino Acid Carboxyls (Illustrated with NDH 4476 or Compound IV-Acid)

While the amino acid conjugates of NSAIDs (those with a free amino acid carboxyl can be prepared by hydrolysis of the ester products of Scheme I, a far better route involves the thiazolide pathway. Thus, the synthesis of IV-acid was carried out as described in step 1 for the synthesis of NDH 4571 using the thiazolide of (S)-naproxen being condensed with L-valine to render a 68% yield of a white solid, NDH 4476 or IV-acid. Mp=164-166° C.; $R_f$=0.56 (rocket), $CH_2Cl_2$/MeOH, 9:1 (v/v); Exact mass (ESI) Calculated for $C_{19}H_{24}NO_4$ [M+H] 330.1700, found 330.1680. $^1$H NMR ($CDCl_3$) δ: 7.72-7.76 (m, 3H, Ar), 7.36 (d, 1H, $^3$J=8.40 Hz), 7.14 (dd, 1H, $^3J$=8.95 Hz, $^4J$=2.3 Hz), 7.10 (s, 1H), 5.82 (d, 1H, $^3J$=8.35 Hz), 4.45-4.42 (m, 1H), 3.90 (s, 3H), 3.77 (q, 1H, $^3J$=7.15 Hz), 2.16-2.09 (m, 1H), 1.60 (d, 3H, $^3J$=7.25 Hz), 0.87 (d, 3H, $^3J$=6.85 Hz) and 0.74 (d, 3H, $^3J$=6.85 Hz).

Although illustrated herein with S-naproxen and L-valine, this thiazolide route can be used for any carboxyl-terminated NSAID and any amino acid co-reactant.

C. Preparation of a Formula II Example Wherein and NSAID and a Vanilloid are Linked to an Amino Acid Through Nitrogen Atoms, Illustrated with NDH 4479 (Compound VII)

Compound VII or NDH 4479 is one of the most potent anti-inflammatories observed in the MEVM, with 110% suppression of phorbol-induced and 94% suppression of CEES-induced inflammation. The synthesis of VII was carried out as described in steps 1 and 2 for the synthesis of NDH 4571 but using the thiazolide of ibuprofen to give a 72% yield of a solid. Mp=56-66° C. with rapid heating; purification by column chromatography with silica gel and $CH_2Cl_2$/acetone, 92:8 (v/v); $R_f$=0.23, $CH_2Cl_2$/acetone, 92:8 (v/v); Exact mass (ESI) Calculated for $C_{26}H_{37}N_2O_4$ [M+H] 441.2748, found 441.2742. $^1$H NMR (CDCl$_3$) δ: 7.17-7.03 (m, 4H, Ar of Ibuprofen), 6.85-6.64 (m, 3H, Ar of vanillamine), 6.25-6.06 (m, 1H, NH of vanillamine), 5.86-5.76 (m, 1H, NH of vanillamine), 5.57 (br s, 1H, ArOH), 4.40-4.08 (m, 3H, —NCHCO— and Ar—CH$_2$—), 3.84-3.82 (m, 3H, ArOCH$_3$), 3.59-3.49 (m, 1H, ArCH(CH$_3$)CO—), 2.45-2.40 (m, 2H, (CH$_3$)$_2$CHCH$_2$—), 2.12-1.95 (m, 1H, (CH$_3$)$_2$CHCH$_2$—), 1.85-1.76 (m, 1H, (CH$_3$)$_2$CHCH(NH)CO—), 1.49-1.43 (m, 3H, ArCH(CH$_3$)CO—) and 0.88=0.63 (m, 12H, (CH$_3$)$_2$CHCH$_2$— and (CH$_3$)$_2$CHCH(NH)CO—).

D. Alternative Preparation of NDH 4535

While the synthesis of NDH 4535 could be achieved as described in Scheme I with ethanol as the esterifying alcohol, a much higher yield can be achieved by the thiazolide route. The synthesis of NDH 4535 is best carried out as described in step 1 for the synthesis of NDH 4571 using the thiazolide of (S)-naproxen, L-valine ethyl ester hydrochloride and THF only as solvent. The product was purified by column chromatography on silica gel and eluting with hexanes/ethyl acetate, 7:3 (v/v) to yield 84% of a crystalline product: mp=100-102° C., $R_f$=0.43 (hexanes/ethyl acetate 7:3 (v/v)). Exact mass (ESI) Calculated for $C_{21}H_{28}NO_4$ [M+H] 358.2013, found 358.2021. $^1$H NMR (CDCl$_3$) δ: 7.73-7.68 (m, 3H, Ar), 7.38 (dd, 1H, $^3J$=8.5 Hz, $^4J$=1.8 Hz, Ar), 7.13 (dd, 1H, $^3J$=8.9 Hz, $^4J$=2.55 Hz, Ar), 7.10 (d, 1H, $^4J$=2.45 Hz, Ar), 4.50-4.46 (m, 1H, N—CHCO), 4.14-4.01 (m, 2H, OCH$_2$CH$_3$), 2.10-2.03 (m, 1H, —CH(CH$_3$)$_2$), 1.60 (d, 3H, $^3J$=7.2 Hz, —CH(CH$_3$)CO—), 1.15 (t, 3H, $^3J$=7.15 Hz, OCH$_2$CH$_3$), 0.85 (d, 3H, $^3J$=6.85 Hz, —CH(CH$_3$)$_2$) and 0.74 (d, 3H, $^3J$=6.85 Hz, —CH(CH$_3$)$_2$).

E. Preparation of a Mixed Vanilloid-Amino Acid Platform Illustrated with NDH 4483

Since both vanillylamine and vanillyl alcohol possess anti-inflammatory activities and in similar fashion to the amino acid valine, the triple combination consistently displays MEVM numbers >65%. The synthesis of NDH 4483 was carried out as described in steps 1 and 2 for the synthesis of NDH 4571 but using the thiazolide carbamate of 4-acetoxy-3-methoxyvanillyl alcohol. The product was purified by column chromatography on silica gel and eluting with $CH_2Cl_2$/MeOH, 94:6 (v/v) to give a 61% yield of a white solid: $R_f$=0.53 ($CH_2Cl_2$/MeOH, 92:8 (v/v)). Exact mass (ESI) Calculated for $C_{24}H_{31}N_2O_4$ [M+H] 475.2075, found 475.2058. $^1$H NMR (CDCl$_3$) δ: 6.97 (d, 1H, $^3J$=8.0 Hz, H-5 of vanillyl alcohol), 6.92 (s, 1H, H-2 of vanillyl alcohol), 6.88 (d, 1H, $^3J$=8.2 Hz, H-6 of vanillyl alcohol), 6.82 (d, 1H, $^3J$=8.0 Hz, H-5 of vanillylamine), 6.75 (s, 1H, H-2 of vanillylamine), 6.72 (d, 1H, $^3J$=7.9 Hz, H-6 of vanillylamine), 5.61 (s, 1H, ArOH), 5.34 (d, 1H, $^3J$=8.5 Hz, NH of valine), 5.05-4.99 (m, 2H, ArCH$_2$O—), 4.41-4.27 (m, 2H, ArCH$_2$NH—), 3.96-3.91 (m, 1H, —NHCHCO—), 3.82 (s, 3H, ArOCH$_3$), 3.80 (s, 3H, ArOCH$_3$), 2.29 (s, 3H, ArOCOCH$_3$), 2.13 (m, 1H, —CH(CH$_3$)$_2$), 0.97 (d, 3H, $^3J$=6.8 Hz, —CH(CH$_3$)CH$_3$) and 0.91 (d, 3H, $^3J$=6.8 Hz, —CH(CH$_3$)CH$_3$).

The amino acid—3,3-dimethylbutyl esters lacking the NSAID moiety were all inactive in inhibition of AChE as were the NSAID-amino acid ethyl and n-butyl esters. These displayed IC$_{50}$ values greater than 100 μM and precise IC$_{50}$ values could not be determined due to solubility limitations of the compound being tested. Some of these simple conjugates did, however, possessed modest (usually 5-44%) anti-inflammatory activity in the mouse ear vesicant model (e.g., IV-acid and IV-ethyl ester at 40-44% and the n-butyl esters designated NDH 4651-4654 at <25%). These data indicate that the choline mimics alone (or AA linked choline mimics) do not have a high affinity for AChE. Low micromolar anticholinesterase IC$_{50}$ activities are obtained only when the choline mimics are covalently linked to an aromatic and lipophilic NSAID such as diclofenac. While the relationship between the IC$_{50}$ values for inhibition of AChE and the measured anti-inflammatory effects in the MEVIVI is not linear, it can be observed (Table I) that compounds with the lowest IC$_{50}$'s (e.g., below 3.3 micromolar) displayed superior inflammation suppression percentages for at least one of the inflammation-inducers. (See NDH 4537, 4577, 4578, and 4591)

TABLE I

NSAID-Amino Acid—3,3-dimethylbutyl Esters (other structural examples are described elsewhere herein)

| NDH # | NSAID | Amino Acid | AChE IC$_{50}$ (μM) | % CEES$^a$ | % TPA$^a$ |
|---|---|---|---|---|---|
| 4618 | Naproxen | Proline | >100* | 34 | Irritant |
| 4619 | Ibuprofen | Proline | NT | 24 | 35 |
| 4617 | Indomethacin | Proline | >25* | 25 | 68*** |
| 4628 | Diclofenac | Proline | 15.4 +/- 2.1 | 10 | 76*** |
| 4614 | Ibuprofen | Glycine | 27.9 +/- 2.7 | Irritant | 18 |
| 4613 | Naproxen | Glycine | NT | 66** | 54** |
| 4615 | Indomethacin | Glycine | 6.63 +/- 0.4 | 21 | 55** |
| 4627 | Diclofenac | Glycine | >50* | Irritant | 45** |
| 4576 | Ibuprofen | Phenylalanine | 4.34 +/- 0.2 | Irritant | Irritant |
| 4572 | Naproxen | Phenylalanine | 4.77 +/- 0.2 | 83** | 42** |
| 4577 | Indomethacin | Phenylalanine | 2.55 +/- 0.7 | 62** | 79** |
| 4578 | Diclofenac | Phenylalanine | 1.31 +/- 0.1 | 120** | 90** |
| 4595 | Ibuprofen | Valine | 8.91 +/- 0.4 | 47 | Irritant |
| 4596 | Naproxen | Valine | 18.6 +/- 3.0 | 51 | 22 |
| 4537 | Indomethacin | Valine | 3.29 +/- 0.3 | 59 | 107*** |
| 4591 | Diclofenac | Valine | 1.85 +/- 0.1 | 85** | 31 |

*A precise IC$_{50}$ could not be determined due to limits in inhibitor solubility
NT means not tested
$^a$Values differ from a positive control based on one-way ANOVA,
**P < 0.05,
***P < 0.005

Representative Physical Data for Anti-inflammatories of Aspect II Containing Amino Acid Linkers Stability. If vanillyl amine (i.e., 3-methoxy-4-hydroxybenzyl-NH—) is attached to any of these anti-inflammatory amino acid platforms it constitutes a shelf-stable, slowly metabolized moiety. However, if vanillyl alcohol (i.e., 3-methoxy-4-hydroxybenzyl-O—) is attached, the resulting candidate pharmaceuticals are unstable unless the free-phenolic hydroxyl is protected by acylation. Acetate is a

(S)-3,3-Dimethylbutylpyrrolidine-2-carboxylate

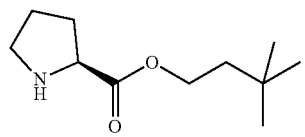

NDH4620

Light yellow liquid, 85% yield; $R_f$ 0.12 (Hexanes:ethyl acetate 1:1); $^1$H NMR (500 MHz, CDCl$_3$)=δ 0.92 (s, 9H), 1.53-1.57 (t, 2H, J=7.15 Hz), 1.70-1.76 (m, 2H), 1.79-1.84 (m, 1H), 270, 2.05-2.11 (m, 1H), 2.85-2.90 (m, 1H), 3.03-3.08 (m, 1H), 3.69-3.72 (dd, 1H, J=5.70, 8.60 Hz), 4.14-4.17 (dt, 2H, J=1.70, 3.70 Hz); $^{13}$C NMR (125 MHz, CDCl$_3$): δ25.5, 29.6, 29.7, 30.3, 41.8, 47.1, 59.9, 62.7, 175.6; HRMS (m/z): calc. for C$_{11}$H$_{21}$NO$_2$ 200.1645; meas. 200.1638.

(S)-3,3-Dimethylbutyl-1-(2-(4-isobutylphenyl)propanoyl)pyrrolidine-2-carboxylate

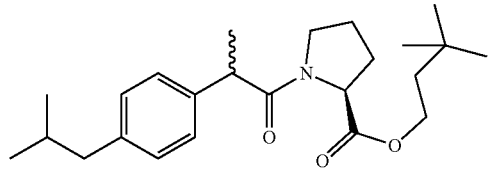

NDH4619

Clear liquid, 93% yield; $R_f$ 0.74 (Hexanes:ethyl acetate 1:1); according to $^1$H NMR, 19.2% of the cis isomer of the proline peptide bond is present: $^1$H NMR trans isomer (500 MHz, CDCl$_3$): δ 0.85-0.89 (m, 6H), 0.92 (s, 9H), 1.38-1.42 (q, 3H, J=10.9 Hz), 1.54-1.57 (t, 2H, J=7.55 Hz), 1.69-1.90 (m, 4H), 1.93-2.02 (m, 1H), 2.38-2.42 (dd, 2H, J=2.55, 7.18 Hz), 3.17-3.50 (m, 2H), 3.64-3.76 (m, 1H), 4.10-4.20 (m, 2H), 4.39-4.49 (m, 1H), 7.02-7.08 (m, 2H), 7.13-7.19 (m, 2H); cis isomer: δ0.85-0.89 (m, 6H), 0.87 (s, 9H), 1.38-1.42 (q, 3H, J=10.9 Hz), 1.47-1.50 (t, 2H, J=7.50 Hz), 1.69-1.90 (m, 4H), 2.05-2.15 (m, 1H), 2.38-2.42 (dd, 2H, J=2.55, 7.18 Hz), 3.173.50 (m, 2H), 3.64-3.76 (m, 1H), 4.10-4.15 (m, 1H), 4.21-4.25 (m, 1H), 4.39-4.53 (m, 1H), 7.027.08 (m, 2H), 7.13-7.19 (m, 2H); $^{13}$C NMR trans isomer (125 MHz, CDCl$_3$): δ20.3, 22.4, 22.5, 24.9, 29.6, 29.8, 30.1, 41.6, 44.5, 45.1, 46.8, 59.2, 62.7, 127.3, 129.4, 138.4, 140.0, 172.3, 172.6; cis isomer: δ 20.4, 22.3, 22.5, 24.8, 29.0, 30.2, 31.2, 41.7, 44.6, 45.0, 46.6, 58.9, 62.8, 127.0, 127.3, 129.5. 129.6, 172.8, 172.9; Calc. for C$_{24}$H$_{37}$NO$_3$·0.25H$_2$O (392.06): C, 73.53; H, 9.64; N, 3.57. Found: C, 73.86; H, 9.41; N, 3.47.

(S)-3,3-Dimethylbutyl-1-((S)-2-(6-methoxynaphthalen-2-yl)propanoyl)pyrrolidine-2-carboxylate

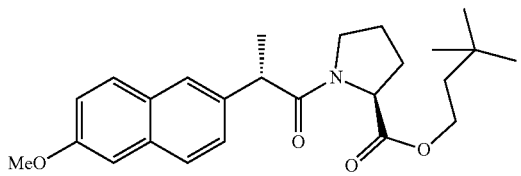

NDH4618

White solid, 73% yield; MP 111.5-112.5° C.; $R_f$ 0.62 (Hexanes: ethyl acetate 1:1); according to $^1$H NMR, 13.4% of the cis isomer of the proline peptide bond is present: $^1$H NMR, trans isomer (500 MHz, DMF): δ0.99 (s, 9H), 1.52-1.57 (m, 5H), 1.92-1.97 (m, 2H), 2.04-2.07 (m, 1H), 2.332.36 (m, 1H), 3.35-3.39 (m, 1H), 3.87-3.92 (m, 1H), 4.07 (s, 3H), 4.17-4.26 (m, 3H), 4.55-4.57 (dd, 1H, J=4.20, 8.60 Hz), 7.31-7.34 (dd, 1H, J=2.50, 9.00 Hz), 7.50 (d, 1H, J=2.50 Hz), 7.61-7.64 (dd, 1H, J=1.75, 8.45 Hz), 7.94-7.98 (t, 3H, J=8.65 Hz); cis isomer: δ 1.12 (s, 9H), 1.52-1.57 (m, 5H), 1.76-1.80 (t, 2H, J=7.25 Hz), 1.92-1.97 (m, 2H), 1.91-1.97 (m, 1H), 2.19-2.23 (m, 1H), 3.55-3.60 (m, 1H), 3.87-3.92 (m, 1H), 4.07 (s, 3H), 4.43-4.45 (m, 2H), 7.31-7.34 (dd, 1H, J=2.50, 9.00 Hz), 7.50 (d, 1H, J=2.50 Hz), 7.61-7.64 (dd, 1H, J=1.75, 8.45 Hz), 7.91 (bs, 1H), 7.94-7.98 (t, 2H, J=8.65 Hz); $^{13}$C NMR, trans isomer (125 MHz, DMF): δ20.1, 22.4, 31.1, 24.9, 41.7, 44.0, 46.9, 55.2, 59.4, 62.1, 63.2, 106.1, 118.9, 126.3, 126.9, 127.4, 129.3, 129.4, 133.9, 137.3, 157.9, 172.0, 172.4; cis isomer: δ 20.1, 22.4, 31.1, 41.8, 44.3, 46.6, 55.2, 59.2, 62.1, 63.2, 106.0, 119.1, 125.9, 126.3, 126.9, 127.6, 129.3, 129.4, 134.0, 137.1, 157.9, 172.5, 172.8; Calc. for C$_{25}$H$_{33}$NO$_4$ (411.53): C, 72.96; H, 8.08; N, 3.40. Found: C, 73.22; H, 7.98; N, 3.47.

(S)-3,3-Dimethylbutyl-1-(2-(1-(4-Chlorobenzoyl)-5-methoxy-2-methyl-1H-indol-3-yl)acetyl) pyrrolidine-2-carboxylate

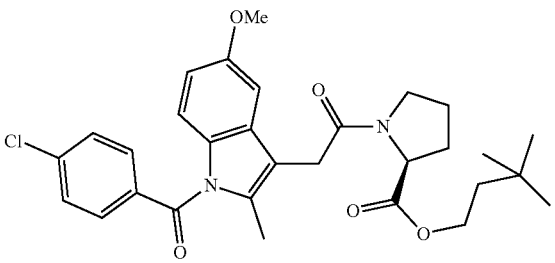

NDH4617

Yellow oil, 96% yield; $R_f$ 0.47 (Hexanes:ethyl acetate 1:1); according to $^1$H NMR, 18.5% of the cis isomer of the proline peptide bond is present: $^1$H NMR, trans isomer (500 MHz, CDCl$_3$): δ0.88 (5, 9H), 1.41-1.45 (1, 2H, J=7.55 Hz), 1.93-2.03 (m, 2H), 2.05-2.09 (m, 1H), 2.18-2.20 (m, 1H), 2.36 (5, 3H), 3.62-3.71 (m, 2H), 3.70 (5, 2H), 3.77 (5, 3H), 4.03-4.07 (m, 2H), 4.30-4.33 (dd, 1H, J=4.55, 8.60 Hz), 6.63-6.66 (dd, 1H, J=2.50, 9.00 Hz), 6.94-6.97 (m, 1H), 6.99 (d, 1H, J=2.50 Hz), 7.52 (d, 2H, J=8.45 Hz), 7.61-7.64 (m, 2H); cis isomer: δ0.89 (5, 9H), 1.47-1.51 (1, 2H, J=7.40 Hz), 1.84-1.90 (m, 1H), 1.93-2.03 (m, 2H), 2.21 (5, 3H), 3.45-3.49 (m, 3H). 3.70 (5, 2H), 3.77 (s, 3H), 4.08-4.13 (m, 2H), 4.58-4.61 (dd, 1H, J=1.95, 8.60 Hz), 6.63-6.66 (dd, 1H, J=2.50, 9.00 Hz), 6.94-6.97 (m, 1H), 6.99 (d, 1H, J=2.50 Hz), 7.52 (d, 2H, J=8.45 Hz), 7.61-7.64 (m, 2H); $^{13}$C NMR, trans isomer (500 MHz, CDCl$_3$): 0 13.6, 25.0, 29.5, 29.6, 29.7, 31.2, 41.6, 47.3, 55.7, 59.3, 62.9, 101.7, 111.6, 112.9, 114.8, 129.1, 130.8, 130.9, 131.2, 134.0, 135.6, 139.2, 156.0, 168.3, 168.8, 172.3; cis isomer: δ13.5, 22.3, 25.0, 29.1, 29.7, 31.7, 41.7, 46.8, 53.5, 59.6, 63.5, 101.6, 111.7, 112.9, 114.8, 129.1, 130.8, 130.9, 131.2, 134.0, 135.6, 139.2, 156.1, 168.3, 168.9, 172.3; Calc. for C$_{30}$H$_{35}$ClN$_2$O$_5$·0.5CH$_2$Cl$_2$ (581.53): C, 63.00; H, 6.24; N, 4.82. Found: C, 63.34; H, 5.69; N, 4.81.

(S)-3,3-Dimethylbutyl-1-(2-(2-(2, 6-dichlorophenylamino)phenyl)acetyl)pyrrolidine-2-carboxylate

NDH4628

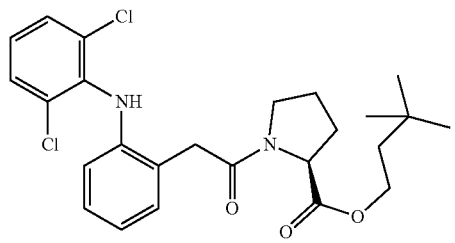

Clear oil, 82% yield; R$_f$ 0.31 (Hexanes:ethyl acetate, 4:1); according to $^1$H NMR, 22.1% of the cis isomer of the proline peptide bond is present: $^1$H NMR, trans isomer (500 MHz, CDCl$_3$): δ0.86 (s, 9H), 1.41-1.45 (1, 2H, J=15.0 Hz), 1.99-2.01 (m, 2H), 2.05-2.11 (m, 1H), 2.11-2.17 (m, 1H), 3.62-3.71 (m, 2H), 3.72-3.87 (m, 3H), 4.06-4.14 (m, 2H), 4.48-4.51 (dd, 1H, J=3.50, 8.60 Hz), 6.48 (d, 1H, J=7.75 Hz), 6.84-6.89 (1, 1H, J=7.25 Hz), 6.91-6.94 (1, 1H, J=8.00 Hz), 7.06 (d, 1H, J=7.40 Hz), 7.15 (d, 1H, J=7.50 Hz), 7.29 (d, 2H, J=8.00 Hz); $^1$H NMR, cis isomer (500 MHz, CDCl$_3$): δ0.90 (s, 9H), 1.52-1.56 (1, 2H, J=7.45 Hz), 1.88-1.94 (m, 2H), 2.13-2.19 (m, 1H), 2.23-2.32 (m, 1H), 3.54-3.62 (m, 2H), 3.72-3.87 (m, 3H), 4.18-4.28 (m, 2H), 4.63-4.66 (dd, 1H, J=2.55, 8-0.53 Hz), 6.49-6.51 (m, 1H), 6.85-6.88 (m, 1H), 6.91-6.95 (1, 1H, J=8.00 Hz), 7.04-7.08 (m, 2H), 7.30 (d, 2H, J=8.00 Hz); $^{13}$C NMR, trans isomer (125 MHz, CDCl$_3$): δ24.9, 29.2, 29.6, 29.7, 39.2, 41.5, 47.6, 60.1, 62.9, 117.8, 121.2, 123.8, 124.5, 127.6, 128.8, 130.0, 130.7, 138.1, 143.7, 170.2, 172.2; $^{13}$C NMR, cis isomer (125 MHz, CDCl$_3$): δ22.6, 29.6, 29.7, 31.6, 39.1, 41.7, 46.9, 60.1, 63.7, 117.8, 121.2, 123.8, 124.7, 127.7, 128.8, 129.9, 130.6, 138.1, 143.7, 170.8, 172.3.

3,3-Dimethylbutyl 2-aminoacetate

NDH4621

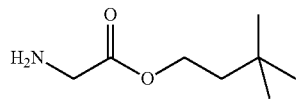

Light yellow liquid, 58% yield; R$_f$ 0.55 (Methylene chloride:methanol, 9:1 with 3 drops NH$_4$OH); $^1$H NMR (500 MHz, CDCl$_3$): δ0.91 (s, 9H), 1.42-1.47 (bs, 2H), 1.52-1.56 (1, 2H, J=7.50 Hz), 3.38 (s, 2H), 4.13-4.18 (1, 2H, J=7.45 Hz); $^{13}$C NMR (125 MHz, CDCl$_3$): δ29.7, 29.8, 41.8, 44.1, 62.7, 174.3; HRMS (m/z): calc. for C$_8$H$_{17}$NO$_2$ [M+1]: 160.1332; meas. 160.1321.

3,3-Dimethylbutyl 2-(2-(4-isobutylphenyl)propanamido)acetate

NDH4614

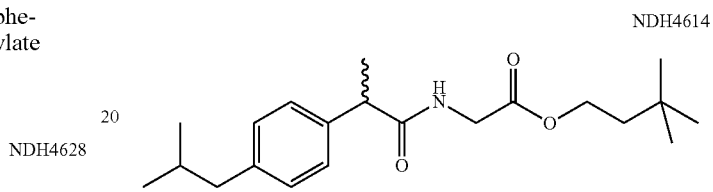

Clear liquid, 91% yield; R$_f$ 0.37 (Hexanes:ethyl acetate 4:1); $^1$H NMR (500 MHz, CDCl$_3$): δ0.88 (d, 6H, J=6.60 Hz), 0.89 (s, 9H), 1.51 (d, 3H, J=7.15 Hz), 1.49-1.54 (1, 2H, J=5.80 Hz), 1.80 1.86 (m, 1H), 2.43 (d, 2H, J=7.20 Hz), 3.55-3.60 (q, 1H, J=7.15 Hz), 3.87-4.00 (dq, 2H, J=5.00, 18.5 Hz), 4.12-4.16 (1, 2H, J=7.50 Hz), 5.83 (bs, 1H), 7.10 (d, 2H, J=8.00 Hz), 7.19 (d, 2H, J=8.00 Hz); $^{13}$C NMR (125 MHz, CDCl$_3$): 8 18.4, 22.4, 29.5, 29.7, 30.2, 41.6, 44.9, 45.0, 46.6, 63.2, 127.4, 129.7, 138.1, 140.9, 170.0, 174.6; Calc. for C$_{21}$H$_{33}$NO$_3$·0.25H$_2$O (351.99): C, 71.66; H, 9.59; N, 3.98. Found: C, 71.84; H, 9.35; N, 4.02.

(S)-3,3-Dimethylbutyl 2-(2-(6-methoxynaphthalen-2-yl)propanamido)acetate

NDH4613

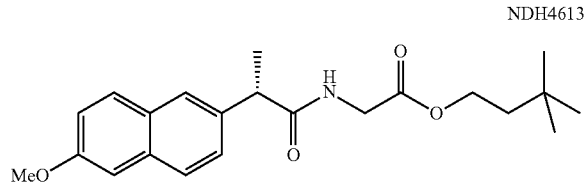 [SMILES: COc1ccc2cc([C@H](C)C(=O)NCC(=O)OCCC(C)(C)C)ccc2c1]

Clear oil, 99% yield; R$_f$ 0.20 (Hexanes:ethyl acetate 4:1); $^1$H NMR (500 MHz, CDCl$_3$): δ0.87 (s, 9H), 1.45-1.49 (1, 2H, J=7.50 Hz), 1.59 (d, 3H, J=7.20 Hz), 3.71-3.77 (q, 1H, J=7.15 Hz), 3.87-4.00 (dq, 2H, J=5.40, 18.4 Hz), 3.90 (s, 3H), 4.09-4.14 (1, 2H, J=7.40 Hz), 5.85 (bs, 1H), 7.10 (d, 1H, J=2.45 Hz), 7.12-7.15 (dd, 1H, J=2.55, 8.88 Hz), 7.36-7.39 (dd, 1H, J=1.70, 8.43 Hz), 7.67 (s, 1H), 7.68-7.73 (1, 2H, J=8.55 Hz); $^{13}$C NMR (125 MHz, CDCl$_3$): δ18.4, 29.5, 29.7, 41.5, 41.6, 46.8, 55.3, 63.2, 105.7, 119.2, 126.2, 126.3, 127.6, 129.0, 129.3, 133.8, 136.0, 157.8, 169.9, 174.5; Calc. for C$_{22}$H$_{29}$NO$_4$ (371.47): C, 71.13; H, 7.87; N, 3.77. Found: C, 70.97; H, 7.69; N, 3.80.

3,3-Dimethylbutyl 2-(2-(1-(4-chlorobenzoyl)-5-methoxy-2-methyl-1H-indol-3-yl)acetamido)acetate

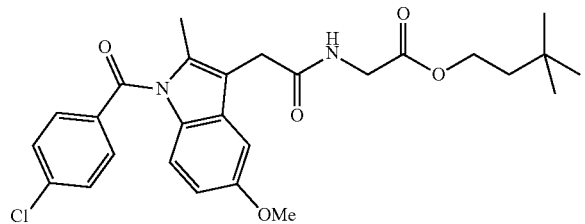

NDH4615

Yellow solid, 89% yield; MP 118.5-120° C.; $R_f$ 0.11 (Hexanes:ethyl acetate 4:1); $^1$H NMR (500 MHz, CDCl$_3$): δ0.89 (s, 9H), 1.48-1.51 (1, 2H, J=7.55 Hz), 2.36 (s, 3H), 3.67 (s, 2H), 3.82 (s, 3H), 3.95 (d, 2H, J=5.40 Hz), 4.11-4.15 (1, 2H, J=7.50 Hz), 6.07-6.09 (1, 1H, J=5.00 Hz), 6.68-6.71 (dd, 1H, J=2.55, 8.95 Hz), 6.91 (s, 1H), 6.90-6.94 (d, 1H, J=1-0.2 Hz), 7.45-7.48 (m, 2H), 7.64-7.67 (m, 2H); $^{13}$C NMR (125 MHz, CDCl$_3$): δ13.4, 29.5, 29.7, 32.0, 41.5, 41.6, 55.8, 63.3, 100.8, 112.5, 112.5, 115.1, 129.2, 130.2, 131.0, 131.3, 133.6, 136.4, 139.5, 156.3, 168.3, 169.7, 170.2; Calc. for C$_{27}$H$_{31}$ClN$_2$O$_5$ (499.00): C, 64.99; H, 6.26; N, 5.61. Found: C, 64.63; H, 5.94; N, 5.50.

3,3-Dimethylbutyl 2-(2-(2-(2, 6-dichlorophenylamino)phenyl)acetamido)acetate

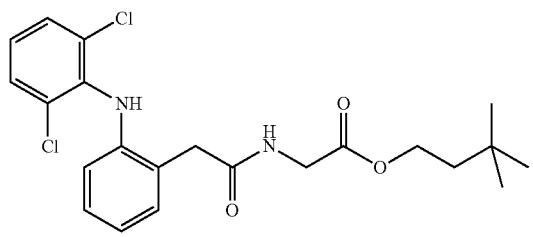

NDH4627

White solid, 70% yield; mp 118-119° C.; $R_f$ 0.36 (Hexanes: ethyl acetate 4:1); $^1$H NMR (500 MHz, CDCl$_3$): δ0.89 (s, 9H), 1.49-1.53 (1, 2H, J=7.50 Hz), 3.72 (s, 2H), 4.01 (d, 2H, J=5.05 Hz), 4.15-4.18 (1, 2H, J=7.45 Hz), 6.42-6.48 (bs, 1H), 6.49 (d, 1H, J=8.05 Hz), 6.88-6.92 (1, 1H, J=7.40 Hz), 6.93-6.97 (1, 1H, J=8.15 Hz), 7.07-7.11 (1, 1H, J=7.85 Hz), 7.17 (d, 1H, J=7.40 Hz), 7.31 (d, 3H, J=8.10 Hz); $^{13}$C NMR (125 MHz, CDCl$_3$): δ29.1, 29.2, 40.2, 41.1, 41.3, 62.9, 117.2, 121.2, 123.7, 124.0, 127.6, 128.4, 129.5, 130.2, 137.2, 142.5, 169.4, 171.3; Calc. for C$_{22}$H$_{26}$ClN$_2$O$_3$ (437.36): C, 60.42; H, 5.99; N, 6.41. Found: C, 60.36; H, 6.09; N, 6.26.

(S)-3,3-Dimethylbutyl-2-amino-3-phenylpropanoate

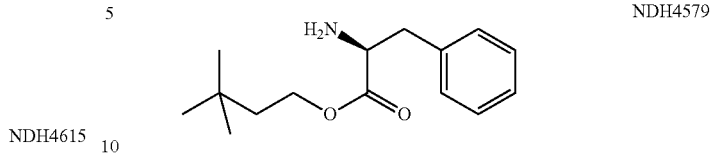

NDH4579

Light yellow liquid, 36% yield; $R_f$ 0.43 (Methylene chloride: hexanes:ethanol, 90:8:2); $^1$H NMR (500 MHz, CDCl$_3$): δ0.91 (s, 9H), 1.42-1.45 (bs, 2H), 1.49-1.52 (1, 2H, J=7.70 Hz), 2.80-3.08 (dd, 1H, J=7.95, 128 Hz), 2.83-3.06 (dd, 1H, J=7.95, 102 Hz), 3.65-3.70 (dd, 1H, J=5.30, 7.93 Hz), 4.11-4.16 (m, 2H), 7.15-7.19 (d, 2H, J=7.15 Hz), 7.21-7.24 (m, 1H), 7.26-7.30 (m, 2H); $^{13}$C NMR (125 MHz, CDCl$_3$): δ29.6, 29.7, 41.2, 41.7, 56.0, 62.7, 126.8, 128.6, 129.3, 137.4, 175.1; HRMS (m/z): calc. for C$_{15}$H$_{23}$NO$_2$ 250.1802; meas. 250.1791.

(S)-3,3-Dimethylbutyl 2-(2-(4-isobutylphenyl)propanamido)-3-phenylpropanoate

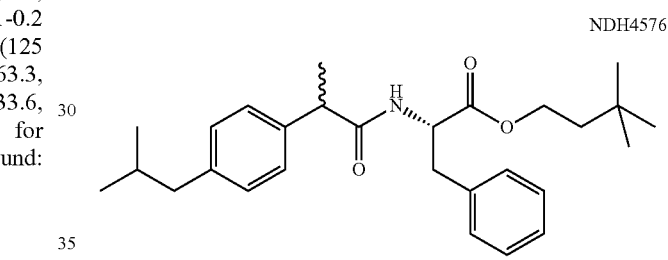

NDH4576

Clear oil, 73% yield; $R_f$ 0.59 (Hexanes:ethyl acetate 4:1); $^1$H N.MR (500 MHz, CDCl$_3$): δ0.82-1.01 (m, 15H), 1.34-1.53 (m, 5H), 1.78-1.90 (m, 1H), 2.42-2.50 (dd, 2H, J=7.20, 10.9 Hz), 2.94-2.97 (1, 1H, J=3.80 Hz), 2.91-3.07 (m, 1H), 3.44-3.53 (m, 1R), 4.01-4.16 (m, 2H), 4.734.84 (m, 1R), 5.71-5.74 (m, 1R), 6.74 (d, 1H, J=7.20 Hz), 6.90-6.93 (m, 1R), 7.05-7.16 (m, 5R), 7.15-7.20 (m, 2R); $^{13}$C NMR (125 MHz, CDCl$_3$): δ18.19, 22.42, 29.52, 29.53, 29.65, 29.69, 30.20, 30.24, 37.72, 37.76, 41.55, 41.60, 45.06, 45.08, 46.62, 46.72, 52.92, 53.15, 63.16, 63.20, 126.89, 126.96, 127.40, 127.41, 128.37, 128.45, 129.24, 129.29, 129.60, 129.62, 135.63, 135.85, 137.67, 138.27, 140.74, 171.40, 171.49, 173.59, 173.96; Calc. for C$_{25}$H$_{39}$NO$_3$ (437.61): C, 76.85; H, 8.98; N, 3.20. Found: C, 76.90; H, 9.19; N, 3.17.

(S)-3,3-Dimethylbutyl 2-((S)-2-(6-methoxynaphthalen-2-yl)propanamido)-3-phenylpropanoate

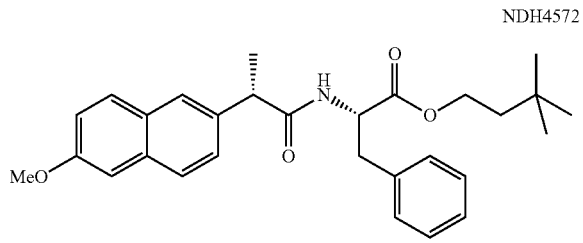 [SMILES: COc1ccc2cc([C@H](C)C(=O)N[C@@H](Cc3ccccc3)C(=O)OCCC(C)(C)C)ccc2c1]

NDH4572

Clear oil, 82% yield; $R_f$ 0.42 (Hexanes:ethyl acetate 4:1); $^1$H N.MR (500 MHz, CDCl$_3$): δ0.83 (s, 9R), 1.36-1.40 (1, 2H, J=7.45 Hz), 1.57 (d, 3H, J=7.25 Hz), 2.94-3.05 (dq, 2H, J=5.75, 13.8 Hz), 3.65-3.70 (q, 1H, J=7.20 Hz), 3.91 (s, 3R), 3.99-4.10 (m, 2R), 4.73-4.78 (m, 1R), 5.78 (d, 1H, J=7.75 Hz), 6.83-6.86 (m, 2H), 7.02-7.06 (1, 2H, J=7.65 Hz), 7.09-7.15 (m, 3R), 7.29-7.32 (dd, 1H, J=1.80, 8.50 Hz), 7.58 (s, 1R), 7.66 (dd, 2H, J=4.05, 8.68 Hz); $^{13}$C NMR (125 MHz, CDCl$_3$): δ18.1, 29.5, 29.6, 37.7, 41.5, 47.0, 53.1, 55.4, 63.2, 105.6, 119.1, 126.2, 126.4, 126.9, 127.5, 128.4, 129.0, 129.2, 129.3, 133.8, 135.6, 135.7, 157.8, 171.3, 173.9; Calc. for C$_{29}$H$_{35}$NO$_4$ (461.59): C, 75.46; H, 7.64; N, 3.03. Found: C, 75.03; H, 7.59; N, 3.03.

(S)-3,3-Dimethylbutyl 2-(2-(1-(4-chlorobenzoyl)-5-methoxy-2-methyl-1H-indol-3-yl)acetamido)3-phenylpropanoate

NDH4577

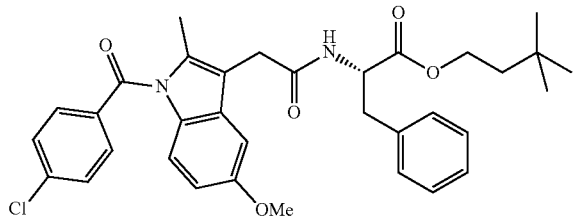

Light yellow oil, 92% yield; $R_f$ 0.21 (Hexanes:ethyl acetate 4:1); $^1$H NMR (500 MHz, CDCl$_3$): δ0.87 (s, 9R), 1.43-1.49 (1, 2H, J=7.50 Hz), 2.19 (s, 3R), 2.94-3.03 (m, 2H), 3.55-3.63 (q, 2H, J=17.5, 18.6 Hz), 3.80 (s, 3R), 4.06-4.15 (m, 2R), 4.78-4.82 (m, 1R), 5.97 (d, 1H, J=8.05 Hz), 6.72-6.75 (dd, 1H, J=2.55, 9.03 Hz), 6.77 (d, 2H, J=7.15 Hz), 6.86 (d, 1H, J=2.45 Hz), 6.997.03 (m, 3R), 7.06-7.12 (m, 1R), 7.42 (d, 2H, J=8.75 Hz), 7.53 (d, 2H, J=7.75 Hz); $^{13}$C NMR (125 MHz, CDCl$_3$): δ13.3, 29.5, 29.7, 32.1, 37.6, 41.6, 52.9, 55.8, 63.3, 100.7, 112.5, 112.6, 115.2, 127.0, 128.4, 129.1, 129.2, 130.2, 131.0, 131.2, 133.7, 135.4, 136.0, 139.4, 156.4, 168.2, 169.3, 171.1; Calc. for C$_{34}$H$_{37}$ClN$_2$O$_5$ (589.12): C, 69.32; H, 6.33; N, 4.76. Found: C, 68.85; H, 6.13; N, 4.60.

(S)-3,3-Dimethylbutyl 2-(2-(2-(2, 6-dichlorophenylamino)phenyl)acetamido)-3-phenylpropanoate

NDH4578

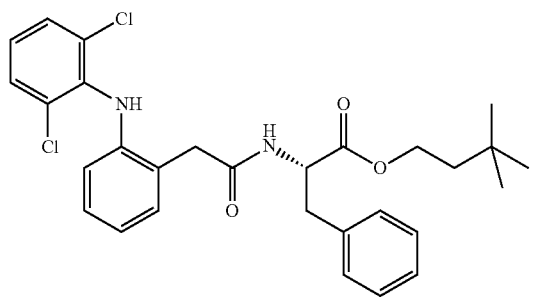

Light yellow oil, 92% yield; $R_f$ 0.65 (Hexanes:ethyl acetate 4:1); $^1$H NMR (500 MHz, CDCl$_3$): δ0.89 (s, 9H), 1.45-1.50 (m, 2H), 3.04-3.13 (m, 2H), 3.59-3.72 (q, 2H, J=14.4, 45.4 Hz), 4.064.18 (m, 2H), 4.83-4.87. (m, 1H), 6.13 (d, 1H, J=7.80 Hz), 6.50 (d, 1H, J=7.90 Hz), 6.89-6.98 (m, 3H), 6.95-6.98 (1, 1H, J=8.00 Hz), 7.10 (d, 2H, J=7.40 Hz), 7.16-7.19 (m, 3H), 7.32 (d, 2H, J=8.05 Hz), 7.36 (bs, 1H); $^{13}$C NMR (125 MHz, CDCl$_3$): δ29.5, 29.7, 37.7, 41.0, 41.6, 53.3, 63.4, 117.7, 121.6, 124.2, 124.4, 127.1, 128.0, 128.5, 128.8, 129.4, 130.1, 130.6, 135.6, 137.7, 143.0, 170.9, 171.3; Calc. for C$_{29}$H$_{32}$Cl$_2$N$_2$O$_3$·0.5H$_2$O (536.49): C, 64.92; H, 6.20; N, 5.22. Found: C, 64.99; H, 5.78; N, 5.05.

(S)-3,3-Dimethylbutyl 2-amino-3-methylbutanoate

NDH4597

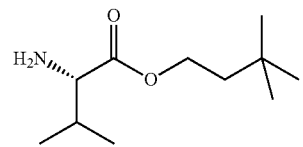

Light yellow liquid, 64% yield; $R_f$ 0.16 (hexanes:ethyl acetate: 4:1); $^1$H NMR (500 MHz, CDCl$_3$): δ0.87 (d, 3H, J=6.85 Hz), 0.92 (s, 9H), 0.95 (d, 3H, J=6.90 Hz), 1.38-1.45 (bs, 2H), 1.53-1.57 (1, 2H, J=7.70 Hz), 1.97-2.02 (m, 1H), 3.23 (d, 1H, J=4.95 Hz), 4.13-4.16 (1, 2H, J=7.35 Hz); $^{13}$C NMR (125 MHz, CDCl$_3$): δ 17.2, 19.4, 29.6, 29.7, 32.1, 41.8, 60.0, 62.5, 175.7; HRMS (m/z): calc. for C$_{11}$H$_{23}$NO$_2$ 202.1802; meas. 202.1784.

(S)-3,3-Dimethylbutyl 2-(2-(4-isobutylphenyl)propanamido)-3-methylbutanoate

NDH4595

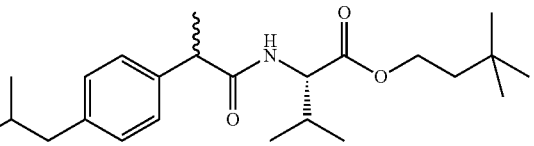

Clear liquid, 92% yield; $R_f$ 0.55 (Hexanes:ethyl acetate 4:1); $^1$H NMR (500 MHz, CDCl$_3$): δ0.64 (d, 1.5H, J=6.90 Hz), 0.71-0.75 (dd, 3H, J=6.85, 9.20 Hz), 0.83 (d, 1.5H, J=6.85 Hz), 0.85-0.87 (m, 6H), 0.89 (s, 4.5H), 0.90 (s, 4.5H), 1.46-1.53 (m, 5H), 1.79-1.86 (m, 1H), 1.99-2.10 (m, 1H), 2.43 (d, 2H, J=7.20 Hz), 3.53-3.57 (q, 0.5H, J=7.15 Hz), 3.57-3.62 (q, 0.5H, J=7.30 Hz), 4.07-4.14 (m, 2H), 4.43-4.49 (m, 1H), 5.70-5.78 (dd, 1H, J=8.80, 24.8 Hz), 7.09-7.12 (m, 2H), 7.17-7.22 (m, 2H); $^{13}$C NMR. (125 MHz, CDCl$_3$): 0 17.3, 17.5, 18.1, 18.3, 18.9, 19.0, 22.2. 22.3, 29.5, 29.6, 29.7, 30.2, 31.2, 31.3, 41.6, 41.7, 45.0, 45.1, 46.8, 46.9, 56.8, 56.9, 62.9, 63.0, 127.3, 127.4, 129.7, 138.6, 140.8, 140.9, 171.9, 172.1, 174.1, 174.4; Calc. for C$_{24}$H$_{39}$NO$_3$ (389.57): C, 73.99; H, 10.09; N, 3.60. Found: C, 73.90; H, 10.50; N, 3.52.

(S)-3,3-Dimethylbutyl 2-((S)-2-(6-methoxynaphthalen-2-yl)propanamido)-3-methylbutanoate

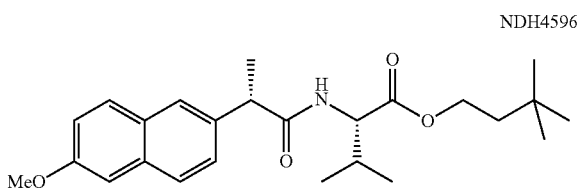 [SMILES: COc1ccc2cc([C@H](C)C(=O)N[C@H](C(=O)OCCC(C)(C)C)C(C)C)ccc2c1]

NDH4596

Clear oil, 99% yield; R_f 0.30 (Hexanes:ethyl acetate 4:1); ¹H NMR (500 MHz, CDCl₃): δ0.73 (d, 3H, J=6.90 Hz), 0:84 (s, 9H), 0.85 (d, 3H, J=7.00 Hz), 1.38-1.42 (1, 2H, J=7.65 Hz), 1.54 (s, 3H), 1.60 (d, 3H, J=7.20 Hz), 2.05-2.10 (m, 1H), 3.71-3.77 (m, 1H), 3.90 (s, 3H), 4.02-4.06 (1, 2H, J=7.45 Hz), 4.46-4.49 (dd, 1H, J=4.75, 8.73 Hz), 7.09-7.14 (m, 2H), 7.36-7.40 (dd, 1H, J=1.65, 8.48 Hz), 7.68 (s, 1H), 7.69-7.72 (dd, 2H, J=5.50, 8.60 Hz); ¹³C NMR (125 MHz, CDCl₃): δ17.7, 18.5, 19.0, 20.8, 29.5, 29.6, 31.3, 41.6, 47.1, 55.3, 57.1, 62.9, 105.7, 119.1, 126.2, 126.4, 127.5, 129.0, 129.3, 133.8, 135.9, 157.7, 174.2, 186.2; Calc. for C₂₅H₃₅NO₄ (413.55): C, 72.61; H, 8.53; N, 3.39. Found: C, 72.62; H, 8.87; N, 3.29.

(S)-3,3-Dimethylbutyl 2-(2-(1-(4-chlorobenzoyl)-5-methoxy-2-methyl-1H-indol-3-yl)acetamido)3-methylbutanoate

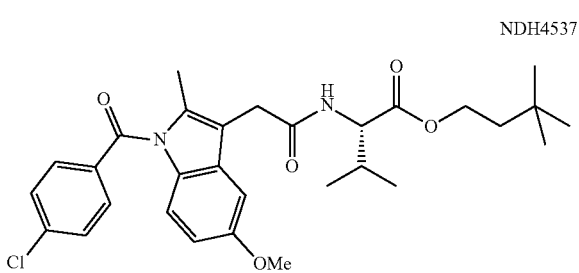 [SMILES: COc1ccc2c(c1)c(CC(=O)N[C@H](C(=O)OCCC(C)(C)C)C(C)C)c(C)n2C(=O)c1ccc(Cl)cc1]

NDH4537

White solid, 93% yield; mp 119-120° C., R_f 0.16 (Hexanes:ethyl acetate 4:1); ¹H NMR (500 MHz, CDCl₃): δ0.69 (d, 3H, J=6.90 Hz), 0.83 (d, 3H, J=6.85 Hz), 0.88 (s, 9H), 1.44-1.48 (1, 2H, J=7.55 Hz), 2.05-2.10 (m, 1H), 2.35 (s, 3H), 3.65 (m, 2H), 3.80 (s, 3H), 4.08-4.11 (1, 2H, J=7.50 Hz), 4.48-4.52 (dd, 1H, J=4.75, 8.83 Hz), 6.07 (d, 1H, J=8.80 Hz), 6.68-6.71 (dd, 1H, J=2.50, 9.00 Hz), 6.89 (d, 1H, J=2.45 Hz), 6.94 (d, 1H, J=9.00 Hz), 7.44-7.48 (m, 2H), 7.63-7.66 (m, 2H); ¹³C NMR (125 MHz, CDCl₃): δ13.4, 17.6, 19.0, 29.5, 29.7, 31.2, 32.3, 41.6, 55.7, 57.1, 63.1, 100.6, 100.9, 112.6, 112.7, 115.2, 129.2, 130.2, 131.0, 131.2, 133.7, 136.2, 139.5, 156.3, 169.7, 171.7; Calc. for C₃₀H₃₇ClN₂O₅ (541.08): C, 66.59; H, 6.89; N, 5.18. Found: C, 66.48; H, 7.12; N, 5.10.

(S)-3,3-Dimethylbutyl 2-(2-(2-(2,6-dichlorophenylamino)phenyl)acetamido)-3-methylbutanoate

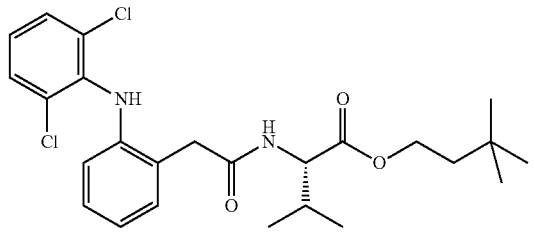 [SMILES: CC(C)[C@H](NC(=O)Cc1ccccc1Nc1c(Cl)cccc1Cl)C(=O)OCCC(C)(C)C]

NDH4591

Clear oil, 100% yield; R_f 0.54 (Hexanes:ethyl acetate 4:1); ¹H NMR (500 MHz, CDCl₃): δ0.85 (d, 3H, J=6.90 Hz), 0.88 (d, 3H, J=6.85 Hz), 0.90 (s, 9H), 1.49-1.53 (1, 2H, J=7.55 Hz), 2.11-2.15 (m, 1H), 3.72 (s, 2H), 4.12-4.16 (m, 2H), 4.53-4.57 (dd, 1H, J=4.90, 8.83 Hz), 6.16 (d, 1H, J=8.90 Hz), 6.50 (d, 1H, J=7.95 Hz), 6.89-6.92 (td, 1H, J=0.95, 7.45 Hz), 6.93-6.97 (1, 1H, J=8.00 Hz), 7.07-7.11 (td, 1H, J=1.55, 9.18 Hz), 7.16-7.19 (dd, 1H, J=1.35, 7.50 Hz), 7.31 (d, 2H, J=8.05 Hz), 7.36 (s, 1H); ¹³C NMR (125 MHz, CDCl₃): 0 17.8, 18.9, 29.6, 29.7, 31.4, 41.0, 41.7, 57.2, 63.1, 117.8, 121.6, 124.1, 124.8, 128.0, 128.8, 129.9, 130.5, 137.8, 143.0, 171.4, 171.9; Calc. for C₂₅H₃₂Cl₂N₂O₃ (479.44): C, 62.63; H, 6.73; N, 5.84. Found: C, 62.46; H, 6.48; N, 5.66.

TABLE II

Representative amino acid anti-inflammatory conjugates of Aspect II prepared by methods indicated herein are shown as examples, without limitation, of the compositions claimed herein.

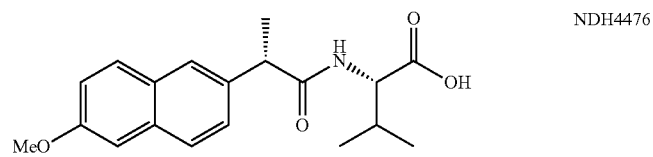

NDH4476

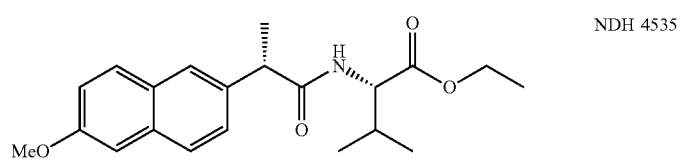

NDH 4535

TABLE II-continued
Representative amino acid anti-inflammatory conjugates of Aspect II prepared by methods indicated herein are shown as examples, without limitation, of the compositions claimed herein.
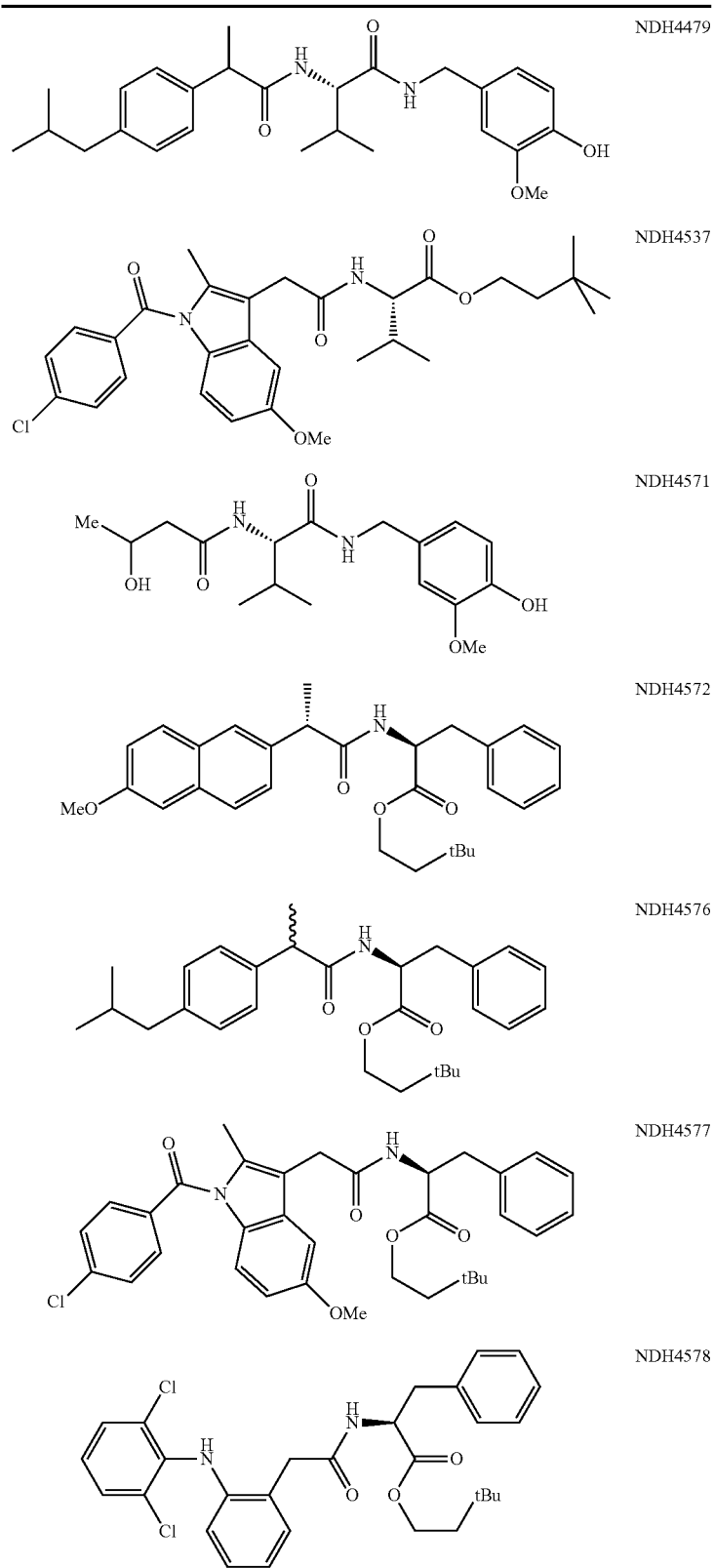
NDH4479
NDH4537
NDH4571
NDH4572
NDH4576
NDH4577
NDH4578

TABLE II-continued
Representative amino acid anti-inflammatory conjugates of Aspect II prepared by methods indicated herein are shown as examples, without limitation, of the compositions claimed herein.
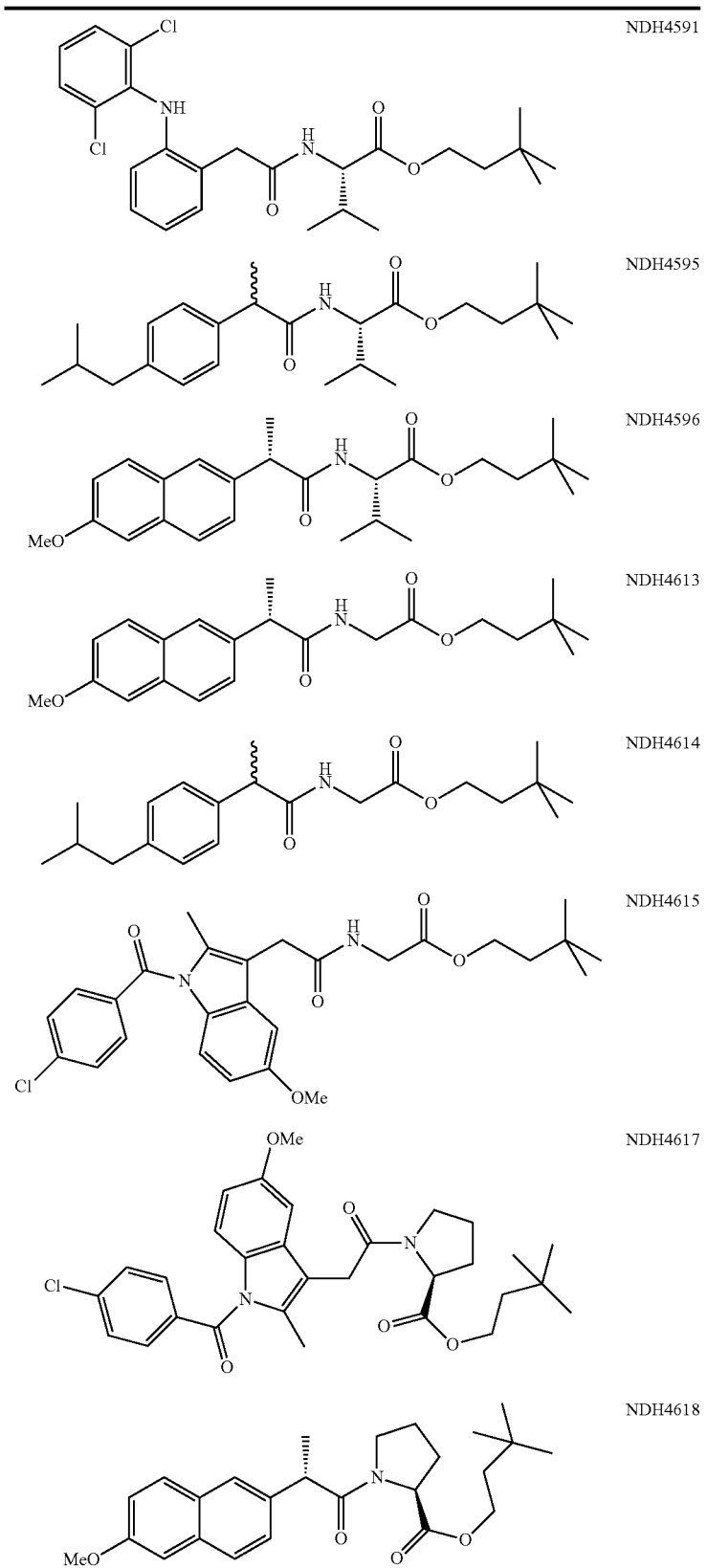
NDH4591
NDH4595
NDH4596
NDH4613
NDH4614
NDH4615
NDH4617
NDH4618

TABLE II-continued
Representative amino acid anti-inflammatory conjugates of Aspect II prepared by methods indicated herein are shown as examples, without limitation, of the compositions claimed herein.
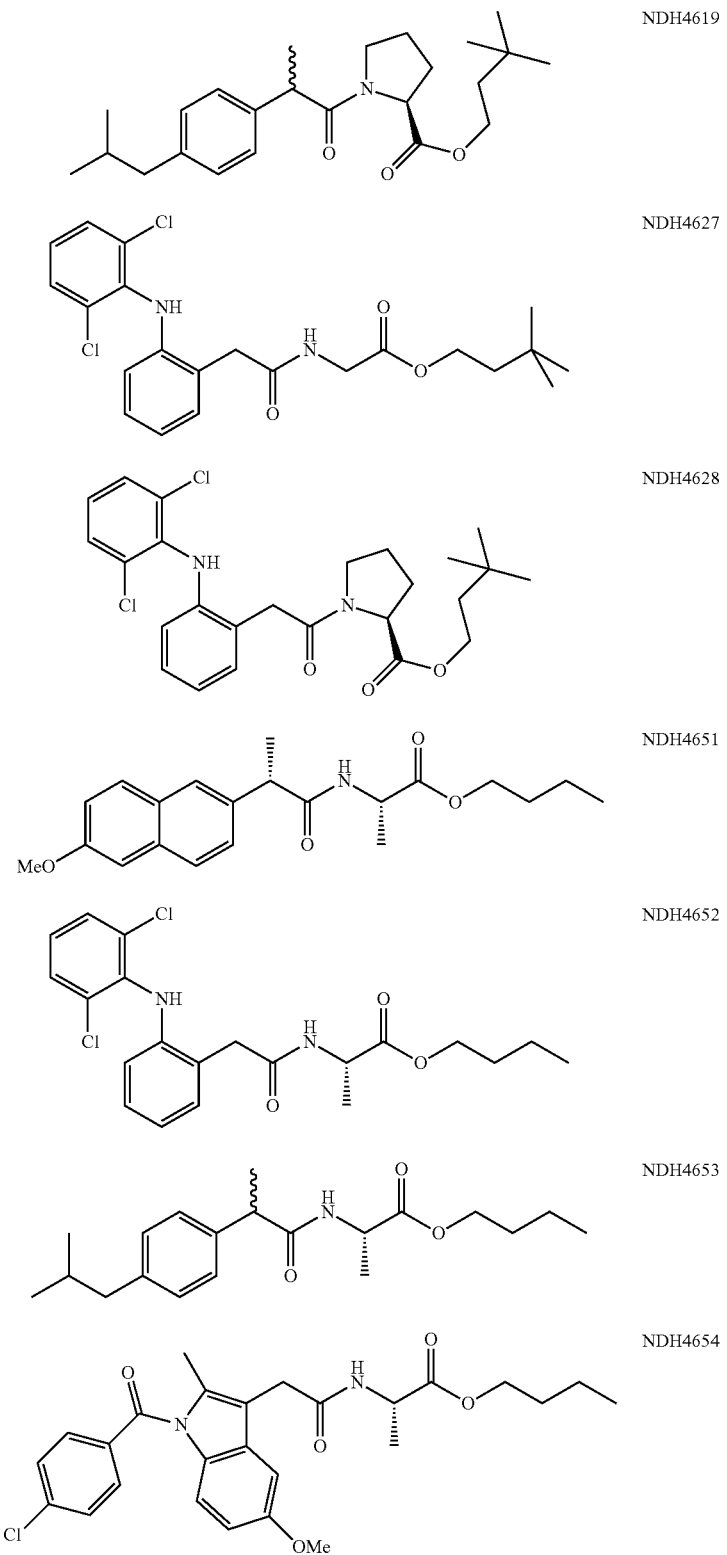
NDH4619
NDH4627
NDH4628
NDH4651
NDH4652
NDH4653
NDH4654

TABLE II-continued

Representative amino acid anti-inflammatory conjugates of Aspect II prepared by methods indicated herein are shown as examples, without limitation, of the compositions claimed herein.

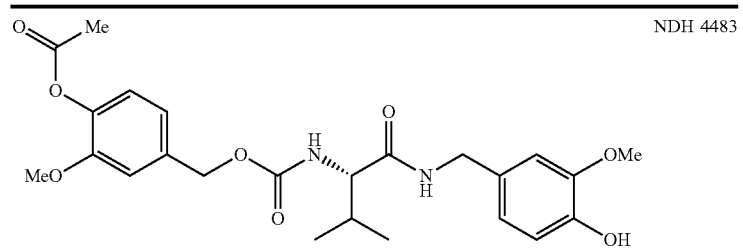

NDH 4483

All references cited herein are incorporated herein by reference in their entireties.

What is claimed is:

1. An anti-inflammatory drug-amino acid conjugate, comprising:
   (a) at least one anti-inflammatory compound conjugated with
   (b) an augmenting moiety comprising an anti-inflammatory amino acid-choline bioisostere ester, wherein the amino acid is selected from the group consisting of L-(S)-valine, L-(S)-nor-valine, L-(S)-leucine, L-(S)-iso-leucine, L-(R)-cysteine, L-(S)-proline and L-(S)-phenylalanine;

wherein said amino acid-choline bioisostere ester is an amino acid ester of $HOCH_2CH_2C(CH_3)_3$;

wherein conjugation of said conjugate is via the nitrogen atom of the amino acid of said augmenting moiety; and wherein the anti-inflammatory activity of the conjugate is greater than the sum of its parts.

2. The conjugate of claim 1, wherein said amino acid is selected from the group consisting of L-(S)-valine, L-(S)-proline and L-(S)-phenylalanine.

3. The conjugate of claim 1, wherein said anti-inflammatory compound is selected from the group consisting of non-steroidal anti-inflammatory drugs (NSAIDs).

4. The conjugate of claim 3, wherein said NSAID is selected from the group consisting of diclofenac, ibuprofen, naproxen, and indomethacin.

5. An anti-inflammatory drug-amino acid conjugate having the structure of Formula (I)

AI—NH—CHR—C(=O)O-Q¹    Formula (I)

wherein AI represents an anti-inflammatory drug moiety selected from the group consisting of NSAID-CO—moieties; wherein R is selected from the group consisting of isopropyl, benzyl, and 2-pyrrolidinyl; and wherein $Q^1$ is $-CH_2CH_2C(CH_3)_3$.

6. The amino acid conjugate of claim 5, wherein for the NSAID-CO-moiety, the NSAID is selected from the group consisting of diclofenac, ibuprofen, naproxen and indomethacin.

7. An anti-inflammatory drug-amino acid conjugate selected from the group consisting of:

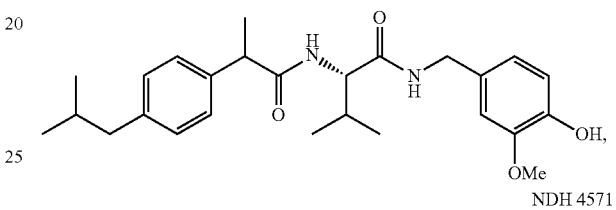

NDH 4479

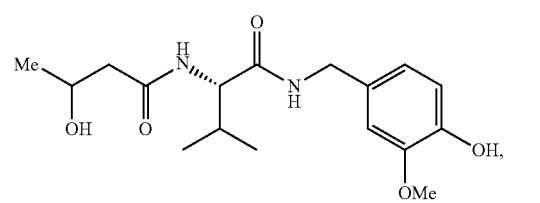

NDH 4571

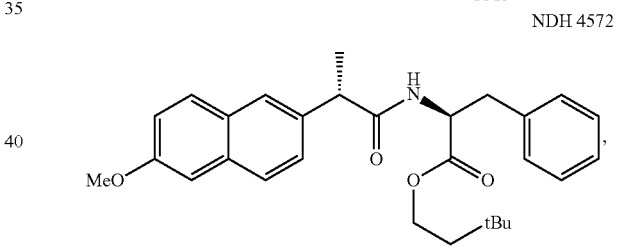

NDH 4572

NDH 4483

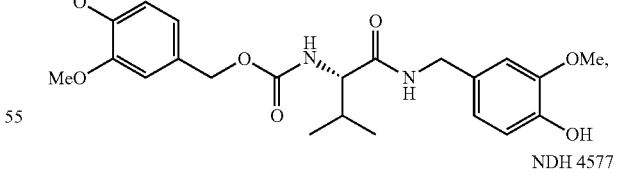

NDH 4577

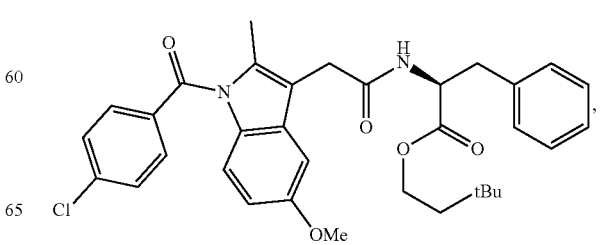

-continued

NDH 4486

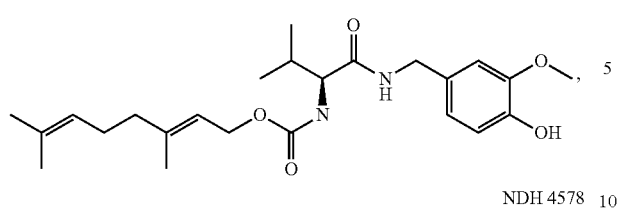

NDH 4578

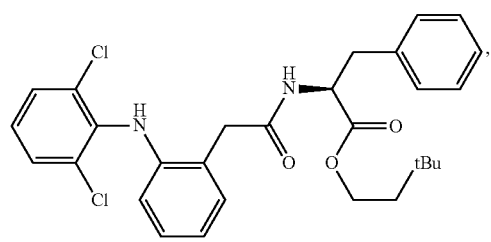

NDH 4591

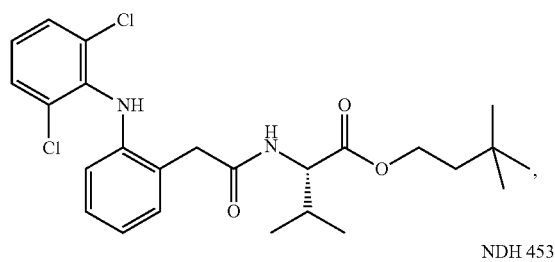

NDH 4537

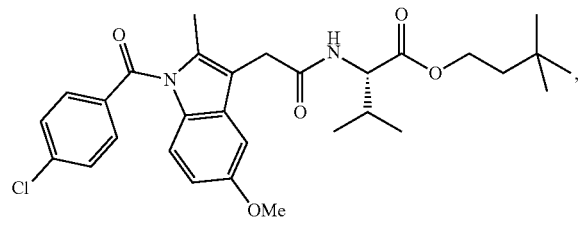

NDH 4596

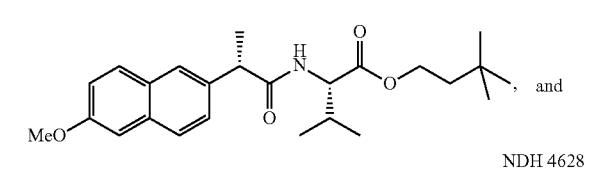

NDH 4628

NDH 4479

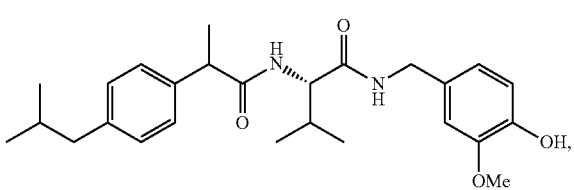

NDH 4483

NDH 4486

9. The anti-inflammatory drug-amino acid conjugate of claim 7, wherein said conjugate is (NDH 4479)

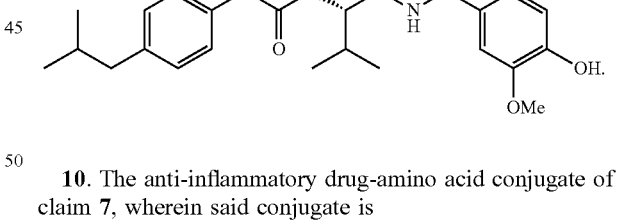

10. The anti-inflammatory drug-amino acid conjugate of claim 7, wherein said conjugate is (NDH 4483)

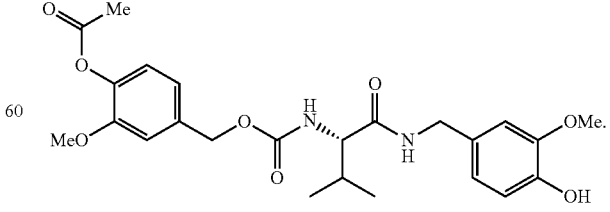

8. An anti-inflammatory drug-amino acid conjugate of claim 7 selected from the group consisting of:

11. The anti-inflammatory drug-amino acid conjugate of claim 7, wherein said conjugate is (NDH 4486)

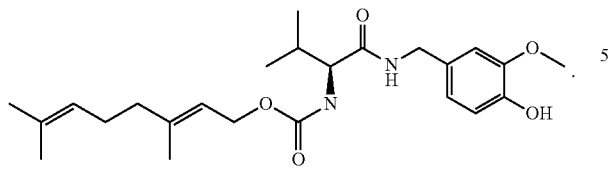

12. The anti-inflammatory drug-amino acid conjugate of claim 1, wherein said augmenting moiety is a valine ester.

13. The anti-inflammatory drug-amino acid conjugate of claim 1, wherein said augmenting moiety is an ester of L-(S)-phenylalanine.

14. The anti-inflammatory drug-amino acid conjugate of claim 1, wherein said augmenting moiety is an ester of L-(S)-proline.

15. The anti-inflammatory drug-amino acid conjugate of claim 1, wherein the amino acid of said amino acid-choline bioisostere ester is selected from the group consisting of L-(S)-valine, L-(S)-proline and L-(S)-phenylalanine, and wherein said anti-inflammatory compound is selected from the group consisting of the non-steroidal anti-inflammatory drugs diclofenac, ibuprofen, naproxen, and indomethacin.

* * * * *